(12) United States Patent
Boojamra et al.

(10) Patent No.: US 7,041,670 B2
(45) Date of Patent: May 9, 2006

(54) FLORFENICOL-TYPE ANTIBIOTICS

(75) Inventors: Constantine G. Boojamra, San Francisco, CA (US); Lee S. Chong, Newark, CA (US); Scott J. Hecker, San Diego, CA (US); Tomasz W. Glinka, Cupertino, CA (US); Dale E. Shuster, South Orange, NJ (US)

(73) Assignee: Schering-Plough Animal Health Corporation, Union, NJ (US)

( * ) Notice: Subject to any disclaimer, the term of this patent is extended or adjusted under 35 U.S.C. 154(b) by 43 days.

(21) Appl. No.: 10/410,330

(22) Filed: Apr. 8, 2003

(65) Prior Publication Data

US 2004/0082553 A1 Apr. 29, 2004

Related U.S. Application Data

(63) Continuation-in-part of application No. 10/094,688, filed on Mar. 8, 2002, now abandoned.

(51) Int. Cl.
| | |
|---|---|
| *C07D 237/06* | (2006.01) |
| *C07D 239/24* | (2006.01) |
| *C07D 253/065* | (2006.01) |
| *A61K 31/44* | (2006.01) |
| *A61P 31/04* | (2006.01) |

(52) U.S. Cl. .................... 514/242; 514/247; 514/256; 514/344; 514/349; 514/351; 514/363; 514/374; 514/378; 514/396; 544/182; 544/238; 544/332; 544/335; 544/329; 546/329; 548/136; 548/138; 548/146; 548/184; 548/206; 548/214; 548/240; 548/245; 548/300.1; 548/326.5

(58) Field of Classification Search .............. 544/182, 544/238, 332, 335, 329; 546/329; 548/136, 548/138, 146, 184, 206, 214, 240, 245, 300.1, 548/326.5; 514/242, 247, 256, 344, 349, 514/351, 363, 374, 628, 629, 630, 365, 370, 514/372, 396, 378, 520, 275; 564/212; 560/2
See application file for complete search history.

(56) References Cited

U.S. PATENT DOCUMENTS

| | | |
|---|---|---|
| 3,183,265 A | 5/1965 | von Strandtmann et al. |
| 4,235,892 A | 11/1980 | Nagabhushan |
| 4,361,557 A | 11/1982 | Nagabhushan |
| 4,582,918 A | 4/1986 | Nagabhushan et al. |
| 4,743,700 A | 5/1988 | Jommi et al. |
| 4,876,352 A | 10/1989 | Schumacher et al. |
| 4,918,095 A | 4/1990 | Della Bella et al. |
| 4,973,750 A | 11/1990 | Nagabhushan et al. |
| 5,082,863 A | 1/1992 | Apelian et al. |
| 5,105,009 A | 4/1992 | Jommi et al. |
| 5,153,328 A | 10/1992 | Jommi et al. |
| 5,243,056 A | 9/1993 | Jommi et al. |
| 5,332,835 A | 7/1994 | Jommi et al. |
| 5,352,832 A | 10/1994 | Wu et al. |
| 5,382,673 A | 1/1995 | Clark et al. |
| 5,567,844 A | 10/1996 | Jommi et al. |
| 5,621,111 A | 4/1997 | Lui et al. |
| 5,663,361 A | 9/1997 | Towson et al. |
| 5,789,599 A | 8/1998 | Davis et al. |
| 5,908,937 A | 6/1999 | Jommi et al. |

FOREIGN PATENT DOCUMENTS

| | | |
|---|---|---|
| BE | 638 755 A | 4/1964 |
| BE | 669 982 A | 3/1966 |
| EP | 0 014 437 B1 | 2/1983 |
| FR | 4 604 M | 11/1966 |

OTHER PUBLICATIONS

Snyder et al., J. Med. Liban 48(4): 208–214, 2000.*
Rogoz, Dissertationes Pharmaceuticae 16(2): 157–169, 1964. CA 62: 66234, 1965.*
Supniewski et al., Bulletin de l'Academie Polonaise des Sciences, Serie des Sciences Biologigues 9, 231–234, 235–239, 1961. CA 56: 7514, 7507, 1962.*
National Office of Animal Health, Antibiotics for Animals—An Overview, Briefing Document No. 6.
Hoflack, G., et al., "Efficacy of tilmicosin phosphate (Pulmotil premix) in feed for the treatment of a clinical outbreak of *Actinobacillus pleuropneumoniae* infection in growing–finishing pigs," *J Vet Med B Infect Dis Vet Public Health* 48(9):655–64 (Nov. 2001) (Abstract Only).
Compendium of Veterinary Products, Seventh Edition, pp. 1841–1842, 2043 (2003).
Hansch, Corwin, et al., "Structure–Activity Relationship of Chloramphenicols," *Journal of Medicinal Chemistry* 16:917–922 (1973).
Mitscher, Lester A., et al., "Circular Dichroism Studies of Aryl Diastereoisomers. 3. Cupra A Spectra of Chloramphenicol Derivatives," *Journal of Medicinal Chemistry* 16:98–101 (1973).
Nielsen, Peter E., et al., "Light Sensitive Chloramphenicol Analogues," *Acta Chemica Scandinavica B* B29:662–66 (1975).

(Continued)

Primary Examiner—Venkataraman Balasubramanian

(57) ABSTRACT

The present invention relates to novel florfenicol compounds having the chemical structure:

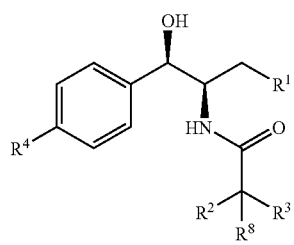

wherein the compounds are useful for the treatment and/or prevention of bacterial infections in a broad range of patients such as, without limitation, birds, fish, shellfish and mammals.

27 Claims, No Drawings

OTHER PUBLICATIONS

Von Strandtmann, Maximilian, et al., "Synthesis of p–Acyl Analogs of Chloramphenicol and their Antimicrobial Properties," *Journal of Medicinal Chemistry* 10:888–90 (1967).

Bolhofer, William, "The Preparation of Hydroxyphenylserines from Benzyloxybenzaldehydes and Glycine," *J. Am. Chem. Soc.* 76:1322–26 (1954).

Bolton, Lance F., et al., "Detection of Multidrug–Resistant *Salmonella enterica* Serotype *typhimurium* DT104 Based on a Gene Which Confers Cross–Resistance to Florfenicol and Chloramphenicol," *Journal of Clinical Microbiology* 37:1348–1351 (1999).

Cloeckaert, Axel, et al., "Nonenzymatic Chloramphenicol Resistance Mediated by IncC Plasmid R55 Is Encodd by a floR Gene Variant," *Antimicrobial Agents and Chemotherapy* 45:2381–82 (2001).

Evans, David D., et al., "Analogues of Chloramphnicol. Part III*," *J. Chem. Soc.* 1687–90 (1954).

Grehn, Leif, et al., "A Simple Method for tert–Butoxycarbonylation of Amides," *Acta Chemica Scandinavica B* 40:745–750 (1986).

Herbert, Richard B., et al., "Preparation of (2R, 3S)–β–hydroxy–α–amino acids by use of a novel *Streptomyces* aldolase as a resolving agent for racemic material" *Can. J. chem.* 72:114–17 (1994).

Ishizuka, Tadao, et al., "Mild and Selective Ring–Cleavage of Cyclic Carbamates to Amino Alcohols," *Tetrahedron Letters* 28:4185–88 (1987).

Jommi, Giancarlo, et al., "2–Oxazolidinones as Regioselective Protection of β–Amino Alcohols in the Synthesis of 2–Amino–1–Aryl–3–Fluoro–1–Proponals," *Gazz. Chim. Ital.* 116:485–89 (1986).

Jommi, Giancarlo, et al., "Mild Recovery of β–Amino Alcohols from the Corresponding 2–Oxazolidinones(*)" *Gazzetta Chimica Italiana* 118:75–76 (1988).

Keyes, Kathleen, et al., "Detection of Florfenicol Resistance Genes in *Escherichia coli* Isolated from Sick Chickens," *Antimicrobial Agents and Chemotherapy* 44:421–24 (2000).

Kim, Eun–heui, et al., "Sequence Analysis of the Florfenicol Resistance Gene Encoded in the Transferable R–Plasmid of a Fish Pathogen, *Pasteurella piscicida*," *Microbiol. Immunol.* 40:665–69 (1996).

Lal, Gauri S., et al., "Bis(2–methoxyethyl)aminosulfur Trifluoride: A New Broad–Spectrum Deoxofluorinating Agent with Enhanced Thermal Stability," *J. Org. Chem.* 64:7048–54 (1999).

Lam, Patrick Y.S., et al., "New Aryl/Heteroaryl C–N Bond Cross–coupling Reactions via Arylboronic Acid/Cupric Acetate Arylation," *Tetrahedron Letters* 39:2941–44 (1998).

Lam, Patrick Y.S., et al., "Copper Promoted Aryl/Saturated Heterocyclic C–N Bond Cross–Coupling with Arylboronic Acid and Arylstannane," *Synlett* 5:674–76 (2000).

Lam, Patrick Y.S., et al., "Copper–catalyzed general C–N and C–O bond cross–coupling with arylboronic acid" *Tetrahedron Letters* 42:3415–18 (2001).

Morris, et al., "Analogues of Chloramphenicol. Part I," *J. Chem. Soc.*1680–86 (1954).

Pines, Seemon, et al. "Substituent Effects in the Reaction of N–Benzoyl–β–arylserinates with Thionyl Chloride," *J. Org. Chem.*37:292–97(1972).

Rebstock, M.C., et al., "Chloramphenicol (Chloromycetin). IV. Chemical Studies," *J. Am. Chem. Soc.* 71:2458–62 (1949).

Shaw, W.V., et al., "Chloramphenicol Resistance by Enzymatic Acetylation: Comparative Aspects," *Antimicrobial Agents and Chemotherapy* 257–63 (1968).

Von Strandtmann, M., et al., "Synthesis of p–Acyl Analogs of Chloramphenicol and Their Antimicrobial Properties," *J. Am. Chem.* 10:888–90 (1967).

Yu, Kuo–Long, et al., "Retinoic Acid Receptor β, γ–Selective Ligands: Synthesis and Biological Activity of 6–Substituted 2–Naphthoic Acid Retinoids," *J. Med. Chem.* 39:2411–21 (1996).

* cited by examiner

FLORFENICOL-TYPE ANTIBIOTICS

RELATED APPLICATIONS

This Application is a continuation-in-part of U.S. patent application Ser. No. 10/094,688, filed Mar. 8, 2002 now abandoned and entitled "Novel Florfenicol-type Antibiotics." The '688 application is incorporated as if fully set forth herein.

FIELD OF THE INVENTION

The present invention relates to the fields of organic chemistry, pharmaceutical chemistry, biochemistry and medicine. In particular, it relates to novel florfenicol-type antibiotics.

BACKGROUND OF THE INVENTION

Florfenicol is a broad spectrum antibiotic with activity against many gram-negative and gram-positive bacteria. Florfenicol is useful for the prevention and treatment of bacterial infections due to susceptible pathogens in birds, reptiles, fish, shellfish and mammals. One of its primary uses is in the treatment of pneumonia and associated respiratory infections in cattle (often referred to generically as Bovine Respiratory Disease or BRD) caused by *Mannhemia haemolytica, Pasturella multocida* and(or) *Haemophilus somnus*. It is also indicated in the treatment of pododermatitis in cattle caused by *Fusobacterium necrophorum* and *Bacterioides melaninogenicus*, swine respiratory disease caused by *Pasteurella multocida, Actinobacillus pleuropneumoniae, Streptococcus suis, Salmonella cholerasuis* and(or) *Mycoplasma* spp., colibacillosis in chickens caused by *Escherichia coli*, enteric septicemia in catfish caused by *Edwardsiella ictaluri*, and furunculosis in salmon caused by *Aeromonas salmonicida*. Other genera of bacteria that have exhibited susceptibility to florfenicol include. *Enterobacter, Klebsiella, Staphylococcus, Enterococcus, Bordetella, Proteus,* and *Shigella*. In particular, chloramphenicol resistant strains of organisms such as *K. pneumoniae, E. cloacae, S. typhus* and *E. coli* are susceptible to florfenicol.

Florfenicol is a structural analog of thiamphenicol, which in turn is a derivative of chloramphenicol in which the aromatic nitro group, which nitro group has been implicated in

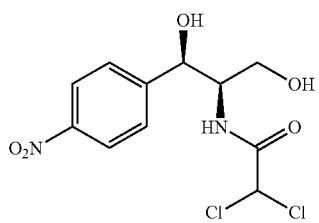

chloramphenicol

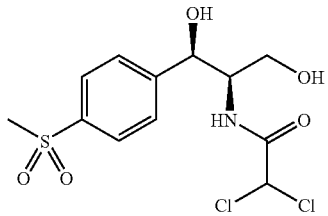

thiamphenicol

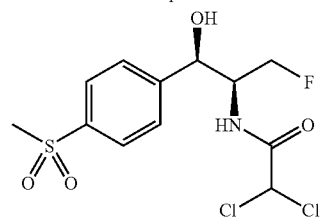

florfenicol chloramphenicol-induced, non-dose related irreversible aplastic anemia in humans, is replaced with a methylsulfonyl group. Florfenicol has a fluorine atom in place of the primary hydroxyl group of chloramphenicol and thiamphenicol. This renders florfenicol less susceptible to deactivation by bacteria containing the plasmid-encoded enzyme, chloramphenicol acetyl transferase (CAT), which acetylates the primary hydroxyl group of chloramphenicol and thiamphenicol, thereby preventing them from binding to ribosomal subunits of susceptible bacteria. Ribosomal binding is the primary mechanism of action of the chloramphenicol antibiotics and results in inhibition of peptidyl transferase, which is responsible for the transfer of amino acids to growing peptide chains and subsequent protein formation in bacteria. Nonetheless, compounds having the primary hydroxyl group do have utility in the treatment of bacterial infections, as evidenced by the continuing use of chloramphenicol and thiamphenicol throughout the world.

In recent years, a number of bacterial genera and species have begun to exhibit some resistance to florfenicol. For example, resistance has been observed in *Salmonella* species (Bolton, L. F., et al., *Clin. Microbiol.* 1999, 37, 1348), *E. coli* (Keyes, K., et al., *Antimicrob. Agents Chemother.*, 2000, 44, 421.), *Klebsiella pneumoniae* (Cloeckaert, A., et al., *Antimicrob. Agents Chemother.*, 2001, 45, 2381), and in the aquacultural pathogen, *Photobacterium damselae* subsp. *piscicida* (formerly *Pasteurella piscicida*) (Kim, E., et al., *Microbiol. Immunol.*, 1996, 40, 665). This resistance has been traced to a highly conserved gene (flo) that produces an antibiotic efflux pump (Flo).

The emergence, and threatened spread, of resistance to florfenicol has fostered the need for new antibiotics that retain or exceed the activity of florfenicol, maintain its imperviousness to the CAT enzyme and, in addition, are not substrates for the Flo efflux pump. The compounds of the present invention are such antibiotics.

SUMMARY

Thus, an embodiment of this invention is a compound having the chemical formula:

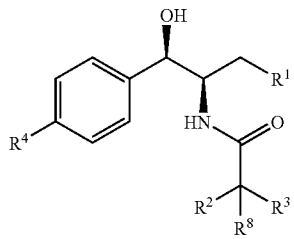

wherein:

R¹ is selected from the group consisting of —OH and —F;
R² and R³ are independently selected from the group consisting of hydrogen, (1C–4C)alkyl, halo, —CF₃, —NH₂, —CN and N₃;
R⁴ is selected from the group consisting of:
—C(=R⁵)R⁶,
  wherein:
  R⁵ is selected from the group consisting of oxygen, N—C≡N, and NOR⁷,
    wherein:
    R⁷ is selected from the group consisting of hydrogen, alkyl, aryl, heteroaryl, alicyclic and heteroalicyclic;
  R⁶ is selected from the group consisting of hydrogen, (1C–4C)alkyl, (3C–6C)cycloalkyl, (1C–4C)alkoxy, aryl, heteroaryl, alicyclic and heteroalicyclic;

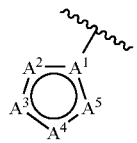

wherein:
A¹ is carbon or nitrogen;
A², A³, A⁴ and A⁵ are independently selected from the group consisting of carbon, nitrogen, oxygen and sulfur, provided that at least one of A¹–A⁵ is not carbon, that the total number of nitrogen, oxygen and sulfur atom in the ring does not exceed 4 and that the ring is aromatic;
carbon atoms in the ring are independently substituted with an entity selected from the group consisting of hydrogen, (1C–4C)alkyl, (3C–6C)cycloalkyl, (1C–4C)alkylO—, —CF₃, —OH, —CN, halo, (1C–4C)alkylS(O)—, (1C–4C)alkylS(O)₂—, NH₂SO₂—, (1C–4C)alkylNHSO₂—, ((1C–4C)alkyl)₂NSO₂—, —NH₂, (1C–4C)alkylNH—, ((1C–4C)alkyl)₂N—, (1C–4C)alkylSO₂NH—, (1C–4C)alkylC(O)—, (3C–6C)cycloalkylC(O)—, (1C–4C)alkylOC(O)—, (1C–4C)alkylC(O)NH—, —C(O)NH₂, (1C–4C)alkylNHC(O)— and ((1C–4C)alkyl)₂NC(O)—, wherein any of the alkyl groups in any of the substituents may optionally be substituted with a group selected from halo and —OH;
if A¹ is carbon and the ring does not contain oxygen or sulfur, one of the nitrogen atoms may optionally be substituted with an entity selected from the group consisting of (1C–4C)alkyl, (1C–4C)alkylS(O)₂— and —NH₂;

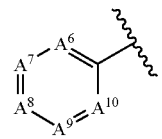

wherein:
A⁶, A⁷, A⁸, A⁹ and A¹⁰ are independently selected from the group consisting of carbon, nitrogen and $$\diagdown\!\!\!\!\diagdown\!\!\!\!\overset{}{\underset{/}{N^+}}\!\!-\!O^-,$$

provided that only one of A⁶–A¹⁰ at a time can be $$\diagdown\!\!\!\!\diagdown\!\!\!\!\overset{}{\underset{/}{N^+}}\!\!-\!O^-;$$

carbon atoms in the ring are independently substituted with an entity selected from the group consisting of hydrogen, (1C–4C)alkyl, (3C–6C)cycloalkyl, (1C–4C)alkylO—, —CF₃, —OH, —CN, halo, (1C–4C)alkylS(O)—, (1C–4C)alkylS(O)₂—, NH₂SO₂—, (1C–4C)alkylNHSO₂—, ((1C–4C)alkyl)₂NSO₂—, —NH₂, (1C–4C)alkylNH—, ((1C–4C)alkyl)₂N—, (1C–4C)alkylSO₂NH—, (1C–4C)alkylC(O)—, (3C–6C)cycloalkylC(O)—, (1C–4C)alkylOC(O)—, (1C–4C)alkylC(O)NH—, —C(O)NH₂, (1C–4C)alkylNHC(O)—, ((1C–4C)alkyl)₂NC(O)— and —OCH₂O—, the oxygen atoms in the —OCH₂O— substituent being bonded to adjacent ring carbon atoms, wherein any of the alkyl groups in any of the substituents may optionally be substituted with a group selected from halo and —OH;
R⁸ is hydrogen in all compounds, except when R² and R³ are both F, in which case R⁸ is hydrogen or F; and,
the compound is either a racemate having the relative stereochemistry shown or is substantially enantiomerically pure and has the absolute stereochemistry shown.

In an embodiment of this invention, R¹ is —F.

In an embodiment of this invention, R² and R³ are independently selected from the group consisting of Cl and F.

In an embodiment of this invention, R⁸ is hydrogen.

In an embodiment of this invention, R⁴ is —C(=R⁵)R⁶ wherein R⁵ and R⁶ are as defined above.

In an embodiment of this invention, R⁴ is CH₃C(O)—.

In an embodiment of this invention, R⁴ is

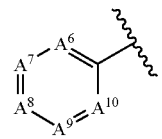, wherein:
A⁶, A⁷, A⁸, A⁹ and A¹⁰ are as defined above, and, any of A⁶–A¹⁰ that is carbon is substituted with an entity selected from the group consisting of hydrogen, —NH₂, halo-, —CN, (1C–4C)alkyl-, (1C–4C)alkylC(O)—, (1C–4C)alkylS(O)—, (1C–4C)alkylS(O)₂—, NH₂SO₂—, (1C–4C)alkylSO$_2$NH—, (1C–4C)alkylNHSO$_2$—, ((1C–4C)alkyl)$_2$NSO$_2$—, wherein any of the alkyl groups in any of the substituents may optionally be substituted with halo or —OH.

In an embodiment of this invention, R$^4$ is

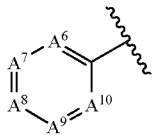

and one, two or three of A$^6$–A$^{10}$ is/are nitrogen; and, one or two of the remaining carbon atoms in the ring is/are optionally substituted with —NH$_2$, all other carbon atoms in the ring being unsubstituted.

In a presently preferred embodiment of this invention, R$^4$ is selected from the group consisting of:

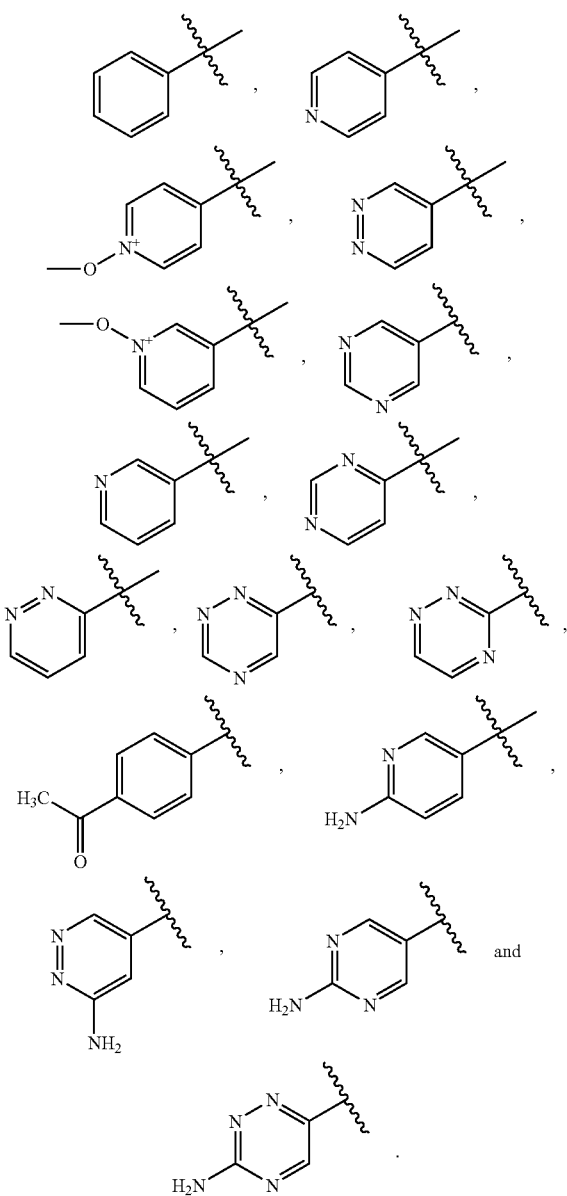

In an embodiment of this invention, R$^4$ is

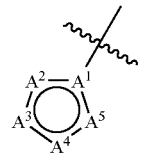

as defined above.

In an embodiment of this invention, R$^4$ is

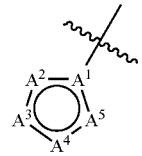

and all carbon atoms and nitrogen atoms are unsubstituted.

In an embodiment of this invention, R$^4$ is

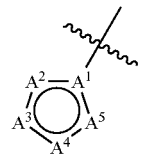

and one of A$^2$–A$^5$ that is carbon is substituted with an —NH$_2$ group, all other carbon and, if applicable, nitrogen atoms in the ring being unsubstituted.

In a presently preferred embodiment of this invention, R$^4$ is selected from the group consisting of:

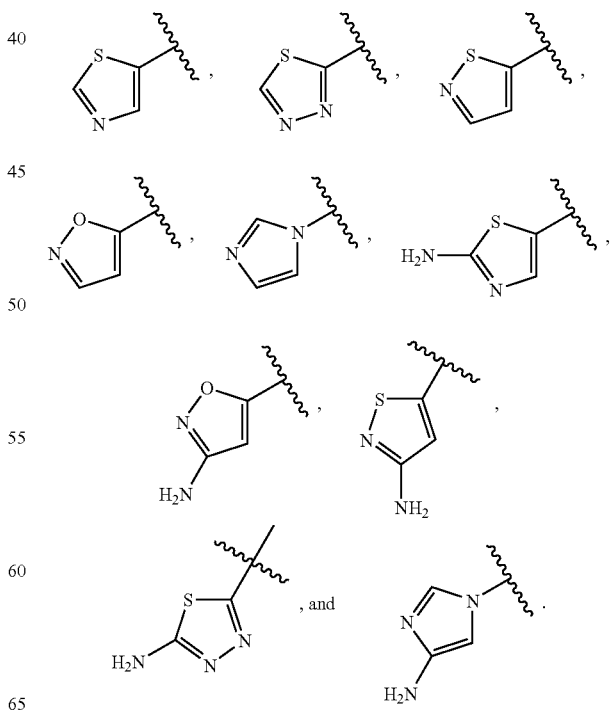

A presently preferred embodiment of this invention is a compound selected from the group consisting of:
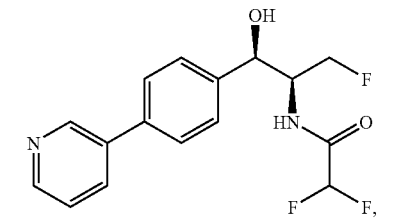
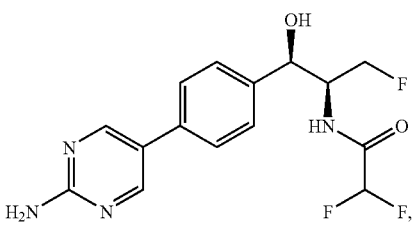
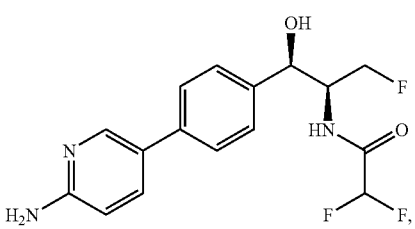
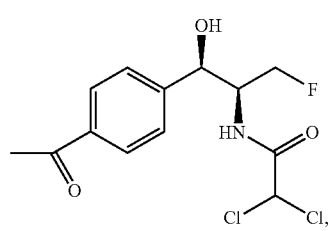
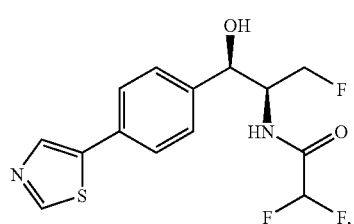
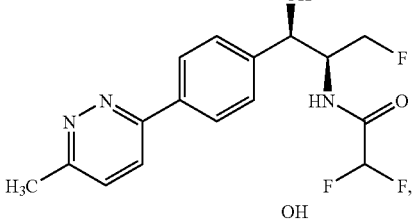
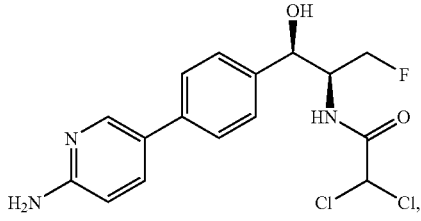
-continued
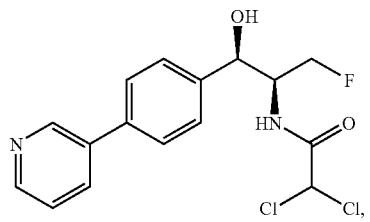
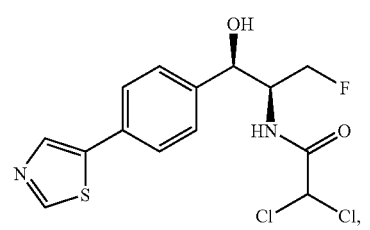
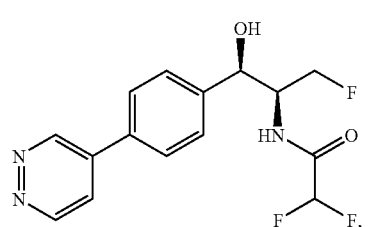
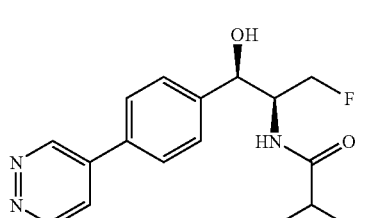
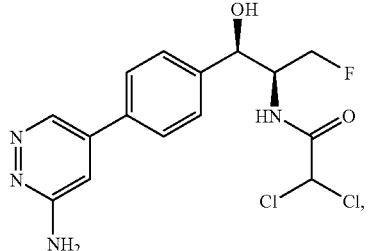
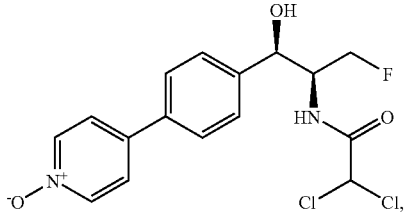
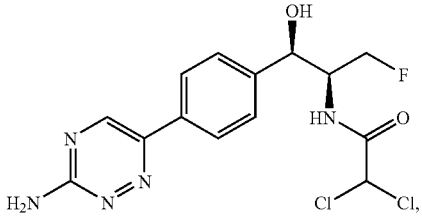

-continued
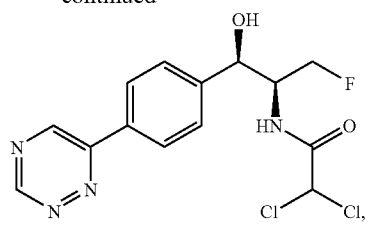
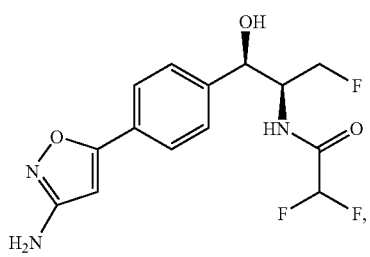
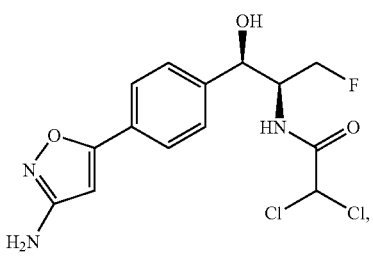
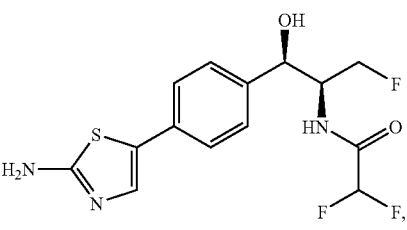
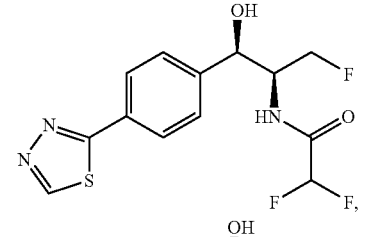
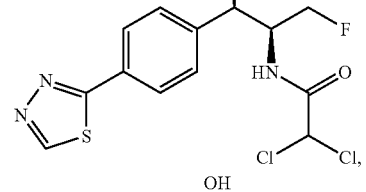
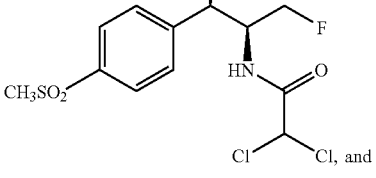
-continued
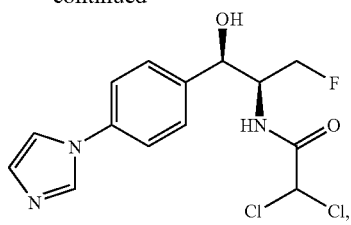
wherein the compound is either a racemate having the relative stereochemistry shown or is substantially enantiomerically pure and has the absolute stereochemistry shown.
A presently particularly preferred embodiment of this invention is a compound selected from the group consisting of:
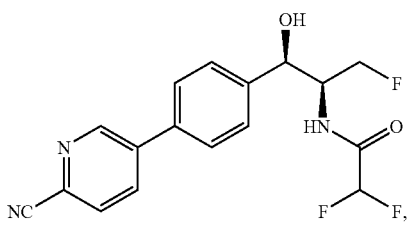
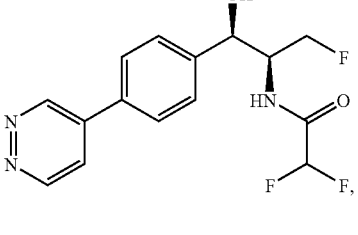
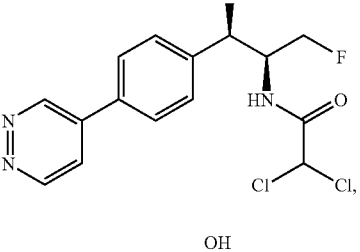
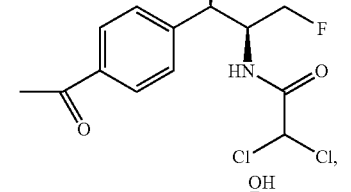
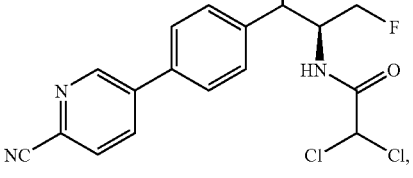

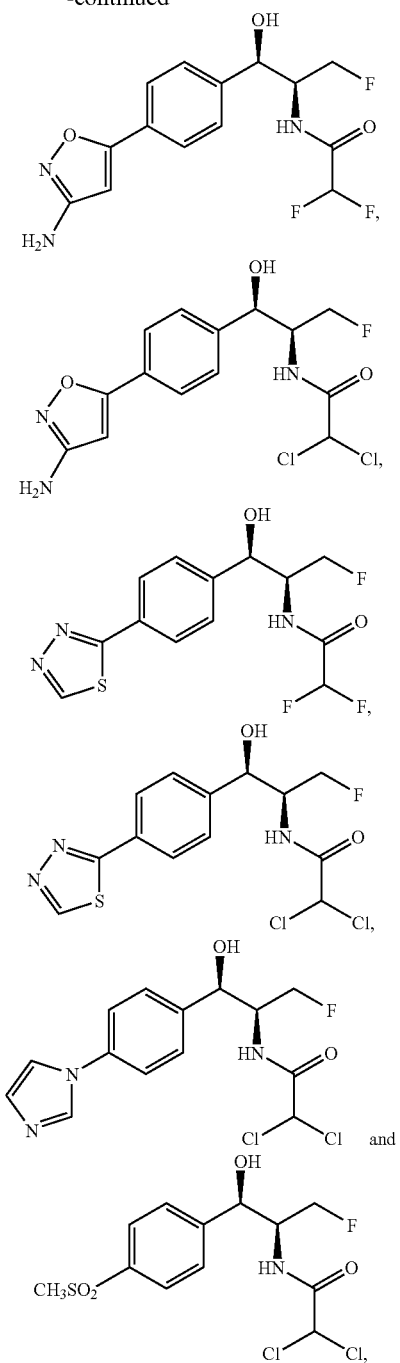

wherein the compound is either a racemate having the relative stereochemistry shown or is substantially enantiomerically pure and has the absolute stereochemistry shown.

In another particularly preferred embodiment of this invention, the compound herein is substantially enantiomerically pure and has a 1—(R)—2—(S) absolute configuration.

An embodiment of this invention is a method of treating or preventing a bacterial infection, comprising administering to a patient in need thereof a pharmaceutically effective amount of a compound hereof.

In an embodiment of this invention, the bacterial infection is caused by a bacteria of the genus *Pasteurella, Haemophilus, Fusobacterium, Bacterioides, Aeromonas, Enterobacter, Escherichia, Klebsiella, Salmonella, Shigella, Actinobacillus, Streptococcus, Mycoplasma, Edwardsiella, Staphylococcus, Enterococcus, Bordetella, Proteus,* or *Mannheimia*.

In an embodiment of this invention the bacterial infection is caused by *Mannhemia haemolytica, Pasteurella multocida, Haemophilus somnus, Fusobacterium necrophorum, Bacterioides melaninogenicus, Actinobacillus pleuropneumoniae, Streptococcus suis, Salmonella cholerasuis, Mycoplasma bovis, Mycoplasma hyopneumoniae, Mycoplasma hyorhinis, Mycoplasma gallisepticum, Edwardsiella ictaluri, Escherichia coli, Enterobacter cloacae, Staphylococcus aureus, Staphylococcus intermedius, Enterococcus faecalis, Enterococcus faecium, Klebsiella pneumoniae, Klebsiella oxytoca, Enterobacter cloacae, Proteus mirabilis,* or *Aeromonas salmonicida*.

DETAILED DESCRIPTION OF THE INVENTION

Brief description of the Tables

Table 1 shows structures of representative compounds of this invention. The table and the compounds therein are not intended, nor should they be construed, to limit this invention in any manner whatsoever.

Table 2 is a list of the microorganisms against which the compounds of this invention were tested. The list is not intended, nor should it be construed, to limit the scope of this invention in any manner whatsoever.

Definitions

As used herein, "halo" refers to fluorine, chlorine, bromine or iodine.

As used herein, "alkyl" refers to a saturated (containing no multiple bonds) aliphatic (no delocalized π-electron system), hydrocarbon (containing, if unsubstituted, only carbon and hydrogen). The designation ($n_1C$–$n_2C$)alkyl, wherein $n_1$ and $n_2$ are integers from 1–6, refers to a straight chain or branched chain alkyl comprising from $n_1$ to $n_2$ carbon atoms. For example, (1C–4C)alkyl refers to $CH_3$—, $CH_3CH_2$—, $CH_3CH_2CH_2$—, $CH_3CH(CH_3)$—, $CH_3CH_2CH_2CH_2$—, $CH_3CH_2CH(CH_3)$— or $(CH_3)_3C$—. The alkyl group may be unsubstituted or substituted with one or more moieties selected from the group consisting of halo, —OH, $OCH_3$, and —C≡N.

As used herein, "cycloalkyl" refers to an all-carbon cyclic or fused multicyclic ring, which, although it may contain one or more double bonds, maintains an essentially aliphatic character; that is, the double bonds do not interact to form a delocalized π-electron system around the ring. For the purposes of this invention, the ring may contain up to 7 carbon atoms. The designation (3C–6C)cycloalkyl refers to 3, 4, 5, and 6-member all-carbon-atom rings. As used herein, "fused" means that two cycloalkyl groups share at least one ring atom between them. Thus, such compounds as spiro [4.4]nonane are considered "fused" for the purposes of this invention. More commonly, fused rings share two adjacent ring carbon atoms. An example of such a fused system is decalin. A cycloalkyl ring may be unsubstituted or substituted with a moiety selected from the group consisting of —OH, —$OCH_3$, halo and —C≡N.

As used herein, "aryl" refers to an all-carbon 6-member ring or two fused six-member rings, the ring or fused rings having a delocalized π-electron system. By "fused" is meant that each ring of the system shares two adjacent ring carbon atoms with at least one other ring. An aryl ring may be unsubstituted or substituted with one or more moieties selected from the group consisting of —OH, —$OCH_3$, halo and —C≡N.

As used herein, "heteroaryl" refers to a five-member or six-member ring or to two rings, i.e., two 5-member, two six-member or a five- and a six-member ring fused together wherein the ring or fused ring has a delocalized 1-electron system. If a ring is six-membered, it must consist of carbon and nitrogen only and may contain from one to four nitrogen atoms. If a ring is five-membered, it must contain one nitrogen, oxygen or sulfur atom and may contain one, two or three additional nitrogen atoms. A five-member ring with a circle in the center indicates that the ring is heteroaromatic. The circle is used to emphasize the fact that the location of the double bonds that participate in making the ring heteroaromatic is not static, rather it is dependent on the nature of the atoms forming the ring, i.e., whether they are carbon, nitrogen, oxygen or sulfur and what groups, if any, are bonded to them. The actual structure of any five-member heteroaromatic will be immediately apparent to those skilled in the art once the ring atoms are designated. With regard to heteroaromatic groups, the term fused has the same meaning as in the case of aryl groups. A heteroaryl group may be unsubstituted or substituted with any of the moieties described above with regard to aryl groups.

As used herein, "heteroalicyclic" refers to a cyclic or fused cyclic ring system containing atoms selected from the group consisting of carbon, nitrogen, oxygen and sulfur but no delocalized π-electron system. "Fused" has the same meaning set forth above with regard to cycloalkyl rings. Likewise, a heteroalicyclic ring may be unsubstituted or substituted with the same moieties described above for cycloalkyl rings.

Whenever a ring carbon atom is stated to be "unsubstituted," it is understood that any unfilled valences are in fact occupied by hydrogen atoms. Likewise, if a ring nitrogen atom is capable of being further substituted and it is stated to be unsubstituted, it means that the nitrogen is bonded to a hydrogen atom.

As used herein, "relative stereochemistry" refers to the positioning in space of substituents relative to one another.

As used herein, "absolute stereochemistry" refers to the exact positioning of substitutents in three-dimensional space as determined by the Cahn-Ingold-Prelog rules, the application of which are well-known to those skilled in the art.

As used herein, an "enantiomer" refers to one of the two absolute stereochemical configurations of a molecule that rotates plane polarized light in one direction or the other (i.e., counterclockwise from its original axis, conventionally called "left," or clockwise, conventionally referred to as "right"). By "substantially enantiomerically pure" is meant that the compound consists of greater than 90% of the one enantiomer, preferably greater than 95%, and most preferably greater than 99%.

As used herein, a "racemate" refers to a 1:1 mixture of the two enantiomers of a compound. Racemic mixtures are designated by a (+/−) indicator. Substantially enantiomerically pure compounds are shown without the indicator.

As used herein, "patient" refers to birds, reptiles, fish, shellfish, and mammals. In particular it refers to birds such as, without limitation, chickens and turkeys, fish such as, without limitation, salmon, trout, catfish and yellowtail, mammals such as, without limitation, cats, dogs, rabbits, sheep, cattle, pigs, horses and goats and to human beings.

Discussion

The compounds of this invention are expected to be useful for the treatment of bacterial infections in patients.

Compounds

The compounds of the present invention are set forth generally in the Summary, above. Exemplary compounds of this invention are shown in Table 1. Neither the table nor the compounds shown therein are intended, or are to be construed, as limiting the scope of this invention in any manner whatsoever.

TABLE 1

| Compound # | Structure |
|---|---|
| 28 | 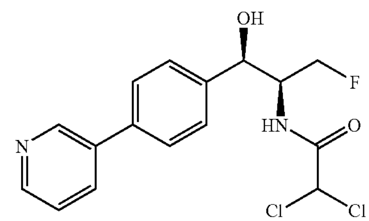 |
| 29 |  (+/−) |
| 41 | 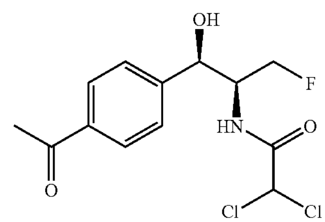 |
| 47 |  (+/−) |
| 48 |  (+/−) |
| 49 |  (+/−) |

TABLE 1-continued

| Compound # | Structure |
|---|---|
| 50 | 4'-cyano-biphenyl-CH(OH)-CH(NHC(O)CHF₂)-CH₂F (+/−) |
| 51 | 4'-(methylsulfonyl)-biphenyl-CH(OH)-CH(NHC(O)CHF₂)-CH₂F (+/−) |
| 52 | 4-(thiophen-3-yl)-phenyl-CH(OH)-CH(NHC(O)CHF₂)-CH₂F (+/−) |
| 53 | 4-(thiophen-2-yl)-phenyl-CH(OH)-CH(NHC(O)CHF₂)-CH₂F (+/−) |
| 54 | 4-(pyridin-4-yl)-phenyl-CH(OH)-CH(NHC(O)CHCl₂)-CH₂F (+/−) |
| 55 | 4-(1,3,4-thiadiazol-2-yl)-phenyl-CH(OH)-CH(NHC(O)CHCl₂)-CH₂F (+/−) |
| 56 | 4-(pyridin-4-yl N-oxide)-phenyl-CH(OH)-CH(NHC(O)CHCl₂)-CH₂F (+/−) |
| 57 | 4-(pyridin-4-yl)-phenyl-CH(OH)-CH(NHC(O)CHF₂)-CH₂F (+/−) |
| 58 | 4-(pyridin-3-yl N-oxide)-phenyl-CH(OH)-CH(NHC(O)CHCl₂)-CH₂F (+/−) |
| 59 | 4-(pyridin-4-yl)-phenyl-CH(OH)-CH(NHC(O)CHCl₂)-CH₂F (+/−) |
| 60 | 4-(pyridin-4-yl N-oxide)-phenyl-CH(OH)-CH(NHC(O)CHCl₂)-CH₂F (+/−) |
| 61 | 4'-(methylsulfonyl)-biphenyl-CH(OH)-CH(NHC(O)CHCl₂)-CH₂F |

TABLE 1-continued
| Compound # | Structure |
|---|---|
| 62 | 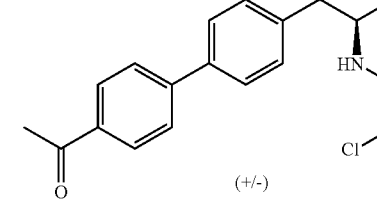 |
| 63 | 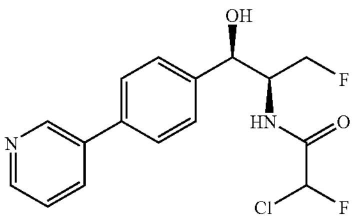 |
| 64 | 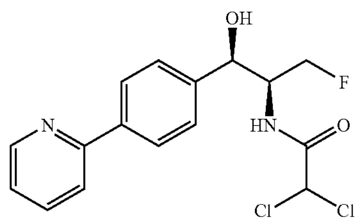 |
| 65 | 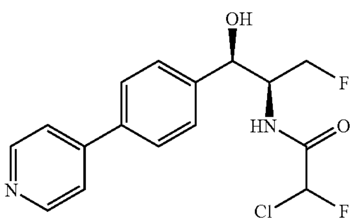 |
| 66 | 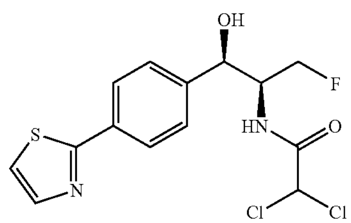 |
| 67 | 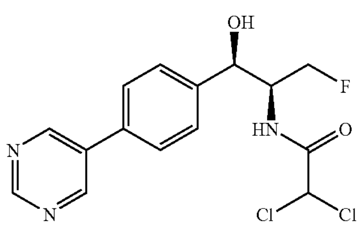 |
| 68 | 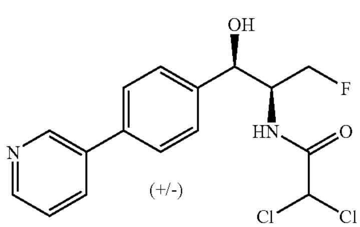 |
| 69 | 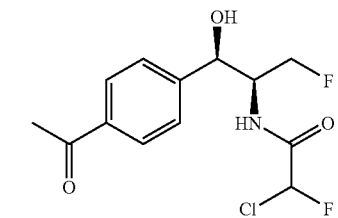 |
| 71 | |
| 72 | |
| 73 | |
| 74 | |
| 75 | |

TABLE 1-continued

| Compound # | Structure |
|---|---|
| 76 | (+/-) |
| 77 | (+/-) |
| 78 | 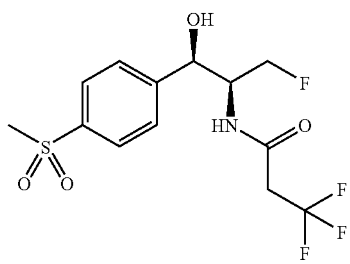 |
| 79 | 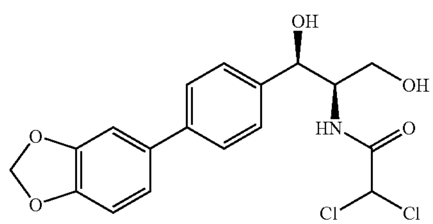 |
| 80 | 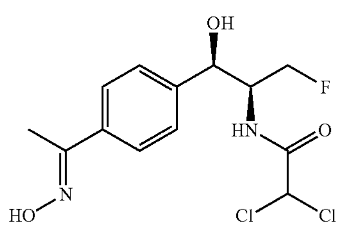 |
| 81 | 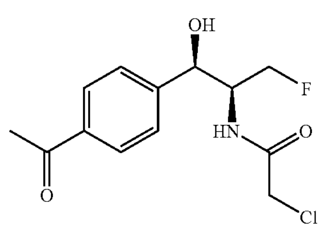 |
| 82 | (+/-) |
| 84 | (+/-) |
| 85 | (+/-) |
| 86 | (+/-) |
| 91 | (+/-) |
| 92 | (+/-) |

TABLE 1-continued
| Compound # | Structure |
|---|---|
| 93 | 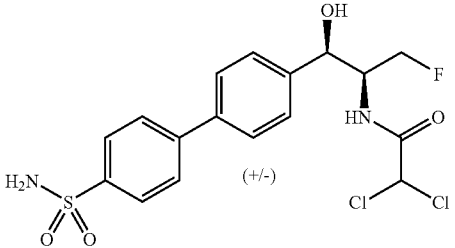 (+/-) |
| 94 | 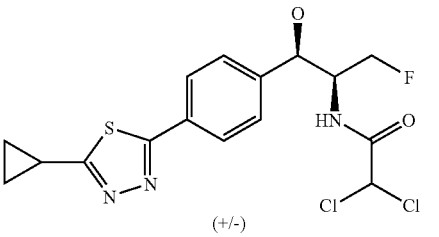 (+/-) |
| 95 | 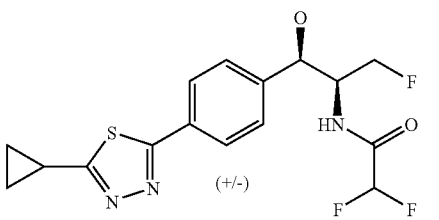 (+/-) |
| 97 | 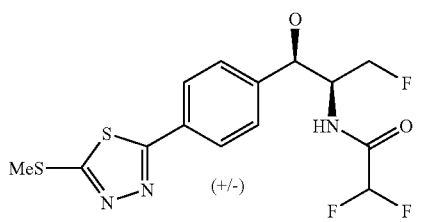 (+/-) |
| 98 | 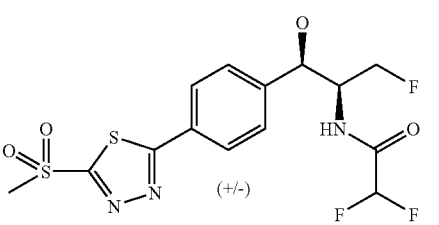 (+/-) |
| 100 | 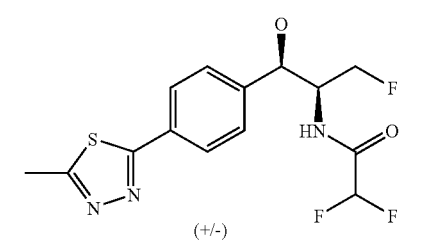 (+/-) |
| 101 | 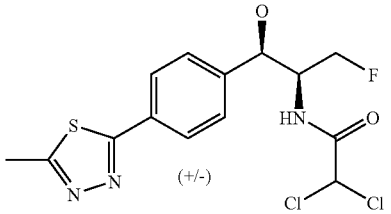 (+/-) |
| 106 | 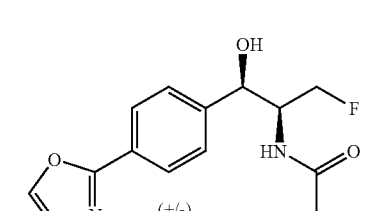 (+/-) |
| 107 | 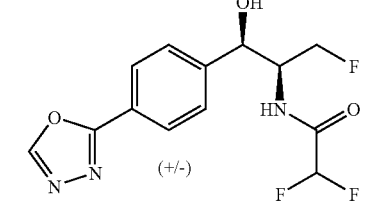 (+/-) |
| 109 | 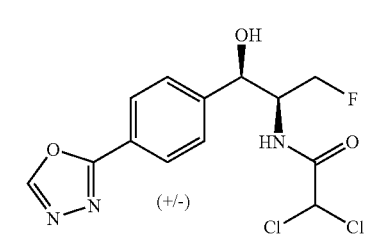 (+/-) |
| 110 | 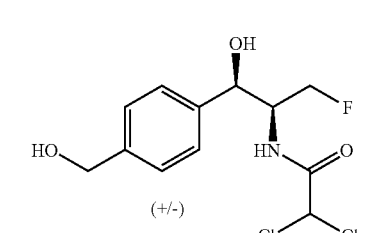 (+/-) |
| 111 | 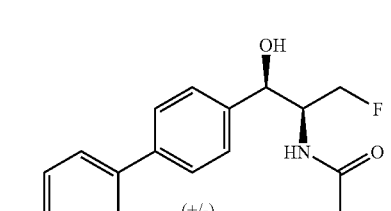 (+/-) |

TABLE 1-continued

| Compound # | Structure |
|---|---|
| 112 | (structure with 2-methylpyridine N-oxide, phenyl, CH(OH)-CH(NHC(O)CHCl₂)-CH₂F, (+/−)) |
| 113 | (structure with 2-methylpyridine N-oxide, phenyl, CH(OH)-CH(NHC(O)CHF₂)-CH₂F, (+/−)) |
| 114 | (structure with pyrimidin-5-yl, phenyl, CH(OH)-CH(NHC(O)CHF₂)-CH₂F, (+/−)) |
| 115 | (structure with 2-acetamido-1,3,4-thiadiazol-5-yl, phenyl, CH(OH)-CH(NHC(O)CHCl₂)-CH₂F, (+/−)) |
| 116 | (structure with pyridin-3-yl, 2-fluorophenyl, CH(OH)-CH(NHC(O)CHF₂)-CH₂F, (+/−)) |
| 117 | (structure with pyridin-3-yl, 2-fluorophenyl, CH(OH)-CH(NHC(O)CHCl₂)-CH₂F, (+/−)) |
| 118 | (structure with thiazol-5-yl, phenyl, CH(OH)-CH(NHC(O)CHF₂)-CH₂F, (+/−)) |
| 120 | (structure with thiazol-5-yl, phenyl, CH(OH)-CH(NHC(O)CHCl₂)-CH₂F, (+/−)) |
| 121 | (structure with 6-methylpyridazin-3-yl, phenyl, CH(OH)-CH(NHC(O)CHCl₂)-CH₂F, (+/−)) |
| 122 | (structure with 6-methylpyridazin-3-yl, phenyl, CH(OH)-CH(NHC(O)CHF₂)-CH₂F, (+/−)) |
| 123 | (structure with 6-cyanopyridin-3-yl, phenyl, CH(OH)-CH(NHC(O)CHCl₂)-CH₂F, (+/−)) |
| 124 | (structure with 6-cyanopyridin-3-yl, phenyl, CH(OH)-CH(NHC(O)CHF₂)-CH₂F, (+/−)) |
| 125 | (structure with 6-chloropyridazin-3-yl, phenyl, CH(OH)-CH(NHC(O)CHCl₂)-CH₂F, (+/−)) |

TABLE 1-continued

| Compound # | Structure |
|---|---|
| 126 | 4-(1,2,4-thiadiazol-5-yl)phenyl CH(OH)-CH(NHC(O)CHCl₂)-CH₂F (+/-) |
| 127 | 4-(pyridazin-3-yl)phenyl CH(OH)-CH(NHC(O)CHF₂)-CH₂F (+/-) |
| 128 | 4-(pyridazin-3-yl)phenyl CH(OH)-CH(NHC(O)CHCl₂)-CH₂F (+/-) |
| 129 | 4-(pyridazin-4-yl)phenyl CH(OH)-CH(NHC(O)CHCl₂)-CH₂F (+/-) |
| 130 | 4-(pyridazin-4-yl)phenyl CH(OH)-CH(NHC(O)CHF₂)-CH₂F (+/-) |
| 131 | 4-(isoxazol-5-yl)phenyl CH(OH)-CH(NHC(O)CHCl₂)-CH₂F (+/-) |
| 132 | 4-(isoxazol-5-yl)phenyl CH(OH)-CH(NHC(O)CHF₂)-CH₂F (+/-) |
| 133 | 4-(2-amino-thiazol-5-yl)phenyl CH(OH)-CH(NHC(O)CHCl₂)-CH₂F (+/-) |
| 134 | 4-(2-amino-thiazol-5-yl)phenyl CH(OH)-CH(NHC(O)CHF₂)-CH₂F (+/-) |
| 135 | 4-(isoxazol-5-yl)phenyl CH(OH)-CH(NHC(O)CHFCl)-CH₂F (+/-) |
| 136 | 4-(isothiazol-5-yl)phenyl CH(OH)-CH(NHC(O)CHCl₂)-CH₂F (+/-) |
| 137 | 4-(isothiazol-5-yl)phenyl CH(OH)-CH(NHC(O)CHF₂)-CH₂F (+/-) |
| 138 | 4-(isothiazol-5-yl)phenyl CH(OH)-CH(NHC(O)CHFCl)-CH₂F (+/-) |

TABLE 1-continued

| Compound # | Structure |
|---|---|
| 139 | (structure with thiazole-phenyl, OH, CHF, NHC(O)CHF₂) (+/−) |
| 140 | (structure with thiadiazole-phenyl, OH, CHF, NHC(O)CHFCl) (+/−) |
| 141 | (structure with 3-amino-isoxazole-phenyl, OH, CHF, NHC(O)CHF₂) (+/−) |
| 142 | (structure with 3-amino-isoxazole-phenyl, OH, CHF, NHC(O)CHCl₂) (+/−) |
| 143 | (structure with 6-cyanopyridine-phenyl, OH, CHF, NHC(O)CHF₂) |
| 144 | (structure with 6-cyanopyridine-phenyl, OH, CHF, NHC(O)CHCl₂) |
| 145 | (structure with 1-hydroxyethyl-phenyl, OH, CHF, NHC(O)CHCl₂) (+/−) |
| 146 | (structure with 3-methoxy-isoxazole-phenyl, OH, CHF, NHC(O)CHCl₂) (+/−) |
| 147 | (structure with thiadiazole-phenyl, OH, CHF, NHC(O)CHCl₂) |
| 148 | (structure with 3-carboxamide-isoxazole-phenyl, OH, CHF, NHC(O)CHF₂) (+/−) |
| 149 | (structure with isoxazole-phenyl, OH, CHF, NHC(O)CHCl₂) |
| 150 | (structure with 3-hydroxymethyl-isoxazole-phenyl, OH, CHF, NHC(O)CHCl₂) (+/−) |

TABLE 1-continued

| Compound # | Structure |
|---|---|
| 151 | 3-(hydroxymethyl)isoxazol-5-yl phenyl derivative with CHF2 acyl group (+/−) |
| 152 | 3-carboxamide-isoxazol-5-yl phenyl derivative with CHCl2 acyl group (+/−) |
| 153 | pyridin-3-yl phenyl derivative with CH2CN acyl group (+/−) |
| 154 | pyridin-3-yl phenyl derivative with CH2N3 acyl group (+/−) |
| 155 | 3-methylisoxazol-5-yl phenyl derivative with CHF2 acyl group (+/−) |
| 156 | 3-methylisoxazol-5-yl phenyl derivative with CHCl2 acyl group (+/−) |
| 157 | 4-methylimidazol-1-yl phenyl derivative with CHCl2 acyl group (+/−) |
| 158 | 4-methylimidazol-1-yl phenyl derivative with CHF2 acyl group (+/−) |
| 159 | isoxazol-5-yl phenyl derivative with CHF2 acyl group |
| 160 | 3-aminoisoxazol-5-yl phenyl derivative with CHCl2 acyl group |
| 161 | 3-methylisoxazol-5-yl phenyl derivative with CHCl2 acyl group |
| 162 | 3-methylisoxazol-5-yl phenyl derivative with CHF2 acyl group |

TABLE 1-continued

| Compound # | Structure |
|---|---|
| 163 | (structure) |
| 164 | (structure) |
| 165 | (structure) |
| 166 | (structure) |
| 167 | (structure) |
| 168 | (structure) |
| 169 | (structure) |
| 170 | (structure) |
| 171 | (structure) |
| 172 | (structure) |
| 173 | (structure) |

TABLE 1-continued

| Compound # | Structure |
|---|---|
| 174 | 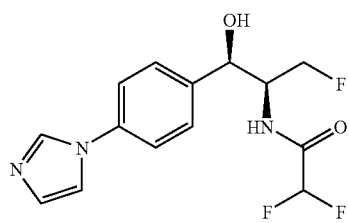 |
| 175 | 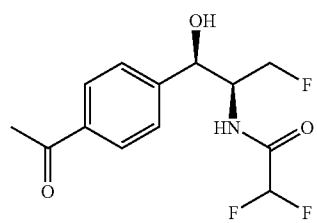 |
| 176 | 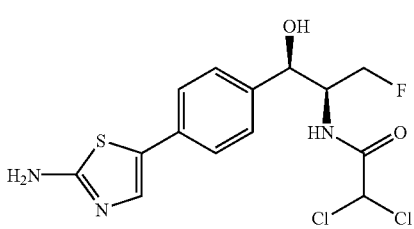 |
| 177 | 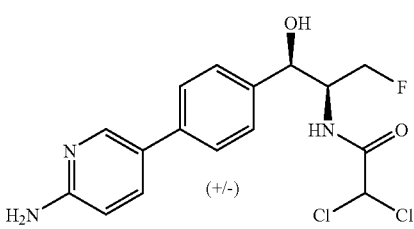 |
| 178 | 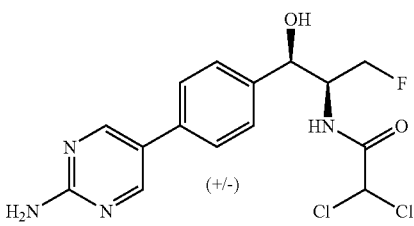 |
| 179 | 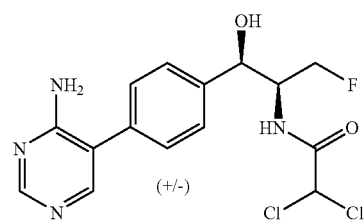 |
| 180 | 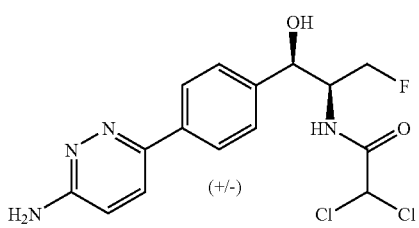 |

Syntheses

Intermediates were prepared in enantiomerically pure form, starting with commercially available chloramphenicol base (1), or as racemic mixtures by condensation of p-bromobenzaldehyde with glycine under basic conditions. For the enantiomerically pure synthesis of intermediates such as 9, chloramphenicol base was converted to compound 3 (Rebstock, M. C., et al., *J. Am, Chem. Soc.*, 1949, 71, 2458; Evans, D. D., et al., *J. Chem. Soc.*, 1954, 1687; Morris, D. S. and Smith, S. D., *J. Chem. Soc.*, 1954, 1680). Compound 3 was subjected to the Sandmeyer reaction after which the acetate protecting group was removed under acidic conditions to provide enantiomerically pure 9.

Alternatively, p-bromobenzaldehyde (5) can be converted to (d/l)-threo-p-bromophenylglycine (6, Scheme 1), (Bolhoffer, W. A. *J. Am. Chem. Soc.* 1954, 76, 1322; Herbert, R. B.; Wilkinson, B.; Ellames, G. J. *Can. J. Chem.* 1994, 72, 114), which can be protected as N-Boc derivative 7 and then reduced in two-steps: activation with DCC and N-hydroxysuccinimide followed by treatment with $NaBH_4$ to provide 8. Compound 9 can be isolated as its TFA salt or as the free base. Regioselective introduction of fluoride is accomplished by protecting the amine and benzylic hydroxyl group as phenyl oxazoline 10 followed by fluorination with (diethylamino)sulfur trifluoride (DAST) or [bis(2-methoxyethyl)amino]sulfur trifluoride (Lal, G. S., *J. Org. Chem.*, 1999, 64, 7048) to give 11. Compound 11 is used in the Suzuki cross-coupling reaction for the synthesis of biaryl derivatives. The other Suzuki partner, an aryl boronic acid such as 12, can be prepared as shown and reacted with aryl halides.

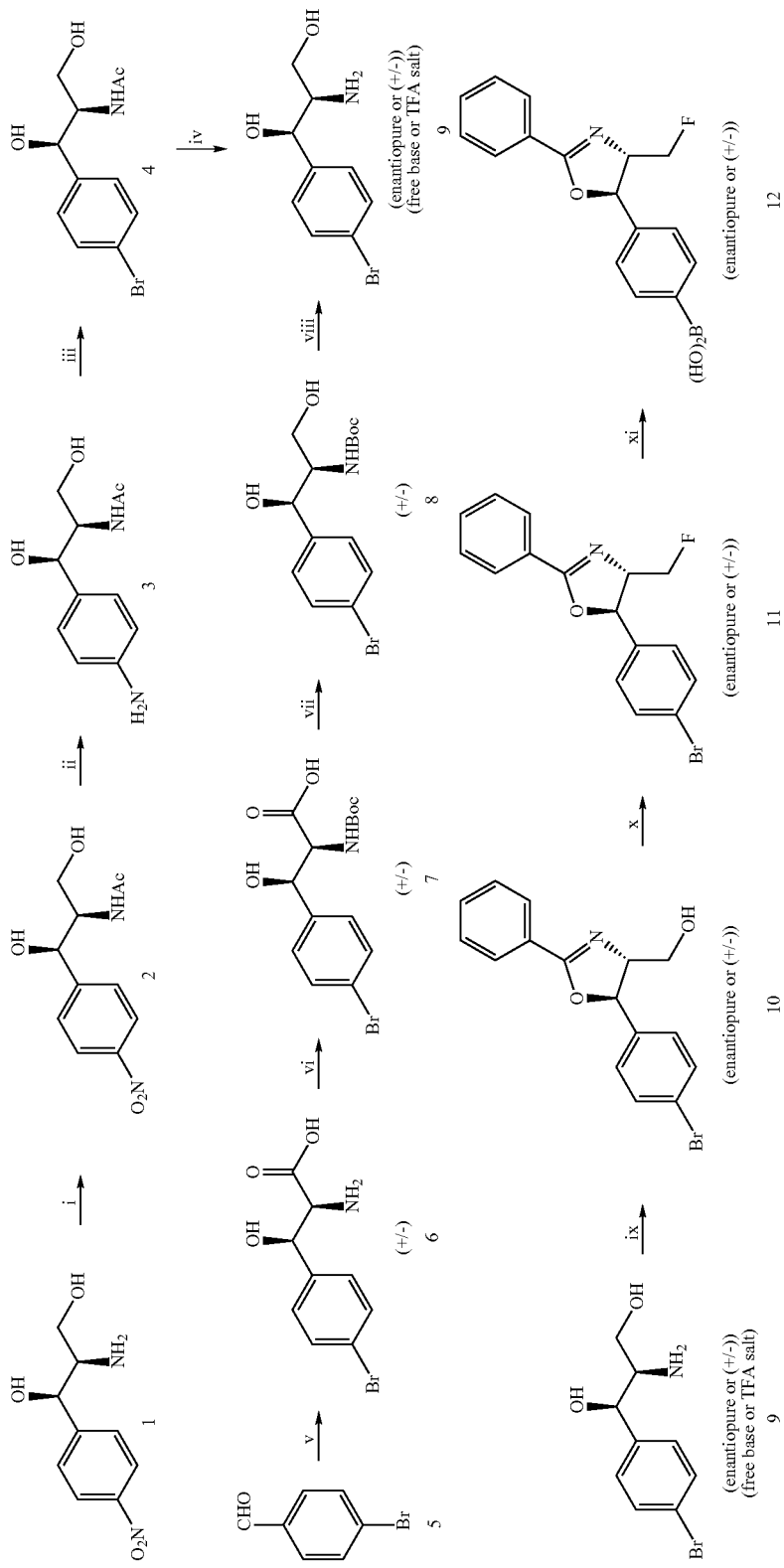

The conditions for removal of the phenyloxazoline protecting group proved to be incompatible with many functional groups at the p-position of the aromatic ring. Thus, a new protecting group motif was developed based on literature methods (Scheme 2; Jommi, G., et al., *Gazz. Chim. Ital.,* 1986, 116:485). Phenylserine 6 was converted to methyl ester 13, which was protected as oxazolidinone 14, which, in turn, was reduced with NaBH$_4$ to 15. Fluorination with either DAST or [bis(2-methoxyethyl)amino]sulfur trifluoride gave intermediate 16, which did not give consistently good Suzuki reaction yields. Thus, 16 was converted to 17. Cleavage of the oxazolidinone protecting group was facilitated by the introduction of a Boc group (Grehn, L., et al., *Acta Chem. Scand. B,* 1986, 40, 745) followed by base-catalyzed cleavage to give 18 (Ishizuka, T. and Kunieda, T., *Tetrahedron Lett.,* 1987, 28, 4185; Jommi, G., et al., *Gazz. Chim. Ital.,* 1988, 118:75).

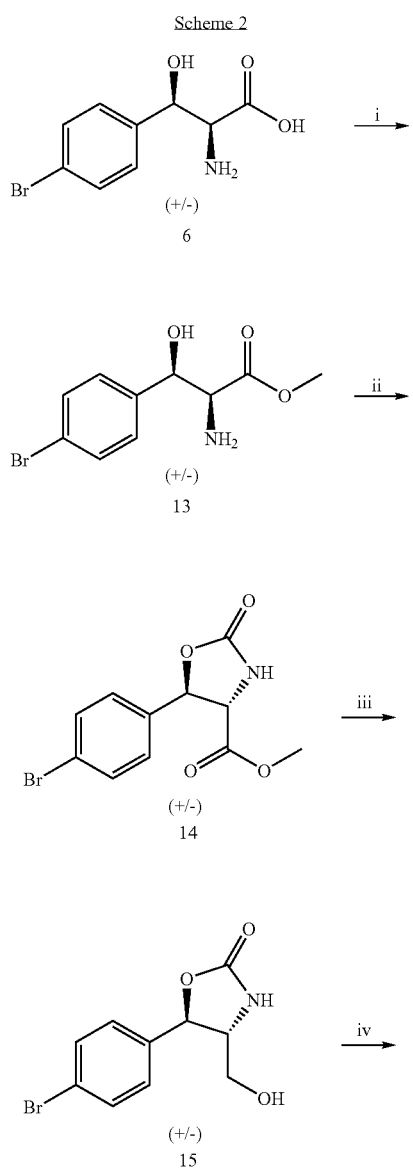

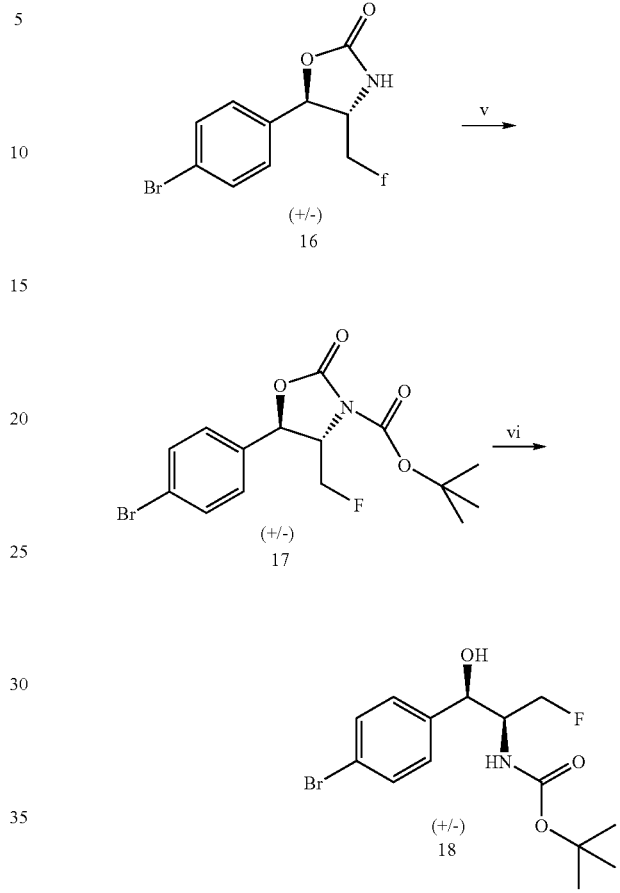

i) HCl, MeOH 0° C. to room temperature 18 h, then reflux 18 h;
ii) CDI, Et$_3$N, THF/1,2-dichloroethane;
iii) NaBH$_4$, MeOH 0° C.;
iv) DAST or [bis (2-methoxyethyl) amino] sulfur trifluoride -78° C. 10 min then room temperature until complete;
v) Boc$_2$O, DMAP, MeCN;
vi) Cs$_2$CO$_3$, MeOH.

Compound 18 was protected as isopropylidene derivative 19, which was converted to boronic acid 23 (Scheme 3). Compounds 18, 19, 22 and 23 were used in Suzuki cross-coupling reactions. Compound 23 provided the most versatility since it could be cross-coupled with any aryl bromide or iodide and the protecting groups could be easily removed under mild conditions. Compound 22 was attractive as a Suzuki cross-coupling partner in that the coupling reactions yielded the desired florfenicol analogs directly without the need for deprotection and dihaloacetylation. However, cross-coupling yields with 22 were lower than those with 23. Cross-couplings using 21 gave the desired products contaminated with acetate and monochloroacetate analogs.

Racemic compound 20 was identical spectroscopically to a sample synthesized from semi-synthetic 11 by hydrolytic cleavage and basic work-up. This provided unequivocal proof that the condensation of phenylserine 6 had proceeded with the appropriate relative threo or syn stereoselectivity.

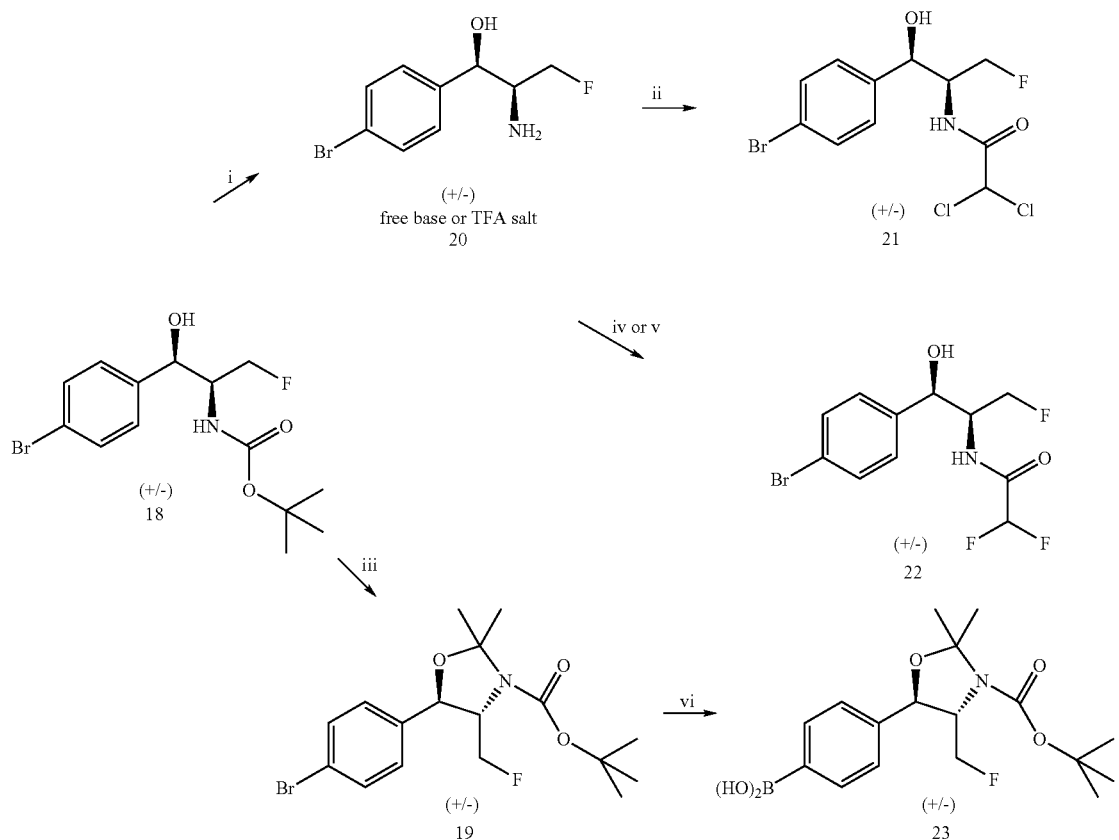

i) 9:1 TFA, H₂O, then NaOH work-up if free-base is desired;
ii) methyl dichloroacetate, Et₃N, MeOH, Δ;
iii) 2-methoxypropene, p-TsOH•H₂O;
iv) methyl difluoroacetate, Et₃N, MeOH, Δ;
v) difluoroacetyl chloride, Et₃N, followed by 1:8:1 Et₃N, MeOH, H₂O;
vi) first n-BuLi at -78° C., then B(OMe)₃, -78° C. to room temperature.

Compounds 11 and 12 were used to prepare compounds 28 and 29 (Scheme 4). Compound 11 was cross-coupled with 3-pyridine boronic acid under standard biphasic Suzuki conditions to yield protected intermediate 26. The N—C cross-coupling product 27 was prepared according to the recently reported methods of Lam and coworkers (Lam, P. Y. S., et al., *Synlett*, 2000, 674; Lam, P. Y. S., *Tetrahedron, Lett.*, 1998, 39, 2941; Lam, P. Y. S., *Tetrahedron Lett.*, 2001, 42, 3415). Both 26 and 27 were deprotected and dichloroacetylated to give 28 and 29.

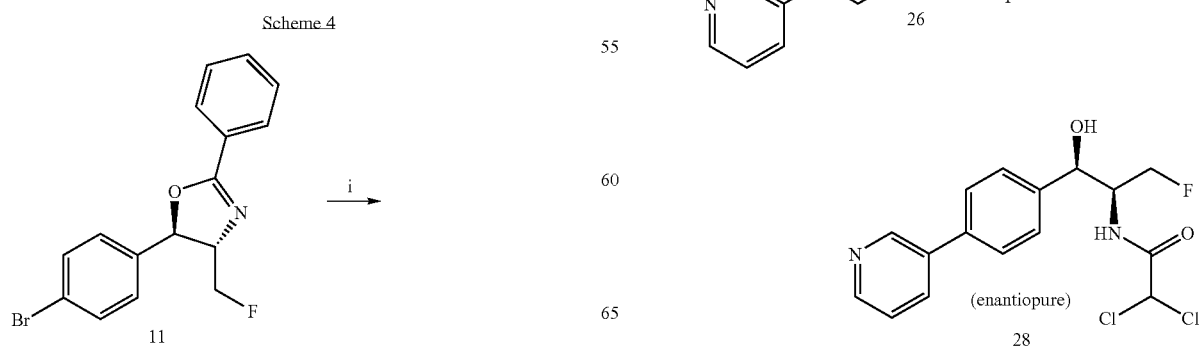

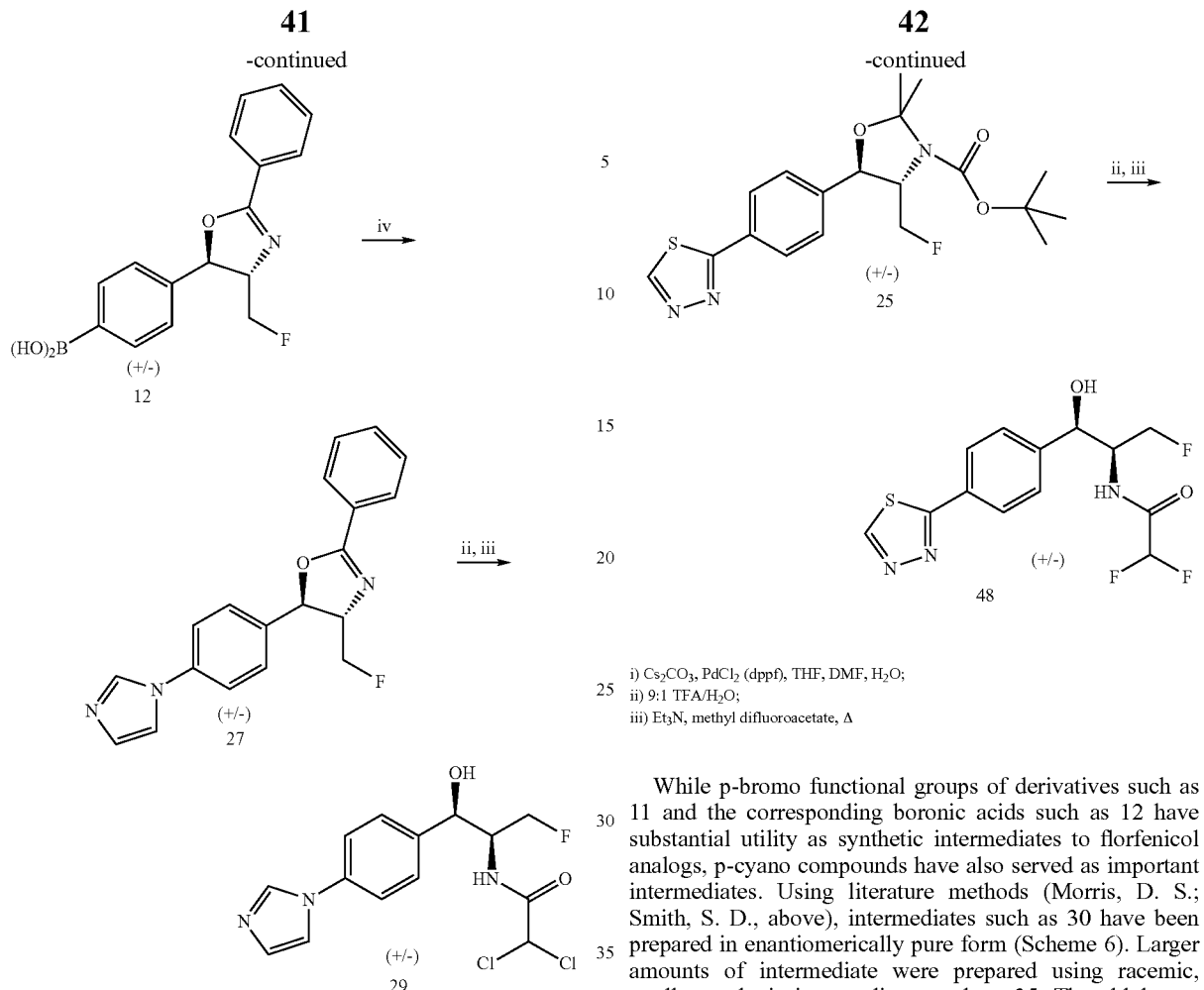

i) Cs$_2$CO$_3$, PdCl$_2$ (dppf), THF, DMF, H$_2$O;
ii) 9:1 TFA/H$_2$O;
iii) Et$_3$N, methyl difluoroacetate, Δ

While p-bromo functional groups of derivatives such as 11 and the corresponding boronic acids such as 12 have substantial utility as synthetic intermediates to florfenicol analogs, p-cyano compounds have also served as important intermediates. Using literature methods (Morris, D. S.; Smith, S. D., above), intermediates such as 30 have been prepared in enantiomerically pure form (Scheme 6). Larger amounts of intermediate were prepared using racemic, totally synthetic intermediates such as 35. The aldol condensation used to produce 32 from p-cyanobenzaldehyde and glycine methyl ester was adapted from the literature (Pines, S. H. and Kazlowski, M. A., *J. Org. Chem.*, 1972, 37, 292).

i) m-pyridine boronic acid, Na$_2$CO$_3$, Pd(PPh$_3$)$_4$, THF, H$_2$O, Δ;
ii) 6 N aqueous HCl, sealed tube 100° C. then basic work-up;
iii) methyl dichloroacetate, Et$_3$N, MeOH, Δ;
iv) Cu (OAc)$_2$, pyr., CH$_2$Cl$_2$, room temperature, open to air, 40 h.

Compound 23 and 2-bromo-1,3,4-thiadiazole (24) were reacted to give 48 (Scheme 5). Suzuki cross-coupling produced the heterobiaryl 25. Compound 25 was deprotected with 9:1 TFA/H$_2$O, which removed the Boc and isopropylidene groups simultaneously, and then was difluoroacetyated to give 48.

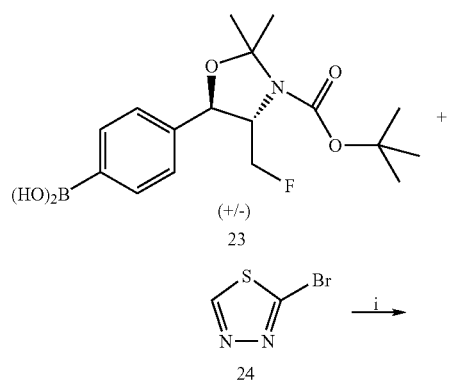

Scheme 5

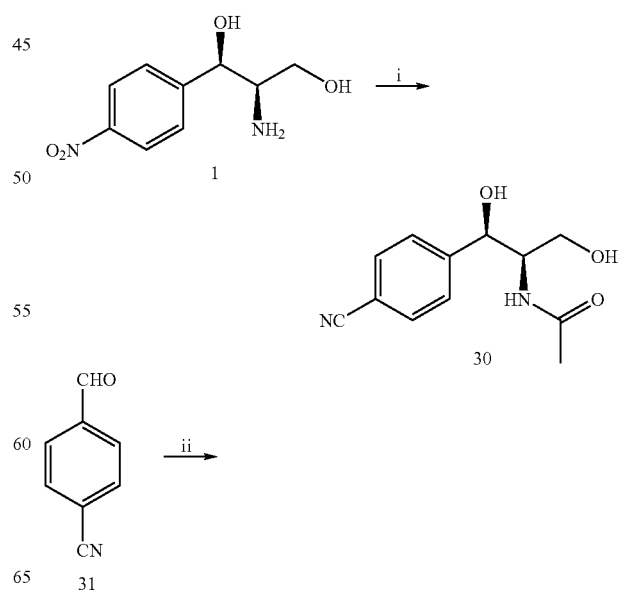

Scheme 6

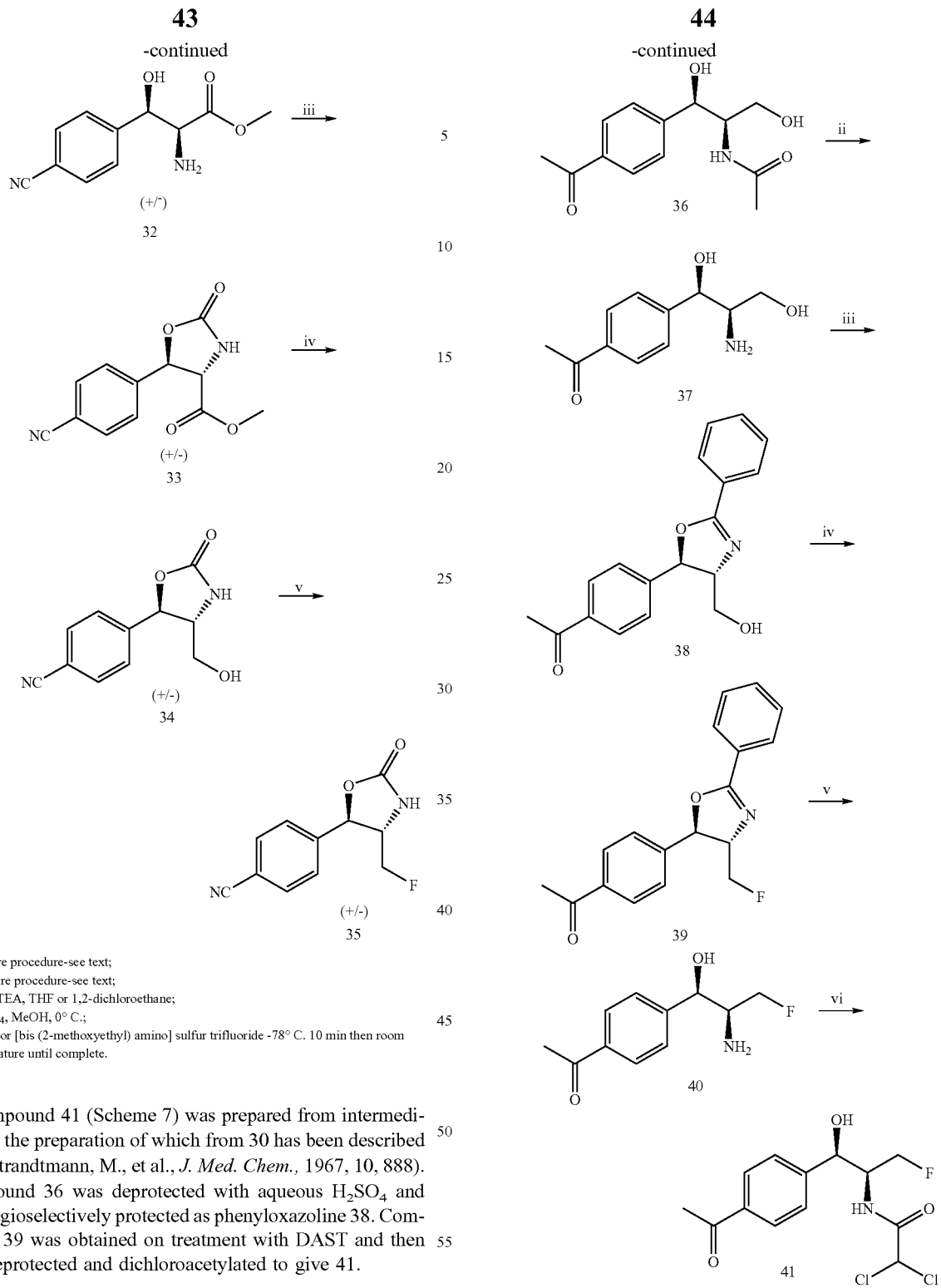

i) literature procedure-see text;
ii) literature procedure-see text;
iii) CDI, TEA, THF or 1,2-dichloroethane;
iv) NaBH₄, MeOH, 0° C.;
v) DAST or [bis (2-methoxyethyl) amino] sulfur trifluoride -78° C. 10 min then room temperature until complete.

Compound 41 (Scheme 7) was prepared from intermediate 36, the preparation of which from 30 has been described (von Strandtmann, M., et al., *J. Med. Chem.*, 1967, 10, 888). Compound 36 was deprotected with aqueous H₂SO₄ and then regioselectively protected as phenyloxazoline 38. Compound 39 was obtained on treatment with DAST and then was deprotected and dichloroacetylated to give 41.

Scheme 7

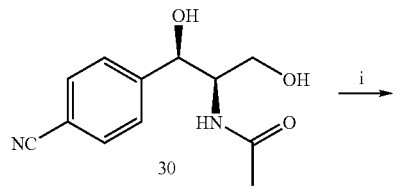

i) MeLi, THF, then H₂O;
ii) 10% aqueous H₂SO₄, Δ;
iii) Et₃N, ethyl benzimidatehydrochloride, Δ;
iv) DAST -78° C. room temperature;
v) 6N HCl, Δ;
vi) methyldichloroacetate, Et₃N, MeOH, Δ.

Compound 47 was prepared from intermediate 35 by treatment with hydroxylamine hydrochloride followed by triethyl orthoformate to give 43, which was deprotected to give 46, which was then dichloroacetylated.

Scheme 8 i) NH₂OH·HCl, EtOH, Δ;
ii) triethyl orthoformate, Δ;
iii) Boc₂O, DMAP, MeCN;
iv) Cs₂CO₃, MeOH;
v) TFA/H₂O 9:1;
vi) methyldichloroacetate, Et₃N, Δ.

p-Acyl derivatives were obtained by Stille coupling reactions of the protected intermediates (Scheme 9, compounds 87 and 88) with acid chlorides. Trimethylstannyl groups were introduced by Pd-mediated reactions using hexamethylditin.

Scheme 9 i) Me₃SnSnMe₃, Pd(PPh₃)₄, Δ, C₆H₆ or PhMe

The cyclobutyl derivative 73 was prepared from 87 via a Stille coupling reaction that produced intermediate 89

(Scheme 10) which was deprotected and dichloro-acetylated.

Attempted deprotection of the cyclopropyl derivative corresponding to 89 led to HCl-mediated ring opening. Thus, to prepare 91, the boc/isopropylidene approach was employed since deprotection occurs under conditions that do not affect the cyclopropyl group.

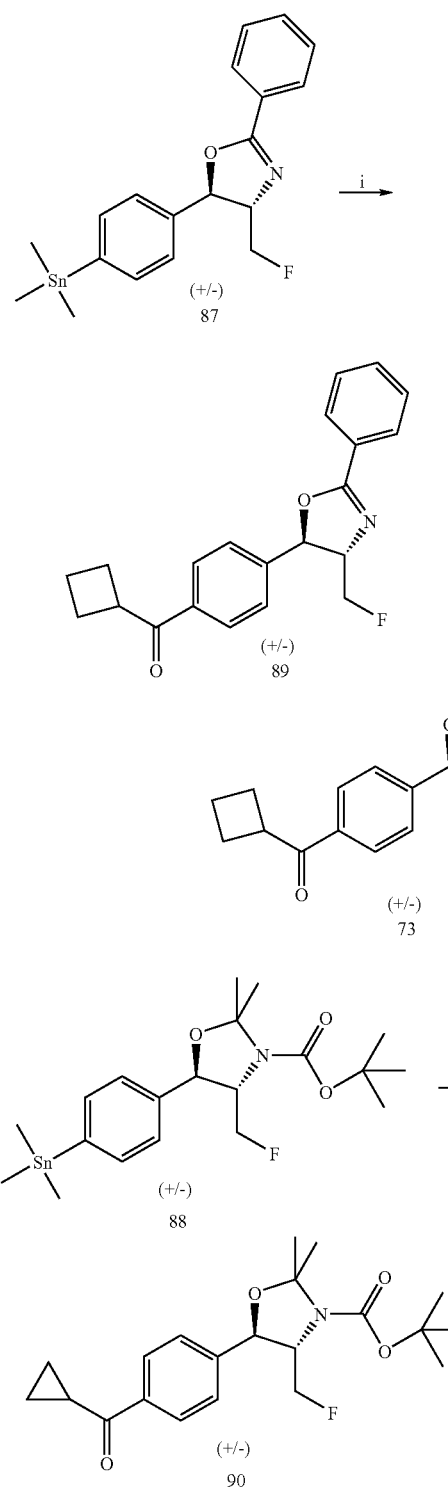

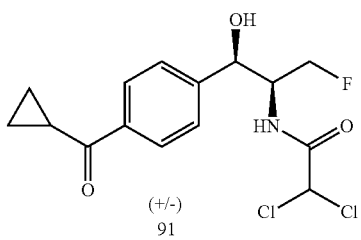

i) Pd$_2$dba$_3$, K$_2$CO$_3$, Et$_3$N, cyclobutanecarbonyl chloride, room temperature, 3h;
ii) 6N HCl sealed tube, Δ;
iii) methyldichloroacetate, Et$_3$N, MeOH, Δ;
iv) Pd$_2$dba$_3$, K$_2$CO$_3$, Et$_3$N, cyclopropanecarbonyl chloride, room temperature, 3h;
v) TFA/H$_2$O When required, p-carboxyphenyl derivatives of protected phenicol intermediates could be prepared in two ways. For example, hydrolysis of the p-nitrile analog of 17 gives the corresponding carboxylic acid. However, nitriles generally could not be obtained as readily as the bromo derivatives. Thus, the preferred approach to carboxylation was replacement of the bromo group. For example, carboxylic acid derivative 102 (Scheme 11) was prepared by lithiation of 17 followed by treatment with CO$_2$ and acid work-up. Compound 102 was converted to methyl ester 103, which was reacted with hydrazine to give 104. Cyclization of 104 with triethyl orthoformate gave oxadiazole 105, which was deprotected and dihaloacetylated to give 106 and 107.

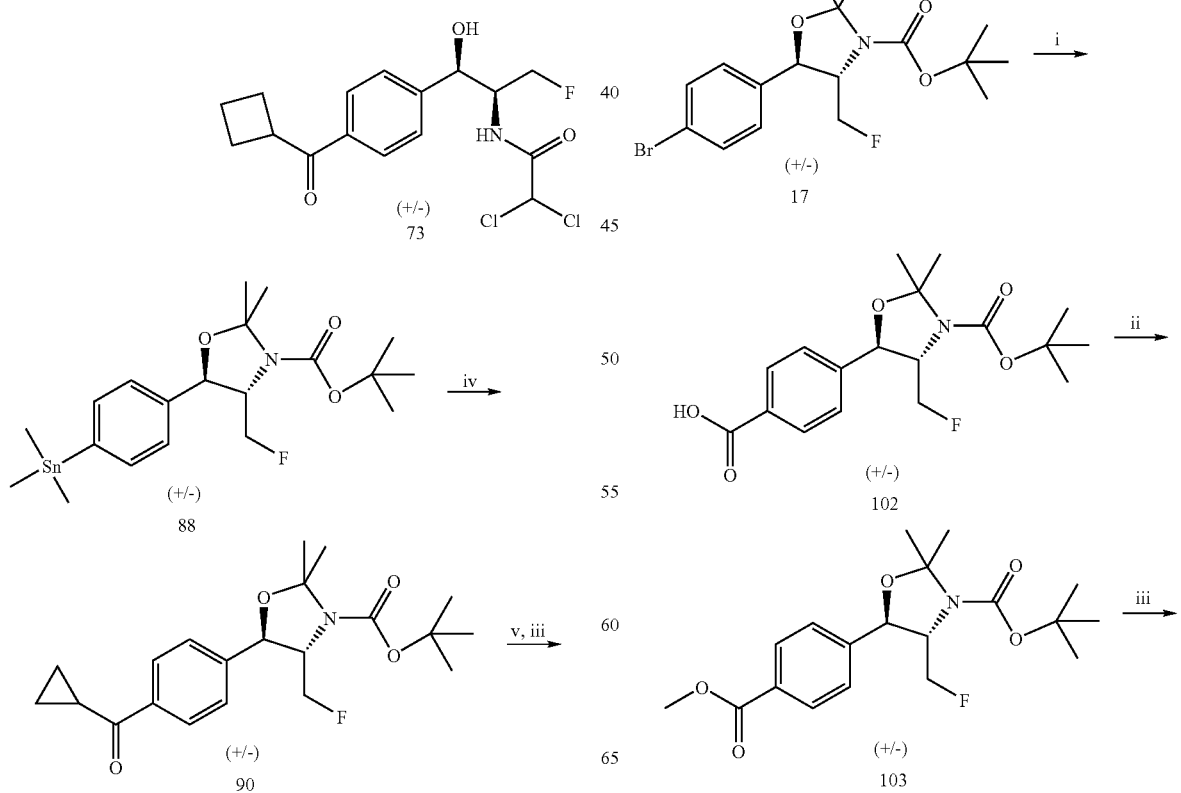

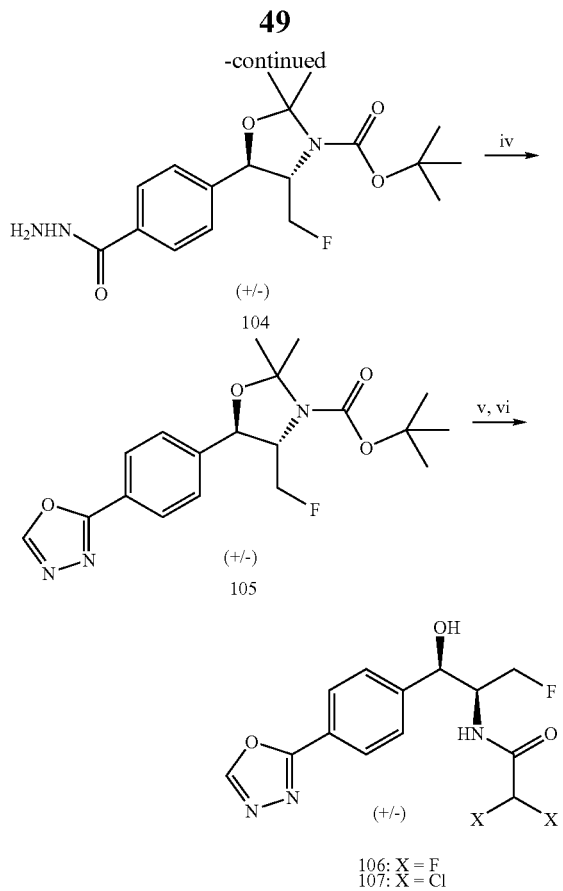

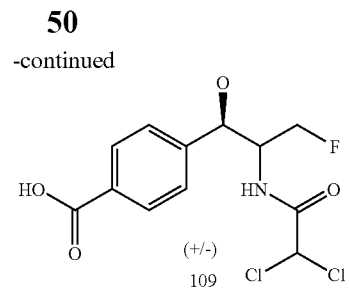

i) DCC, pentafluorophenol, EtOAc;
ii) NaBH₄, MeOH;
iii) TFA/H₂O;
iv) methyl dichloroacetate, Et₃N, Δ.

106: X = F
107: X = Cl i) n-BuLi, -78° C., THF, then bubble dry CO₂ then warm to room temperature, then H₃O⁺; CH₂N₂;
iii) hydrazine, EtOH, Δ;
iv) triethylorthoformate, Δ;
v) TFA/H₂O;
vi) for 106 Et₃N, ethyldifluoroacetate, room temperature; for 107 same as 106, but replace ethyl difluoroacetate with methyl dichloroacetate.

The carboxylic acid derivative of 102 was also used to prepare compounds such as 109 (Scheme 12), by reduction to alcohol 108 followed by deprotection and dichloroacetylation Scheme 12

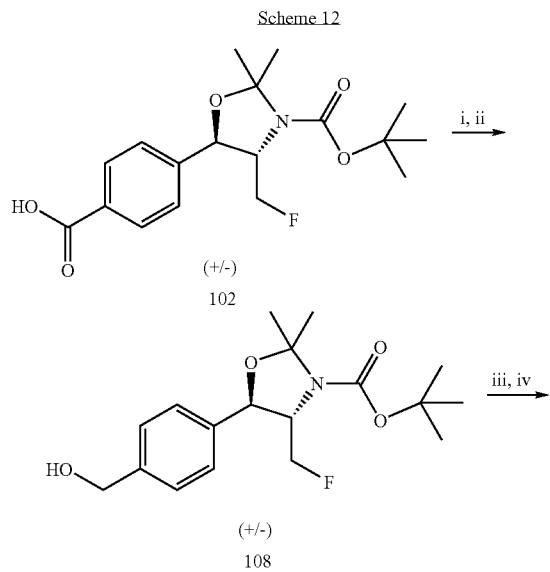

Biological Evaluation

All of the compounds of this invention are expected to demonstrate antimicrobial activity against the same bacteria as the other members of the chloramphenicol family. In addition, they may be expected to be active against species of bacteria that are resistant to current chloramphenicol antibiotics, in particular florfenicol. It is also expected that the present compounds may exhibit activity against genera and species of bacteria against which current chloramphenicol-type antibiotics are not active.

It is also understood that, with regard to bioactivity, one enantiomer of a compound may be more active than the other. In such case, whether expressly stated or not, the more active isomer is considered the preferred embodiment of this invention. Particularly preferred is the most active enantiomer of the 1-(R)-2(S) absolute configuration of any compound herein.

To determine the range and level of activity of the compounds of this invention, the following protocols may be used. Other such protocols will become apparent to those skilled in the art based on the disclosures herein and are within the scope of this invention. Some compounds herein are expected to not only exhibit substantial antibacterial activity but to also be less susceptible to current chloramphenicol resistance mechanisms. The screening protocols herein may be used to determine such characteristics also.

Susceptibility Testing

Compounds were evaluated against a panel of bacterial strains using a broth microdilution assay performed as recommended by the NCCLS (National Committee for Clinical Laboratory Standards (NCCLS) 2000, Methods for Dilution of Antimicrobial Susceptibility Tests for Bacteria That Grow Aerobically—Fifth Edition, Approved Standard, NCCLS Document M7-A5, Vol 20, No. 2). The minimum inhibitory concentration (MIC) is defined as the lowest concentration of a compound that prevents the growth of the bacteria.

The following 10 organisms constituted the primary panel of evaluation:

TABLE 2

| Bacteria | Strain | Efflux Pump | Phenotype |
|---|---|---|---|
| Escherichia coli | ECM 1194 | AcrAB[a] | Wild type |
| Escherichia coli | ECM 1694 | None | ΔacrAB::Tn903kmr |
| Escherichia coli | ECM 1642 | AcrAB | MarR |
| Escherichia coli | ECM 1888 | MdfA | tolC::Tn mdfR |
| Escherichia coli | ECM 1750 | CmlA | ΔacrAB::Tn903kmr/pLQ821 |
| Escherichia coli | ECM 1958 | Flo | ΔacrAB::Tn903kmr/p1956 |
| Escherichia coli | ECM 1970 | AcrAB + Flo | marR/p1956 |

TABLE 2-continued

| Bacteria | Strain | Efflux Pump | Phenotype |
|---|---|---|---|
| *Escherichia coli* | ECM 1197 or ECM 2024 | AcrAB[a] AcrAB[a] | EMR::Cm (cat) ECM1197 acrAB::Kan |
| *Pasteurella multocida* | ATCC43134 | | Wild type |
| *Mannhemia haemolytica* | ATCC33396 | | Wild type |

[a]AcrAB efflux pump expressed at a low level

Assays were performed in Cation-Adjusted Mueller-Hinton Broth (CAMHB) at a bacterial inoculum of $5\times10^5$ CFU/ml and a final volume of 100 µl. Florfenicol and chloramphenicol controls and test compounds were prepared at four times the desired final concentration. Dilution to the desired concentration was accomplished directly on the plates by serial 2-fold dilution using a multi-channel pipette. After dilution, 25 µl of CAMHB was added to each well.

The bacterial inocula were prepared as follows. For each strain, one isolated colony was used to inoculate a volume of 5 ml of CAMHB. The cultures were incubated overnight (20 hours) at 35° C. in a shaking incubator. They were then diluted in sterile saline to a density equivalent to a 0.5 McFarland suspension (approx. $10^8$ CFU/ml). The suspensions were further diluted in CAMHB to approximately $5\times10^5$ CFU/ml. A volume of 50 µl of the inoculum was added to each well. Positive and negative growth controls were included on each plate. The original inocula were determined by applying 10 µl of several 10-fold dilutions on TSA plates. Agar plates were incubated overnight at 35° C. and colony-forming units (CFU) counted. Microtiter plates were incubated for 20 hours at 35° C. and were read using a microtiterplate reader (Molecular Devices) at 650 nm and by visual observation using a microtiterplate reading mirror to determine the MIC.

Pharmaceutical Compositions

A compound of the present invention, a prodrug thereof or a physiologically acceptable salt of either the compound or its prodrug, can be administered as such to a patient or can be administered in pharmaceutical compositions in which the foregoing materials are mixed with suitable excipient(s). Techniques for formulation and administration of drugs may be found in *Remington's Pharmacological Sciences*, Mack Publishing Co., Easton, Pa., latest edition. The formulations and techniques discussed in Remington relate primarily to use with human patients; however, they may readily modified for use with non-human patients by techniques well-known to those skilled in the veterinary art.

Routes of Administration

As used herein, "administer" or "administration" refers to the delivery of a compound, salt or prodrug of the present invention or of a pharmaceutical composition containing a compound, salt or prodrug of this invention to an organism for the purpose of treating or preventing a microbial infection.

Suitable routes of administration may include, without limitation, oral, rectal, transmucosal, intramuscular, subcutaneous, intramedullary, intrathecal, direct intraventricular, intravenous, intravitreal, intraperitoneal, intranasal, aural or intraocular. The preferred routes of administration are oral and parenteral.

Alternatively, one may administer the compound in a local rather than systemic manner, for example, by preparation as a salve that is applied directly to the infected area or by injection of the compound directly into infected tissue. In either case, a sustained release formulation may be used.

Composition/Formulation

Pharmaceutical compositions of the present invention may be manufactured by processes well known in the art, e.g., using a variety of well-known mixing, dissolving, granulating, dragee-making, levigating, emulsifying, encapsulating, entrapping or lyophilizing processes. The compositions may be formulated in conjunction with one or more physiologically acceptable carriers comprising excipients and auxiliaries which facilitate processing of the active compounds into preparations which can be used pharmaceutically. Proper formulation is dependent upon the route of administration chosen.

For injection, including, without limitation, intravenous, intramusclular and subcutaneous injection, the compounds of the invention may be formulated in aqueous solutions, preferably in physiologically compatible buffers such as Hanks' solution, Ringer's solution, physiological saline buffer or polar solvents including, without limitation, N-methyl-2-pyrrolidone, 2-pyrrolidone, other pyrrolidones, N,N-dimethylacetamide, N,N-dimethylformamide, dimethylsulfoxide, acetone and glycerol formal. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well-known in the art. Such carriers enable the compounds of the invention to be formulated as tablets, pills, lozenges, dragees, capsules, liquids, gels, syrups, pastes, slurries, solutions, suspensions, concentrated solutions and suspensions for diluting in the drinking water of a patient, premixes for dilution in the feed of a patient, and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropyl-methylcellulose, sodium carboxy-methylcellulose, and/or polyvinylpyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, or liquid polyethylene glycols. Stabilizers may be added in these formulations, also.

For administration by inhalation, the compounds of the present invention can conveniently be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers. Useful compositions include, without limitation, suspensions, solutions or emulsions in oily or aqueous vehicles, and may contain adjuncts such as suspending, stabilizing and/or dispersing agents. Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions. Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, although often at the risk of greater toxicity.

Additionally, the compounds may be delivered using a sustained-release system, such as semi-permeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the particular compound, additional stabilization strategies may be employed.

Pharmaceutical compositions useful herein also may comprise solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Dosage

A therapeutically effective amount refers to an amount of compound effective to prevent, alleviate or ameliorate symptoms of a microbial infection. Determination of a therapeutically effective amount is well within the capability of those skilled in the art, especially in light of the disclosure herein.

For any compound used in the methods of the invention, the therapeutically effective amount can be estimated initially from cell culture assays. Then, the dosage can be formulated for use in animal models so as to achieve a circulating concentration range that includes the MIC as determined in cell culture. Such information can then be used to more accurately determine dosages useful in patients.

Toxicity and therapeutic efficacy of the compounds described herein can be determined by standard pharmaceutical procedures in cell cultures or experimental animals. For example, the MIC and the $LD_{50}$ for a particular compound can be determined by methods well-known in the art. The data obtained can be used to formulat a range of dosages useful in patients. The dosage, of course, may vary depending upon the dosage form and route of administration. The exact formulation, route of administration and dosage can be selected by the individual physician in view of the patient's condition. (See e.g., Fingl, et al., 1975, in "The Pharmacological Basis of Therapeutics", Ch. 1 p.1). In general, however, the presently preferred dosage range for systemic delivery of a compound of this invention will be from about 1 to about 100 mg/Kg. The presently preferred dosage range for topical use will generally be from about 0.1 mg to about 1 gm.

Dosage amount and interval may be adjusted individually to provide plasma levels of the compound that are sufficient to maintain a concentration equal to the MIC or any other desired level. Such plasma levels are often referred to as minimum effective concentrations (MECs). The MEC will vary for each compound but can be estimated from in vitro data, e.g., the concentration necessary to achieve 80+% inhibition of a microbe, may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10–90% of the time, preferably between 30–90% and most preferably between 50–90%.

In cases of local administration or selective uptake, the effective local concentration of the drug may not be related to plasma concentration and other procedures known in the art may be employed to determine the correct dosage amount and interval.

The amount of a composition administered will, of course, be dependent on the patient being treated, the severity of the infection, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition.

EXAMPLES

The following examples are provided to illustrate certain embodiments of this invention and are not intended, nor are they to be construed, to limit its scope in any manner whatsoever.

Starting materials were obtained from commercial suppliers and used without further purification unless otherwise noted. Chemical suppliers included Aldrich, Fluka, and Lancaster. Pd(PPh$_3$)$_4$ was obtained from Lancaster or Strem and immediately transferred into N$_2$ flushed vials (between 10 and 100 mg each) in an N$_2$ glove bag. The vials were wrapped in aluminum foil and stored in N$_2$-flushed, zip-lock baggies at −20° C. PdCl$_2$(dppf) was obtained from Aldrich and used from the bottle. Standard reagent grade solvents, which were not necessarily anhydrous, were used. Anhydrous solvents were purchased from chemical suppliers and used as is.

$^1$H NMR spectra were recorded on a 300 MHz Varian FT-NMR spectrometer and are reported in the format "chemical shift (multiplicity, integration, coupling constant)." Coupling constants are reported in Hz. Mass spectra were obtained-on a Micromass Platform II single quadrupole mass spectrometer equipped with electrospray ionization (ESI).

The following three Suzuki cross-coupling methods were used:

Method A: the aryl boronic acid (0.167 mmol) and aryl bromide (0.334 mmol) were combined in a mixture of aqueous Na$_2$CO$_3$ (3 mL of a 10% (w/w) solution) and THF (5 mL). The mixture was purged briefly with N$_2$. Pd(PPh$_3$)$_4$ (10 mol %, 0.0167 mmol) was added, the mixture purged with N$_2$, and then refluxed for 16 hours. The reaction mixture was diluted with ethyl acetate (EtOAc), washed with a saturated brine solution, dried over anhydrous Na$_2$SO$_4$ and concentrated. The residue was then purified by chromatography.

Method B: the aryl boronic acid (0.301 mmol), the aryl bromide (0.602 mmol), and Cs$_2$CO$_3$ (0.903 mmol) were combined in THF (2.0 mL), DMF (2.0 mL), and H$_2$O (0.5 mL) at room temperature. The mixture was purged with N$_2$ for 5 min and [1,1'-bis(diphenylphosphino)ferrocene] dichloropalladium(II) dichloromethane complex (0.0301 mmol) was added. The mixture was purged with N$_2$ for 5 minutes and then stirred at 55° C. for 16 hours. The mixture was concentrated under vacuum, diluted with EtOAc and washed with brine. The EtOAc was dried over anhydrous Na$_2$SO$_4$ and concentrated. The residue was purified by chromatography.

Method C: the aryl boronic acid (0.934 mmol), the aryl bromide (2.34 mmol), and Cs$_2$CO$_3$ (2.80 mmol) were suspended in a mixture of toluene (4 mL), n-butanol (4 mL), and H$_2$O (2 mL). The mixture was purged at room temperature with N$_2$ after which Pd(PPh$_3$)$_4$ (0.280 mmol) was added. The mixture was purged with N$_2$ for an additional 5 minutes and then heated to 75° C. After 12 hours, the mixture was cooled to room temperature and concentrated under vacuum. The residue was partitioned between H$_2$O (75 mL) and EtOAc (75 mL). The EtOAc layer was washed with brine (2×50 mL), dried over anhydrous Na$_2$SO$_4$, and concentrated under vacuum. The residue was purified by chromatography.

Example 1

Compound 3

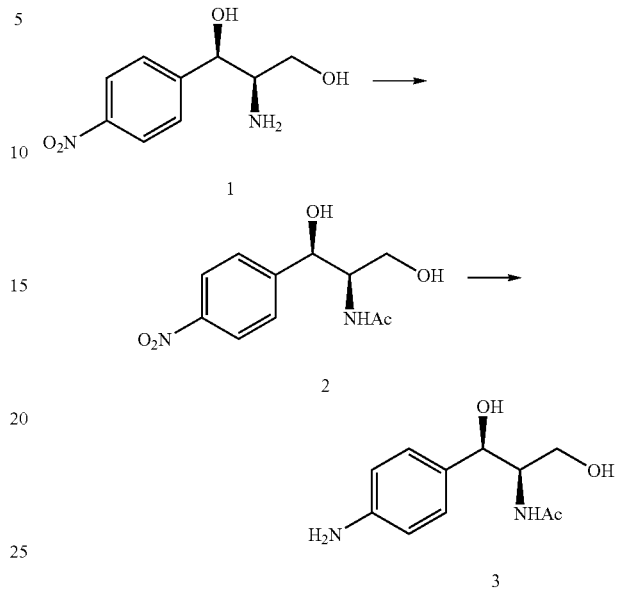

In 80 mL of methanol was dissolved 8.13 g (32.0 mmol) of chloramphenicol base as the N-acetate, prepared by literature methods (Rebstock, M. C., et al., supra, Crooks H. M. et al., supra; Evans, D. D.; Morris, D. S. et al., supra). After purging with N$_2$, Pd/C was added and the mixture was stirred under H$_2$(1 atm) for 16 hours. The Pd/C was then removed by filtration through Celite. The solution was concentrated under vacuum and the residue purified by silica gel chromatography, eluting with 15% MeOH in CH$_2$Cl$_2$ to give 3 (7.13 g, 31.7 mmol). $^1$H NMR (300 MHz, CD$_3$OD): δ 1.92 (s, 3H), 3.40 (dd, 1H, J=11.1, 6.0), 3.61 (dd, 1H, J=11.1, 5.7), 4.01 (m, 1H), 4.73 (d, 1H, J=5.4), 6.69 (d, 2H, J=8.4), 7.11 (d, 2H, J=8.4).

Example 2

Compound 4

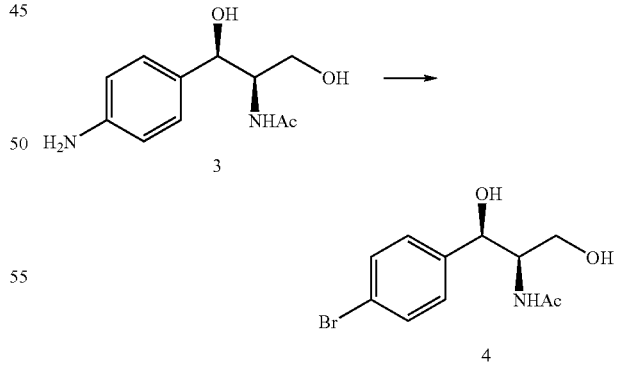

An aqueous solution of NaNO$_2$ (1.27 g, 18.5 mmol, 50 mL H$_2$O) was added dropwise to a solution of 3 (3.76 g, 16.8 mmol) in 35 mL of 48% aqueous HBr at 0° C. After addition was completed, the mixture was stirred for 30 min at 0° C. The mixture was then added dropwise to a solution of CuBr (2.65 g, 18.45 mmol) in 15 mL 48% aqueous HBr. The mixture was warmed to room temperature and stirred for an additional 16 hours. The reaction mixture was neutralized with 3 M aqueous NaOH, filtered through a pad of Celite, and extracted with EtOAc (3×100 mL). The combined organic fractions were dried over anhydrous $Na_2SO_4$ and concentrated under vacuum to give 1.2 g (4.17 mmol) of crude product that was used without further purification. $^1H$ NMR (300 MHz, $CD_3OD$): δ 1.87 (s, 3H), 3.48 (dd, 1H, J=11.0, 5.9), 3.69 (dd, 1H, J=11.0, 6.5), 4.01 (m, 1H), 4.91 (d, 1H, J=3.6), 7.30 (d, 2H, J=8.3), 7.45 (d, 2H, J=8.3).

Example 3

Compound 6

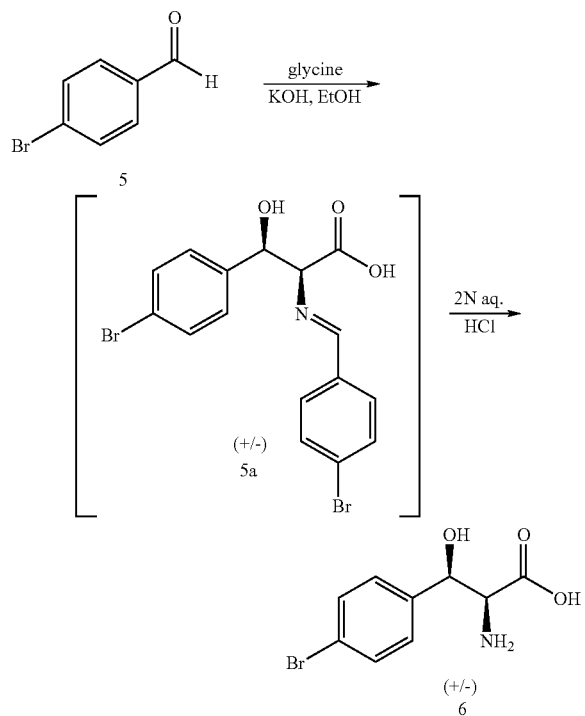

4-Bromobenzaldehyde (100 g, 0.540 mol) was dissolved in ethanol (EtOH) in a 2 L round-bottom flask. With rapid stirring, glycine (0.5 molar equivalents, 20.3 g, 0.270 mol) and then, in one portion, KOH (30.3 g, 0.540 mol) were added. It is essential to add the KOH all at once. Thus, an ice bath should be used when performing the reaction on a larger scale to control the exotherm. After addition of the KOH, the turbid suspension became yellow and homogeneous. After about 15 minutes, a thick white precipitate began to form. The mixture was stirred for 12 hours at room temperature under $N_2$. Enough 2 N aqueous HCl was added (~400 mL) to make the solution red to pH paper. The mixture was then stirred at approximately 60° C. until it again become a homogeneous yellow solution. The EtOH was removed under vacuum to give an aqueous suspension of white precipitate. The precipitate was filtered and the remaining aqueous solution washed three times with EtOAc. The aqueous solution was then basified to about pH 9 with concentrated aqueous $NH_3$ and excess ammonia was removed under vacuum. As the $NH_3$ was removed, the product, 6, began to precipitate. Evaporation continued to one-quarter the volume of solution where precipitation was first observed. The product was then collected on a vacuum filter and dried under vacuum to a constant weight (51.3 g). If NMR indicates the presence of the undesired trans stereoisomer, it can be removed by recrystallization from $H_2O$/EtOH). $^1H$ NMR (300 MHz, $CD_3OD$): δ 3.64 (d, 1H, J=3.6), 5.25 (d, 1H, J=3.6), 7.41 (d, 2H, J=8.4), 7.53 (d, 2H, J=8.4).

Example 4

Compound 7

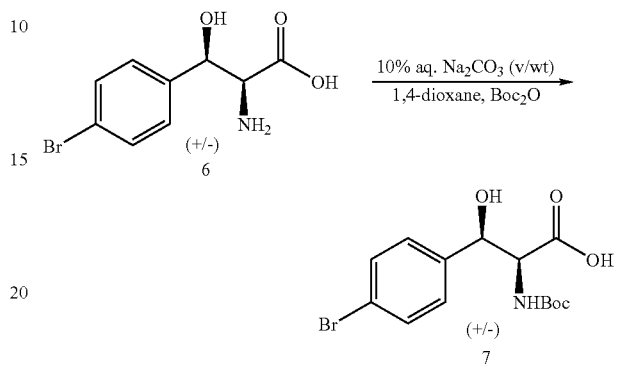

Compound 6 (32.60 g, 12.53 mmol) was dissolved in 10% aqueous $K_2CO_3$ (10% w/v; 500 mL). Di-tert-butyl dicarbonate (34.2 g, 157 mmol) was dissolved in 1,4-dioxane (500 mL) and added to the aqueous solution, after which the mixture was stirred at room temperature for 72 hours. The mixture was concentrated under vacuum and taken up in 100 mL 1 N aqueous NaOH and washed with $Et_2O$ (2×100 mL). The aqueous layer was acidified with 1 N aqueous HCl and the product extracted into EtOAc (3×200 mL). The combined EtOAc extracts were dried over anhydrous $Na_2SO_4$, filtered, and concentrated under vacuum. The product (26.7 g, 74.0 mmol) was isolated and used without further purification. $^1H$ NMR (300 MHz, $CD_3OD$): δ 1.32 (s, 9H), 4.37 (d, 1H, J=2.7), 5.23 (d, 1H, J=2.7), 7.32 (d, 2H, 8.4), 7.46 (d, 2H, J=8.4).

Example 5

Compound 8

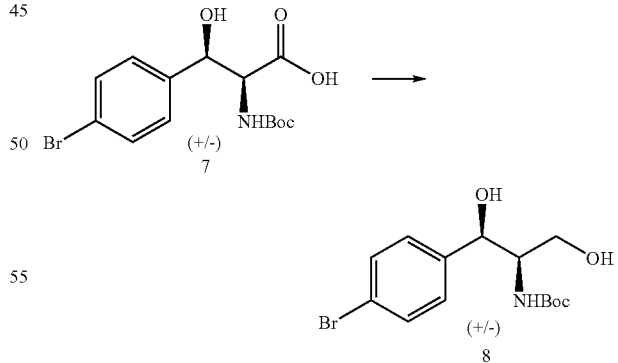

Compound 7 (5.29 g, 14.7 mmol) and N-hydroxysuccinimide (1.69 g, 14.7 mol) were dissolved in EtOAc (200 mL) and the mixture cooled to 0° C. N,N'-dicyclohexyl-carbodiimide (3.04 g, 14.7 mmol) was added and the mixture stirred for 30 minutes, warmed to room temperature and stirred for 30 additional minutes. It was then cooled to 0° C. and filtered to remove the precipitated N,N'-dicyclohexylurea byproduct. The filtrate was concentrated under vacuum and the residue dissolved in THF (100 mL). The solution was cooled to 0° C., NaBH₄ (5.6 g, 150 mmol) added, and the mixture stirred for two minutes. Water was then added to the mixture dropwise until bubbling ceased, then a volume of water equal to the volume of THF was added over 30 minutes, after which the mixture was warmed to room temperature and stirred for 5 hours. The dioxane was removed under vacuum and EtOAc (200 mL) was added, followed by gradual acidification of the aqueous layer with 1 N aqueous HCl. The EtOAc layer was washed with brine and dried over anhydrous Na₂SO₄. Filtration followed by concentration under vacuum gave 4.31 g (12.4 mmol) of 8, which was used without further purification. ¹H NMR (300 MHz, CD₃OD): δ 1.32 (s, 9H), 3.46–3.51 (m, 1H), 3.63–3.73 (m, 2H), 4.88 (br s, 1H), 7.29 (d, 2H, J=8.3), 7.45 (d, 2H, J=8.3).

Example 6

Compound 9 (from 4)

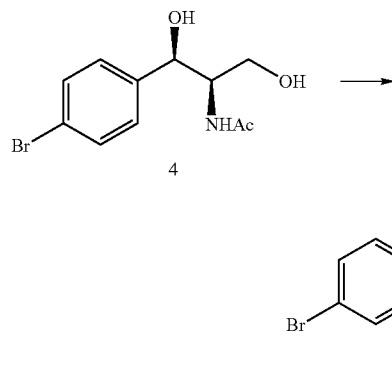

Compound 4 (1.0 g, 3.5 mmol) was dissolved in 10% aqueous H₂SO₄ (10% v/v, 15 mL total) and the solution refluxed for 10 h. The reaction mixture was basified with 3 M aqueous NaOH and extracted with EtOAc (3×50 mL). The combined EtOAc fractions were dried over anhydrous Na₂SO₄ and concentrated under vacuum to give 710 mg (2.9 mmol) of 4, which was used without further purification. ¹H NMR (300 MHz, CD₃OD): δ 2.80–2.90 (br m, 1H), 3.30–3.39 (br m, 1H), 3.40–3.50 (br m, 1H), 4.52–4.58 (m, 1H), 7.30 (d, 2H, J=8.1), 7.49 (d, 2H, J=8.1).

Example 7

Compound 9 (from 8)

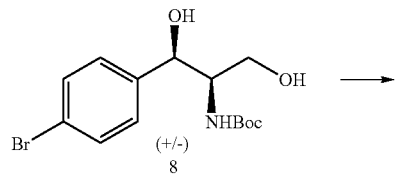

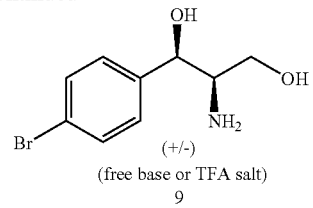

Compound 8 (4.31 g, 12.4 mmol) was dissolved in trifluoroacetic acid (TFA, 40 mL). The mixture was stirred for 3 hours at room temperature and concentrated under vacuum. The TFA salt was partitioned between 50 mL of 2 N aqueous NaOH and an equal volume of EtOAc. The layers were separated and the aqueous layer was washed with EtOAc (50 mL). The combined EtOAc fractions were washed with brine, dried over anhydrous Na₂SO₄ and concentrated under vacuum to give a waxy solid (2.72 g, 11.1 mmol), which was used without further purification. ¹H NMR (300 MHz, CD₃OD): δ 2.83–2.90 (m, 1H), 3.30–3.35 (m, 1H), 3.46 (dd, 1H, J=10.8, 4.8), 4.56 (d, 1H, J=6.6), 7.29 (d, 2H, J=8.6), 7.49 (d, 2H, J=8.6).

Example 8

Compound 10

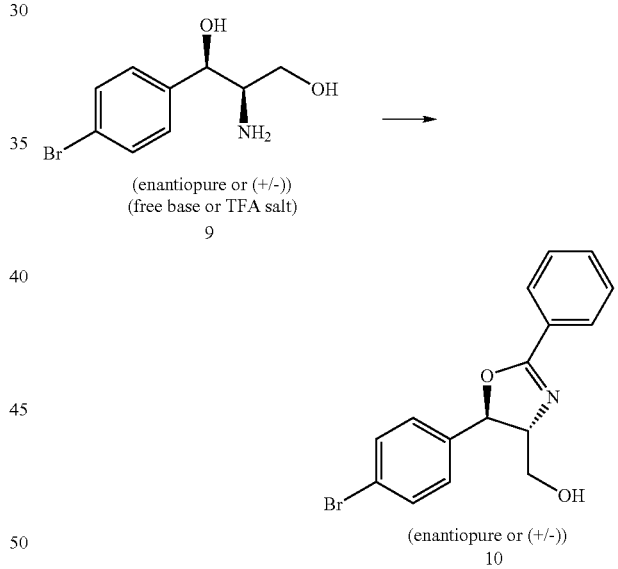

Compound 9 (710 mg, 2.89 mmol), ethyl benzimidate hydrochloride (533 mg, 2.89 mmol) and triethylamine (Et₃N, 0.40 mL, 2.89 mmol) were combined in 25 mL 1,2-dichloroethane. The mixture was refluxed with stirring under N₂ for 16 hours at which time TLC indicated one major product. After cooling to room temperature, the mixture was diluted with EtOAc, washed twice with saturated aqueous NH₄Cl, twice with saturated aqueous NaHCO₃ and then dried over anhydrous Na₂SO₄. The solution was filtered and the EtOAc removed under vacuum to give 885 mg (2.66 mmol) of 10, which was used without further purification. ¹H NMR (300 MHz, CD₃OD): δ 3.74–3.89 (m, 2H), 4.13–4.18 (m, 1H), 5.59 (d, 1H, J=6.6), 7.30 (d, 2H, J=8.4), 7.46–7.57 (m, 5H), 7.99–8.02 (m, 2H).

Example 9

Compound 11

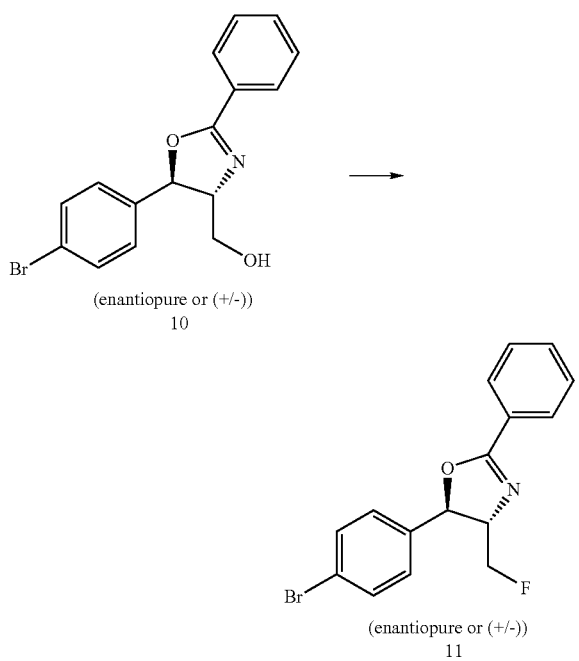

(enantiopure or (+/−))
10

(enantiopure or (+/−))
11

Compound 10 (885 mg, 2.66 mmol) was suspended in CH$_2$Cl$_2$ (15 mL) and cooled to −78° C. Diethylaminosulfur trifluoride (DAST, 0.53 mL, 4.00 mmol) was added by syringe, the mixture warmed over 1 hour to room temperature and then stirred for 16 hours under N$_2$. Excess DAST was quenched by slow addition of H$_2$O after which the mixture was diluted with additional CH$_2$Cl$_2$. The organic layer was washed with H$_2$O and saturated aqueous NaHCO$_3$, dried over anhydrous Na$_2$SO$_4$ and concentrated under vacuum. The residue (950 mg) was chromatographed on silica gel, eluting with 15:85 EtOAc/hexanes to give 11 as an oil (420 mg, 1.25 mmol). $^1$H NMR (300 MHz, CDCl$_3$): δ 4.23–4.35 (m, 1H), 4.45–4.75 (m, 2H), 5.43 (d, 1H, J=6.9), 7.17(d, 2H, 8.3), 7.36–7.47 (m, 5H), 7.96 (d, 2H, J=8.3).

Example 10

Compound 12

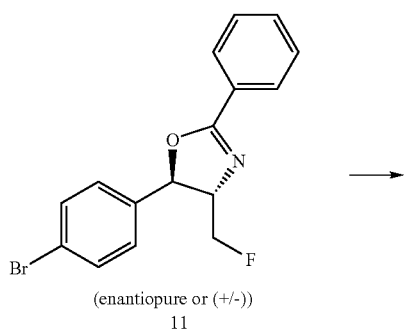

(enantiopure or (+/−))
11

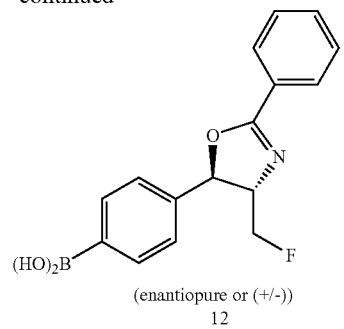

(enantiopure or (+/−))
12

Compound 11 (807 mg, 2.41 mmol, enantiopure from chloramphenicol or racemic from (+/−)-threo-p-bromophenylserine), was dissolved in anhydrous THF (10 mL) in a flame-dried round bottom flask and cooled to −78° C. n-BuLi (1.6 M in hexanes, 3.02 mL, 4.83 mmol) was added with vigorous stirring. After 10 minutes, trimethyl borate (0.55 mL, 4.83 mmol) was added, the mixture warmed to room temperature over 1 hour and then stirred for 6 hours. The mixture was quenched with 1 N aqueous HCl and extracted three times with EtOAc. The combined EtOAc fractions were washed three times with brine and dried over anhydrous Na$_2$SO$_4$. The EtOAc was removed under vacuum to give 805 mg of material, which was purified by flash column chromatography, eluting initially with 1:1 hexanes/EtOAc to remove impurities followed by elution with 1:9 MeOH/CH$_2$Cl$_2$ to obtain the product as an oil (285 mg, 0.953 mmol). $^1$H NMR (300 MHz, CD$_3$OD): δ 4.29–4.39 (m, 1H), 4.69 (dd, 2H, J=47.1, 4.2), 5.64 (d, 1H, J=6.6), 7.37 (d, 2H, J=8.1), 7.47–7.52 (m, 2H), 7.56–7.62 (m, 1H), 7.67 (d, 1H, J=7.5) 7.74–7.82 (m, 1H), 8.01 (d, 2H, J=7.2).). LRMS (ESI$^-$) m/z: 298.0 M−H$^+$ C$_{16}$H$_{14}$BFNO$_3$ requires 298.1).

Example 11

Compound 13

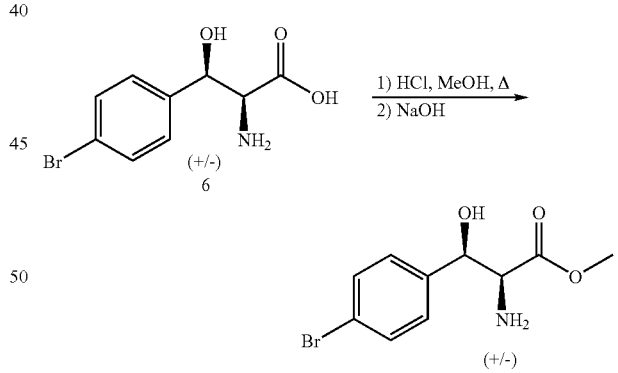

Compound 6 (20.6 g, 0.079 mol) was suspended in 400 mL of anhydrous MeOH. The mixture was stirred rapidly and cooled in an ice bath to 0° C. Anhydrous HCl gas was slowly bubbled in. After 10 minutes, all solids had dissolved. Acidification was continued for 10 minutes after the mixture became homogeneous, at which point the MeOH turned pH paper very red. The apparatus was fitted with a drying tube and the reaction mixture was refluxed for 8 hours followed by stirring at room temperature for 12 hours. The mixture was concentrated under vacuum and then suspended in a mixture of 300 mL of EtOAC and 100 mL of water. With rapid stirring, 3 N NaOH was added very slowly until the suspended material dissolved. Addition of base was continued until a pH of 10 was attained. The layers were separated and the EtOAc fraction was washed with brine (2×) and dried over anhydrous $Na_2SO_4$. Concentration under vacuum gave 13 as a white powder (15.3 g), which was used without further purification. $^1$H NMR (300 MHz, $CD_3OD$): δ 3.59 (d, 1H, J=4.5), 3.66 (s, 3H), 4.92 (d, 1H, J=4.5), 7.29 (d, 2H, J=8.3), 7.49 (d, 2H, J=8.3).

Example 12

Compound 14

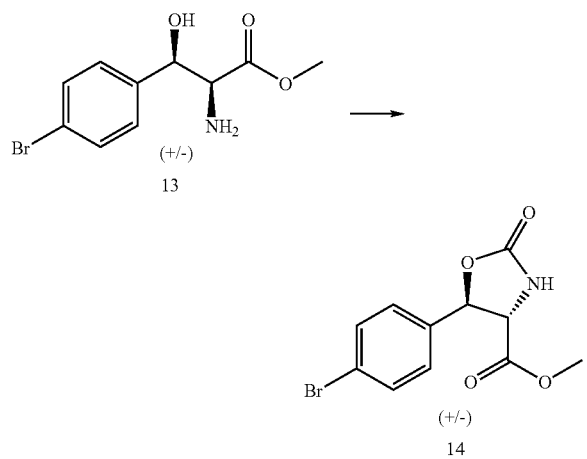

1,1'-Carbonyldiimidazole (23.6 g, 0.146 mol) was dissolved in 250 mL of anhydrous 1,2-dichloroethane at room temperature followed by addition of triethylamine ($Et_3N$, 12.2 g, 16.8 mL). In a separate flask, 13 (33.26 g, 0.121 mol) was dissolved in 125 mL of anhydrous tetrahydrofuran (THF) and an equivalent of triethylamine. The THF solution was diluted with 125 mL of 1,2-dichloroethane and then added, under $N_2$, over 2 hours to the 1,1'-carbonyldiimidazole solution. After addition was complete, the mixture was stirred for 2 hours under $N_2$ at room temperature. The reaction mixture was concentrated under vacuum and the residue diluted with 300 mL of EtOAc, which was washed with 5×200 mL of 2 N HCl, 3×300 mL of saturated $NaHCO_3$, and 2×200 mL of brine. The EtOAc layer was dried over anhydrous $Na_2SO_4$, filtered, and concentrated under vacuum to give 34.27 g of 14, 80–90% pure by $^1$H NMR. Compound 14 was used without further purification. $^1$H NMR (300 MHz, $CD_3OD$): δ 3.83 (s, 3H), 4.34 (d, 1H, J=5.0), 5.65 (d, 1H, J=5.0), 7.36 (d, 2H, J 8.7), 7.60 (d, 2H, J=8.7).

Example 13

Compound 15

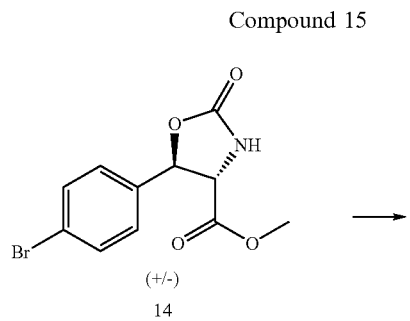

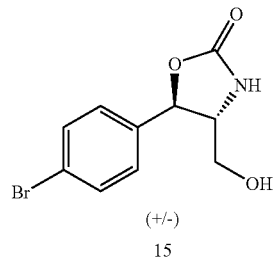

Compound 14 (55.3 g, 0.184 mmol) was dissolved in 375 mL MeOH. The solution was cooled to 0° C. and $NaBH_4$ (2 equivalents, 13.9 g, 0.369 mol) was added in portions, care being taken to not let the temperature exceed 20° C. After the last portion was added, cooling was ceased and the mixture stirred for 2 hours. Glacial acetic acid was added slowly until a pH of 7 was achieved. The mixture was filtered through Celite and concentrated under vacuum. The residue was partitioned between EtOAc (375 mL) and 2 N HCl (500 mL). The organic layer was washed with 2 N HCl (2×300 mL), saturated aqueous $NaHCO_3$ (2×250 mL) and brine (250 mL), dried over anhydrous $Na_2SO_4$, filtered and concentrated under vacuum. The product was crystallized from hexanes/EtOAc to give 26.3 g of 15. $^1$H NMR (300 MHz, $CD_3OD$): δ 3.64–3.72 (m, 3H), 5.38 (d, 1H, J=5.1), 7.32 (d, 2H, J=8.6), 7.57 (d, 2H, J=8.6).

Example 14

Compound 16

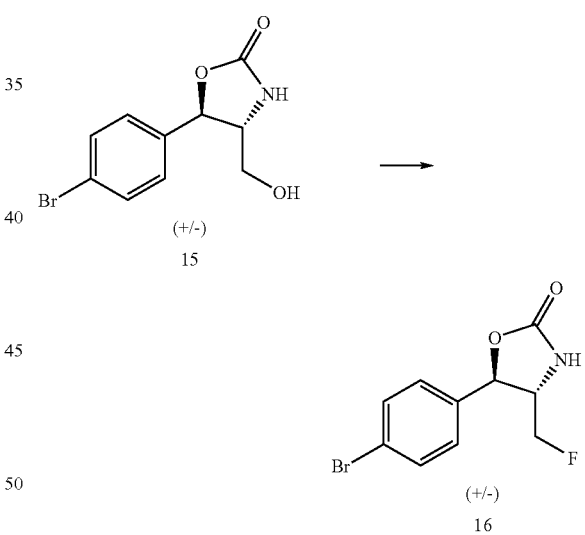

Compound 15 (7.57 g, 0.0278 mol) was suspended in 275 mL of $CH_2Cl_2$. Under $N_2$ and with rapid stirring, the biphasic mixture was cooled to −78° C. in a dry ice/acetone bath. DAST (5.51 mL, 6.72 g, 0.0417 mol) was added dropwise by syringe over 2–3 minutes. After 30 minutes the mixture was transferred to an ice water bath and stirred for 30 minutes, during which time the solids dissolved. Another 1 mL of DAST was added to ensure completion of the reaction. The mixture was stirred for 20 minutes at 0° C. and then warmed to room temperature. The mixture was stirred at room temperature for 20 minutes and then cooled to 0° C. Excess DAST was quenched by dropwise addition of saturated aqueous $NaHCO_3$ over 30 minutes with very rapid stirring. After bubbling ceased, the aqueous layer was slightly basic (7<pH<9). The $CH_2Cl_2$ was diluted with enough EtOAc (~600 mL) to bring the organic layer to the top during aqueous extraction. The organic layer was washed with saturated aqueous NaHCO$_3$ (1×300 mL), 1 N HCl (2×200 mL), saturated aqueous NaHCO$_3$ (3×200 mL) and brine (1×150 mL) and dried over anhydrous Na$_2$SO$_4$. After filtration, the mixture was concentrated under vacuum to give 8.13 g of brown oil. $^1$H NMR (300 MHz, CD$_3$OD): δ 3.87–3.98 (dm, 1H, J=20 (F—CH$_N$)), 4.54 (dd, 2H, J=46.7 (CH$_2$—F), 4.2), 5.42 (d, 1H, J=5.1), 7.34 (d, 2H, J=8.4), 7.59 (d, 2H, J=8.4).

Example 15

Compound 17

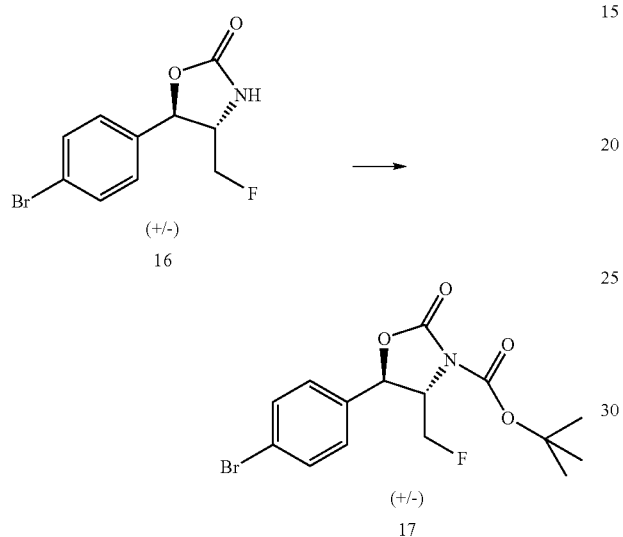

Compound 16 (8.13 g or 0.0297) was dissolved in 200 mL of CH$_3$CN. Boc$_2$O (9.71 g, 1.5 equivalents, 0.0445 mol) and DMAP (362 mg, 0.00297 mol, 0.1 equivalent) were then added. The mixture was stirred for 2 hours at room temperature under N$_2$. Concentration of the mixture under vacuum was followed by partitioning between 200 mL of EtOAc and 200 mL of 1 N HCl. The EtOAc layer was washed with 2 N HCl (3×100 mL), saturated aqueous NaHCO$_3$ (2×100 ML) and brine. The EtOAc layer was filtered, dried over anhydrous Na$_2$SO$_4$ and concentrated under vacuum. The residue was recrystallized twice from hexanes/EtOAc. $^1$H NMR (300 MHz, CD$_3$OD): δ 1.53 (s, 9H), 4.29–4.40 (dm, 1H, J=24.6), 4.63–4.98 (m, 2H), 5.53 (d, 1H, J=4.2), 7.34 (d, 2H, J=8.4), 7.61, (d. 2H, J=8.4).

Example 16

Compound 18

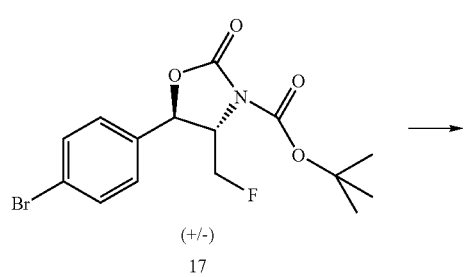

-continued

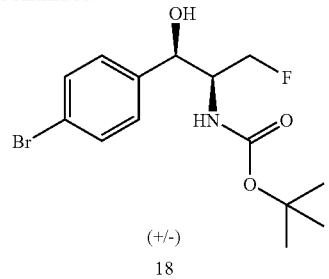

Compound 17 (0.050 g, 0.134 mmol) was suspended in 5 mL of CH$_3$OH. Cs$_2$CO$_3$ (8.7 mg, 20 mol %, 0.0267 mmol) was added with rapid stirring at room temperature. The solids dissolved in about 10 minutes after which stirring was continued for 10 minutes, at which time TLC (3:1 hexanes/EtOAc) indicated that the reaction was complete. The reaction mixture was concentrated under vacuum and the residue partitioned between 20 mL of EtOAc and 10 mL of H$_2$O. The H$_2$O layer was acidified slightly with 1N aqueous HCl, the mixture vigorously shaken and the layers separated. The EtOAc layer was washed with saturated aqueous NaHCO$_3$ (1×20 mL) and brine (1×20 mL). The EtOAc was dried over anhydrous Na$_2$SO$_4$ and concentrated under vacuum to give 43.4 mg (0.124 mmol) of 18 as a white foam. $^1$H NMR (300 MHz, CD$_3$OD): δ 1.33 (s, 9H), 3.90–4.57 (m, 4H), 7.29 (d, 2H, J=8.1), 7.46 (d. 2H, J=8.1)

Example 17

Compound 22

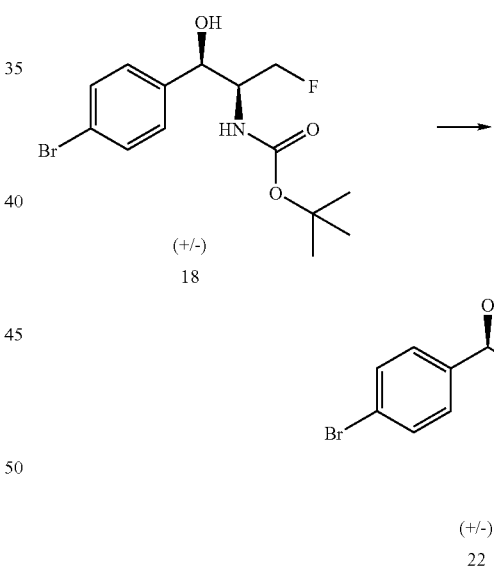

Compound 18 (0.740 g, 2.13 mmol) was stirred in 10 mL TFA/H$_2$O (9/1, v/v) at room temperature for one hour. The mixture was concentrated under vacuum and partitioned between 30 mL of EtOAc and 30 mL of 1 N aqueous NaOH. The mixture was shaken vigorously and the layers allowed to separate. The organic layer was washed with brine (2×), dried over anhydrous Na$_2$SO$_4$ and concentrated under vacuum to give 0.484 g (1.95 mmol, 92%) of product, which was dissolved in 20 mL of CH$_2$Cl$_2$. To this was added 1 mL of Et$_3$N and 1 mL of difluoroacetyl chloride, prepared according to literature procedure (Yu, K.-L., et al., *J. Med. Chem.*, 1996, 39, 2411–2421.). After 1 hour, the mixture was concentrated under vacuum. The residue was placed in 10 mL of a 1:8:1 (v/v/v) solution of Et₃N/MeOH/H₂O and stirred for one hour at room temperature to cleave any difluoroacetyl groups on the benzylic oxygen. The mixture was then concentrated under vacuum, and partitioned between EtOAc (50 mL) and 1 N HCl (50 ml). The EtOAc layer was washed twice with 20 mL of 1 N HCl, twice with 20 mL saturated aqueous NaHCO₃ and twice with 20 mL brine. The EtOAc was then dried over anhydrous Na₂SO₄, filtered, and concentrated under vacuum. Compound 22 (584 mg, 1.79 mmol) was used without further purification. $^1$H NMR (300 MHz, CD₃OD): δ 4.25–4.67 (m, 3H), 4.90 (d, 1H, J=3.9), 5.98 (t, 1H, J=53.9), 7.30 (d, 2H, J=8.6), 7.48 (d, 2H, J=8.6).

Example 18

Compound 19

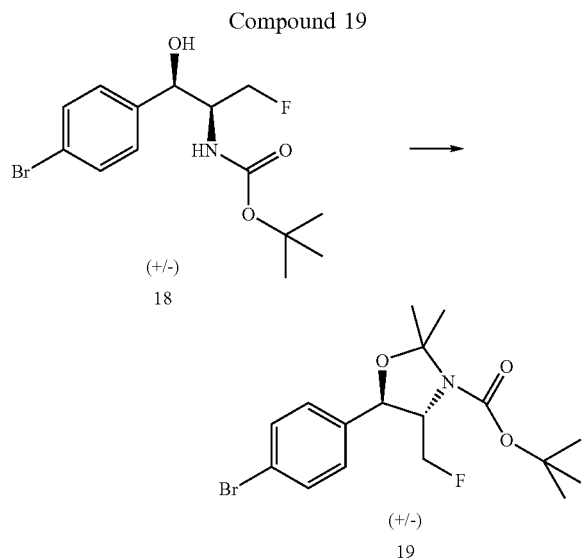

Compound 18 (1.03 g, 2.94 mmol) was dissolved in CH₂Cl₂ (30 mL) in a 50 mL round-bottom flask. 2-Methoxypropene (339 μL, 3.54 mmol) was added by syringe, followed by a single crystal of p-toluenesulfonic acid (p-TsOH) hydrate. After about 1 minute, the mixture turned yellow. TLC (4:1 hexanes/EtOAc) showed some 18 to still be present. An additional 5 drops of 2-methoxypropene were added followed two minutes later by another 5 drops, a which time TLC indicated the reaction was complete. The CH₂Cl₂ was removed under vacuum and the residue partitioned between EtOAc (75 mL) and saturated aqueous NaHCO₃ (50 mL). The EtOAc layer was washed twice with 50 mL NaHCO₃ and twice with brine. The EtOAc layer was dried over anhydrous Na₂SO₄, filtered and evaporated to give a yellow oil (1.08 g, 2.78 mmol) that solidified to a waxy solid, which was used without further purification. $^1$H NMR (300 MHz, CD₃OD): δ 1.49 (s, 9H), 1.55 (s, 3H), 1.67 (s, 3H), 3.70–3.85 (m, 1H), 4.34–4.53 (m, 2H), 5.08, (d. 1H, J=7.5), 7.37 (d, 2H, J=8.6), 7.54 d, 2H, J=8.6).

Example 19

Compound 23

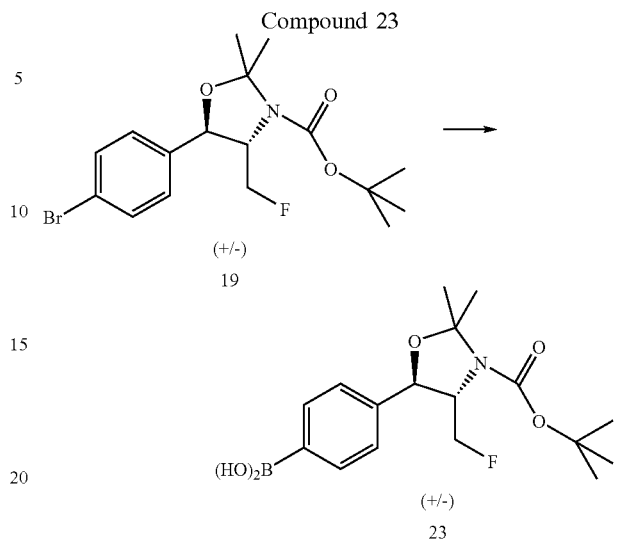

Compound 19 (309 mg, 0.796 mmol) was placed in an oven-dried 50 mL round-bottom flask equipped with a magnetic stir bar. The flask was immediately capped with a rubber septum and flushed with dry N₂. Anhydrous THF (15 mL) was added by syringe and a long cannula was used to flush the solvent with N₂ for 10 minutes. The mixture was then cooled to −78° C. With vigorous stirring, n-BuLi (850 μL, 0.995 mmol) was added dropwise by syringe over 3 minutes to give a clear orange solution. After 20 minutes, B(OMe)₃ (158 μL, 1.39 mmol), which had been stored over 4 Å activated molecular sieves for at least 48 hours, was added dropwise over one minute using an oven-dried, gas-tight syringe. The mixture was warmed to room temperature and stirred under N₂ for 16 hours. Approximately 20 mL of saturated aqueous NH₄Cl was added with vigorous stirring, which resulted in a white precipitate dispersed in the two liquid phases. The mixture was stirred for an additional 90 minutes and then diluted with EtOAc and H₂O until all the precipitate dissolved. The organic layer was separated, washed with brine and dried over anhydrous Na₂SO₄. After filtration, the EtOAc was removed under vacuum to give 328 mg of yellow oil. The product was purified by silica gel chromatography to give 23 (163 mg). $^1$H NMR (300 MHz, CD₃OD): δ 1.49 (s, 9H), 1.56 (s, 3H), 1.67 (s, 3H), 3.74–3.88 (m, 1H), 4.33–1.52 (m, 2H), 5.10 (d, 1H, J=7.5), 7.43 (d, 2H, J=8.1), 7.64 (d, 2H, J=8.1). LRMS (ESI⁻) m/z: 352.2 (M−H⁺ C₁₇H₂₄BFNO₅ requires 352.7).

Example 20

Compound 28

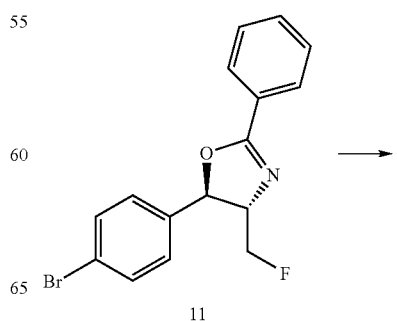

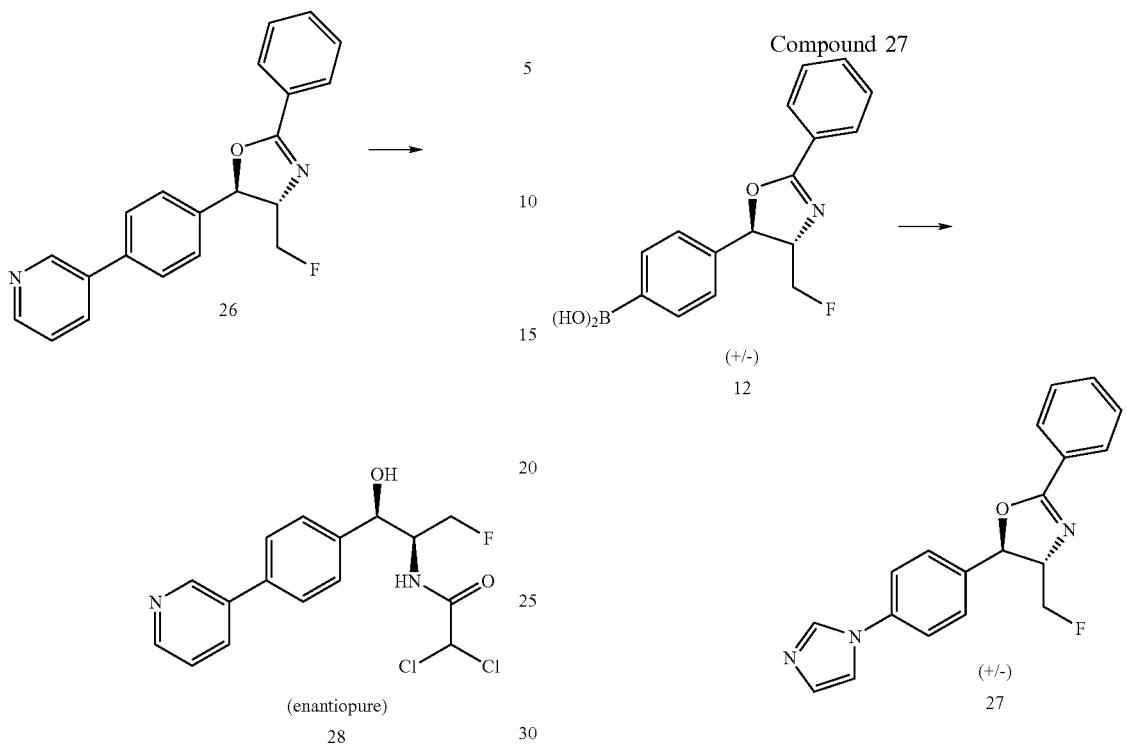

This is an example of Suzuki coupling method A. Compound 11 (47 mg, 0.14 mmol) and pyridine-3-boronic acid (21 mg, 0.17 mmol) were dissolved in 5.0 mL of THF. Pd(PPh$_3$)$_4$ (11 mg, 0.0098 mmol) and 3.0 mL of 10% (w/v) aqueous Na$_2$CO$_3$ were added. The reaction mixture was refluxed for 16 hours, cooled, diluted with EtOAc and washed twice with 10% (w/v) aqueous Na$_2$CO$_3$ and twice with brine. The EtOAc layer was then dried over anhydrous Na$_2$SO$_4$, filtered, and concentrated under vacuum. Silica gel chromatography (eluting with 1:1 hexanes/EtOAc) gave 47 mg (0.14 mmol) of 26. Intermediate 26 was heated to 105° C. in a sealed tube with 6M aqueous HCl and held at that temperature for 16 hours. The mixture was cooled to room temperature and basified to pH 10 with 3 N NaOH. The product was extracted into EtOAc, which was dried over Na$_2$SO$_4$, filtered, and concentrated under vacuum to give 42 mg of the deprotected free amine, contaminated with the expected benzoic acid-related by-product arising from cleavage of the protecting group. The crude residue was dichloroacetylated as in the synthesis of 29. Silica gel chromatography, eluting with 7.5% MeOH in CH$_2$Cl$_2$, gave 10 mg of product. $^1$H NMR (300 MHz, CD$_3$OD): δ 4.31–4.74 (m, 3H), 5.02 (d, 1H, J=3.6), 6.27 (s, 1H), 7.49–7.56 (m, 3H), 7.64 (d, 2H, J=8.4), 8.09 (ddd, 1H, J=8.0, 2.3, 1.5), 8.50 (br d, 1H, J=3.9), 8.78 (br s, 1H). LRMS (ESI$^+$) m/z: 356.9 (calc. for M+H$^+$: C$_{16}$H$_{16}$Cl$_2$FN$_2$O$_2$ 357.0).

Example 21

Compound 27

Boronic acid 12 (43 mg, 0.144 mmol), imidazole (15 mg, 0.215 mmol) and 4 Å powdered molecular sieves (110 mg) were combined in CH$_2$Cl$_2$ (4.0 mL) and pyridine (23 μL). With rapid stirring, Cu(OAc)$_2$ (26 mg, 0.144 mmol) was added and the mixture stirred, exposed to air, for 40 hours at room temperature. The mixture was quenched with 3 mL of 2 M NH$_3$ in MeOH. The mixture was filtered through Celite and concentrated under vacuum. The product was purified by flash column chromatography (19:1 CH$_2$Cl$_2$/MeOH). Although $^1$H NMR indicated that a significant side-product had eluted with the desired product, the mixture was used without further purification. LRMS (ESI$^+$) m/z: 321.9 (calc. for M+H$^+$ C$_{19}$H$_{17}$FN$_3$O 322.1).

Example 22

Compound 29

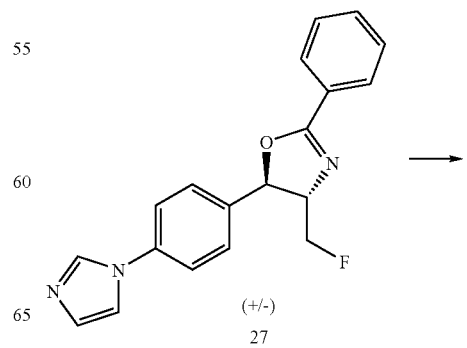

-continued

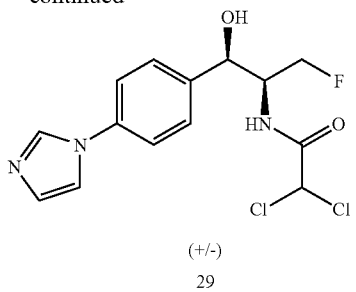

(+/-)
29

Compound 27 (27 mg, 0.084 mmol) was heated with 6 N HCl (3.0 mL) to 100° C. in a sealed tube and held for 16 hours. The mixture was cooled to room temperature, basified with 3 N aqueous NaOH and extracted three times with EtOAc. The combined EtOAc fractions were dried over anhydrous $Na_2SO_4$, filtered, and concentrated under vacuum to give 9 mg of residue. LRMS (ESI$^+$) m/z: 236.1 (Calc. for M+H$^+$ $C_{12}H_{15}FN_3O$ 236.1).

The residue was refluxed in MeOH (5.0 mL) containing $Et_3N$ (26 μL 0.189 mmol) and methyl dichloroacetate (13 μL, 0.126 mmol) for 3 hours. The mixture was concentrated under vacuum and purified by silica gel chromatography (7.5% MeOH in $CH_2Cl_2$) to give 29 (6.0 mg, 0.017 mmol). $^1$H NMR (300 MHz, $CD_3OD$): δ 4.33–4.75 (m, 3H), 5.03 (d, 1H, J=3.3), 6.26 (s, 1H), 7.13 (s, 1H), 7.51–7.58 (m, 5H), 8.10 (s, 1H). LRMS (ESI$^+$) m/z: 345.8 (calc. for M+H$^+$ $C_{14}H_{15}Cl_2FN_3O_2$ 346.0).

Example 23

Compound 34

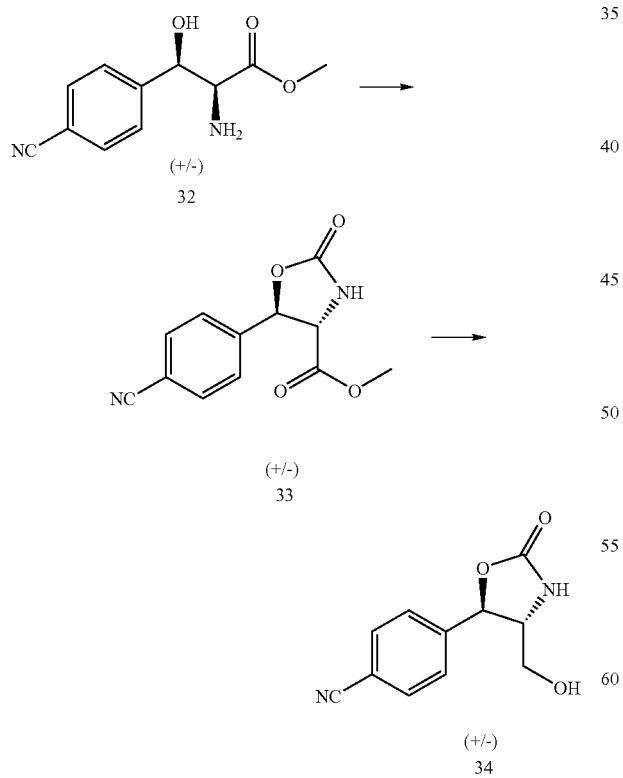

Compound 32 was prepared by the procedure of Pines, et al., supra. In a 250-mL round-bottom flask was placed 1,1'-carbonyldiimidazole (CDI, 5.06 g, 31.2 mmol) and $Et_3N$ (2.17 mL, 15.6 mmol) in 1,2-dichloroethane (50 mL). Compound 32 (4.00 g, 15.6 mmol) was added to a beaker containing 1,2-dichloroethane (50 mL). $Et_3N$ (4.34 mL, 31.2 mmol) was added to the beaker upon which a thick suspension formed. Additional 1,2-dichloroethane (20 mL) and THF (50 mL) were added to thin the suspension. The mixture was added portion-wise to the CDI suspension over 30 min. The mixture, which became mostly homogenous and turned yellow was stirred for 12 hours. The solvent was removed under vacuum and the residue was partitioned between 2 N aqueous HCl and EtOAc. The EtOAc layer was washed with 2 N HCl (2×45 mL), saturated aqueous $NaHCO_3$ (2×30 mL) and brine. It was dried over anhydrous $Na_2SO_4$, filtered, and evaporated to give 3.27 g of 33 as a fluffy yellow solid, which was used without further purification.

Compound 33 (1.00 g, 4.06 mmol) was dissolved in MeOH (50 mL) and cooled to 0° C. in an ice bath. Over 5 minutes, $NaBH_4$ (308 mg, 8.13 mmol) was added portion-wise. After bubbling ceased, TLC (5% MeOH in $CH_2Cl_2$) indicated that starting material remained so 100 mg additional $NaBH_4$ was added. After bubbling ceased, the mixture was quenched with glacial HOAc until a pH of approximately 7 was achieved. The mixture was concentrated under vacuum and partitioned between EtOAc and 1 N HCl. The EtOAc layer was washed with saturated aqueous $NaHCO_3$ (2×40 mL) and brine (40 mL) and dried over anhydrous $Na_2SO_4$. The product was isolated by silica gel chromatography (2% to 3% to 4% to 10% MeOH in $CH_2Cl_2$) to give 128 mg of 34 as an oil. Additional product was obtained by evaporation of the aqueous layer followed by trituration with hot EtOAc (153 mg, 281 mg total). $^1$H NMR (300 MHz, $CD_3OD$): δ 3.69 (br s, 3H), 5.50 (br s, 1H), 7.58 (d, 2H, J=7.8), 7.79 (d, 2H, J=7.8).

Example 24

Compound 35

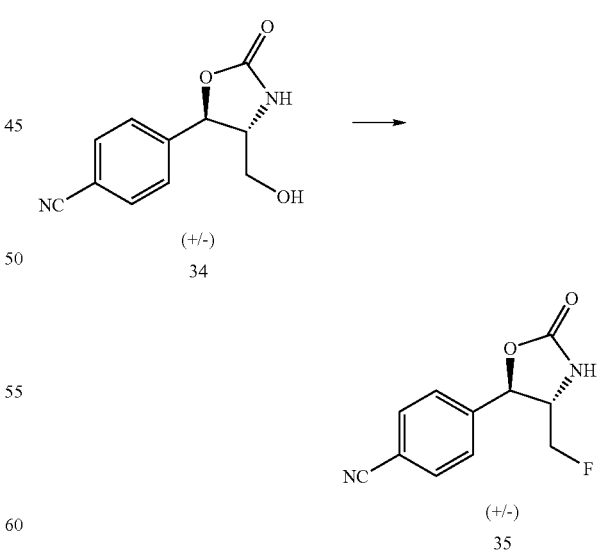

Fluorination was performed using DAST as in the synthesis of compound 11. $^1$H NMR (300 MHz, $CD_3OD$): δ 3.89–3.97 (m, 1H), 4.49–4.66 (m, 2H), 5.55 (d, 1H, J=4.8), 7.59 (d, 2H, J=8.1), 7.80 (d, 2H, J=8.4).

Example 25

Compound 38

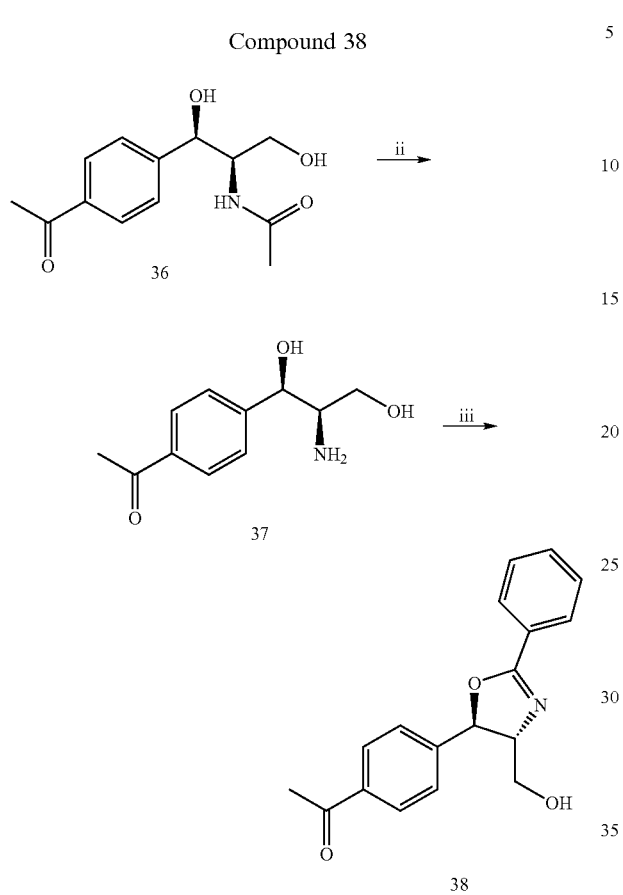

Compound 36 (2.12 g), was prepared by the procedure of von Strandtmann, supra. It was heated with 10% aqueous H$_2$SO$_4$ to 100° C. in a sealed tube and held for 4 hours. After cooling to room temperature, the mixture was basified with 1 M NaOH and extracted three times with n-butanol. The n-butanol fractions were combined and dried over anhydrous Na$_2$SO$_4$. The solvent was evaporated to give 1.61 g of 37.

Compound 37 (1.61 g, 7.70 mmol) was dissolved in 1,2-dichloroethane (100 mL), along with ethyl benzimidate hydrochloride (1.42 g, 7.70 mmol), and Et$_3$N (1.06 mL, 7.70 mmol). The mixture was refluxed for 12 hours, cooled to room temperature and diluted with EtOAc. The solution was washed with saturated aqueous NH$_4$Cl (3×) and saturated NaHCO$_3$ (1×) and dried over anhydrous Na$_2$SO$_4$. The product precipitated from the EtOAc on cooling and addition of several drops of hexanes to give 0.62 g of 38 (2.1 mmol). $^1$H NMR (300 MHz, CD$_3$OD): δ 2.60 (s, 3H), 3.79 (dd, 1H, J=11.3, 5.9), 3.89 (dd, 1H, J=11.3, 4.1), 4.14–4.20 (m, 1H), 5.70 (d, 1H, 6.3), 7.47–7.61 (m, 5H), 8.01–8.05 (m, 4H).

Example 26

Compound 39

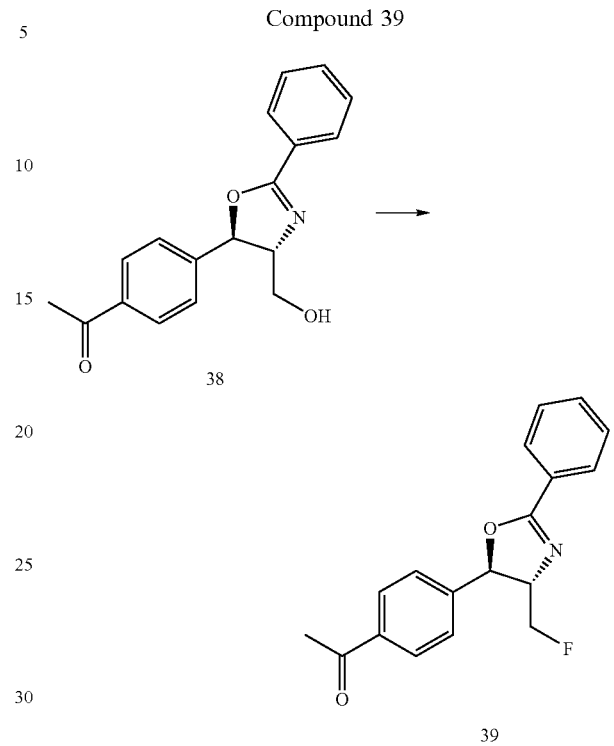

Compound 38 (0.62 g, 2.1 mmol) was suspended in CH$_2$Cl$_2$ (15 mL) and cooled to −78° C. DAST (0.42 mL, 3.1 mmol) was added by syringe and the solution stirred overnight, during which time it was allowed to come to room temperature as the cold bath warmed. The solvent was removed under vacuum and the product isolated by silica gel chromatography (1:4 EtOAc/hexanes) to give 0.17 g of 39. $^1$H NMR (300 MHz, CD$_3$OD): δ 2.60 (s, 3H), 4.30–4.40 (m, 1H), 4.63–4.67 (m, 1H), 4.79–4.81 (m, 1H), 5.74 (d, 1H, 6.9), 7.48–7.63 (m, 5H), 8.01–8.07 (m, 4H).

Example 27

Compound 40

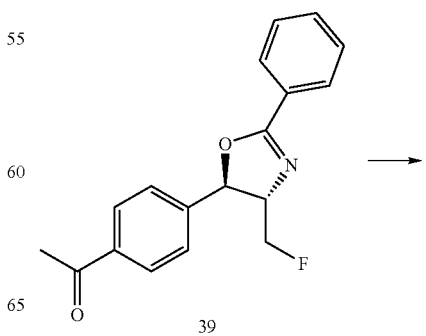

-continued

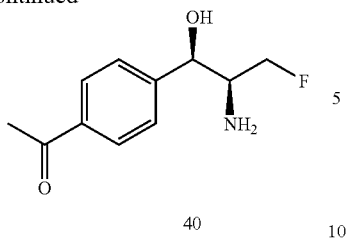
40

Compound 39 (0.17 g, 0.58 mmol) was suspended in 6 N aqueous HCl (5 mL) in a sealed tube. The mixture was heated to 100° C. and held for 12 hours. After cooling to room temperature, the mixture was basified with 3 N NaOH and the product extracted into CH$_2$Cl$_2$ (3×). The combined CH$_2$Cl$_2$ fractions were dried over anhydrous Na$_2$SO$_4$, filtered and concentrated to give 40 (0.113 g, 0.541 mmol). $^1$H NMR (300 MHz, CD$_3$OD): δ 2.60 (s, 3H), 3.04–3.15 (m, 1H), 4.09–4.48 (m, 3H), 4.71 (d, 1H, J=6.0), 7.52 (d, 2H, J=8.1), 7.90 (d, 2H, J=8.1).

Example 28

Compound 41

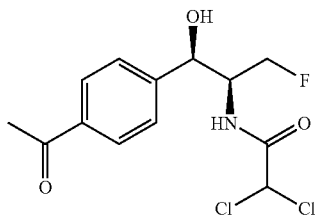

Compound 40 was dichloroacetylated to give 41 in the same manner that 27 was converted to 29. $^1$H NMR (300 MHz, CD$_3$OD): δ 2.57 (s, 3H), 4.31–4.78 (m, 3H,), 5.03 (d, 1H, J=3.3), 6.23 (s, 1H), 7.53 (d, 2H, J=8.6), 7.95 (d, 2H, J=8.6).

Example 29

Compound 43

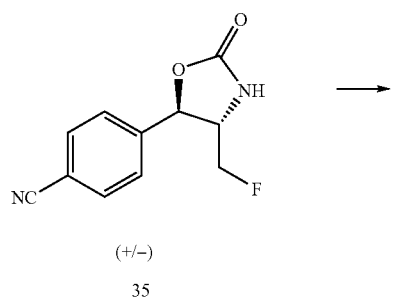
(+/−)
35

-continued

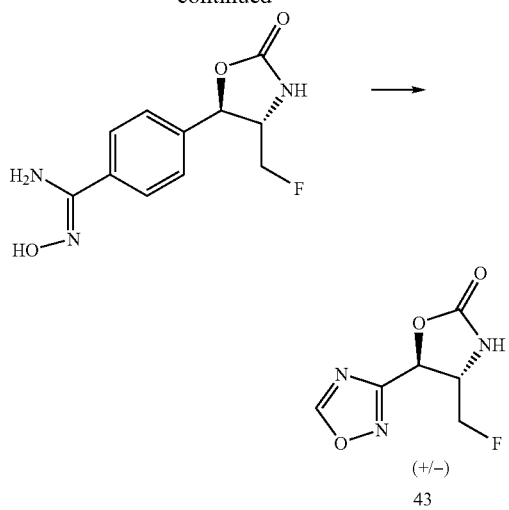
43
(+/−)

Compound 35 (100 m, 0.454 mmol) was dissolved in 3 mL of EtOH and transferred to a 25 ml round-bottom flas, Hydroxylamine hydrochloride (38 mg, 0.545 mmol) was added followed by Et$_3$N (127 μL, 0.909 mmol). The mixture was stirred at reflux for 3 hours, at which point TLC indicated complete consumption of starting material. The mixture was concentrated under vacuum to 232 mg of yellow oil, which was used without further purification. A portion of the oil (115 mg) was dissolved in 10 mL of triethylorthoformate. The mixture was stirred at 120° C. under N$_2$ for 2 hours and then at room temperature for 48 hours. TLC (10 % MeOH in CH$_2$Cl$_2$) a major new spot. The triethyl orthoformate was removed under vacuum and the residue partitioned between EtOAc and 1 N aqueous NaOH. The organic layer was washed with 1 N aqueous NaOH (2×) and brine (2×). The EtOAc layer was dried over anhydrous Na$_2$SO$_4$, and evaporated, to give 84 mg of oil. The product was purified by chromatotron (1 mm silica plate, 60:40 to 50:50 to 40:60 hexanes/EtOAc). Another purification by chromatotron (2 % MeOH in CH$_2$Cl$_2$) gave 43 (20 mg) as a white solid. $^1$H NMR (300 MHz, CD$_3$OD): δ 3.93–4.04 (m, 1H), 4.49–4.67 (m, 2 H), 5.53 (d, 1 H, J ×5.1), 7.59 (d, 2 H, J ×8.3), 8.17 (d, 2 H, J ×8.3), 9.28 (s, 1 H).

Example 30

Compound 45

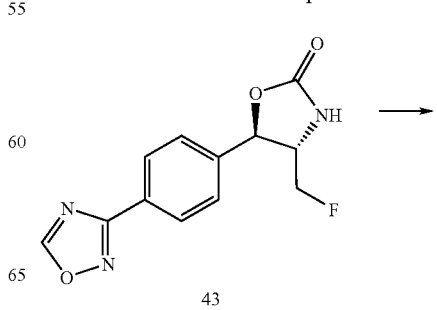
43

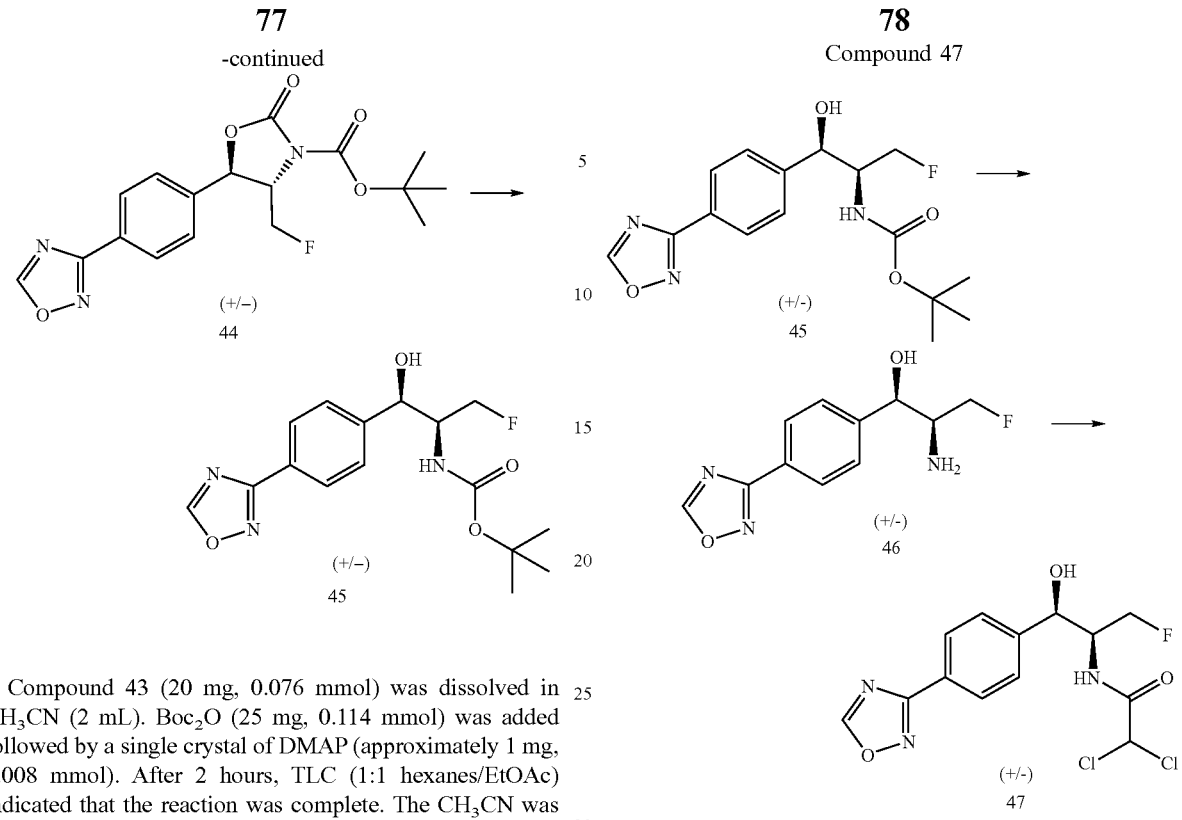

Compound 43 (20 mg, 0.076 mmol) was dissolved in CH₃CN (2 mL). Boc₂O (25 mg, 0.114 mmol) was added followed by a single crystal of DMAP (approximately 1 mg, 0.008 mmol). After 2 hours, TLC (1:1 hexanes/EtOAc) indicated that the reaction was complete. The CH₃CN was removed under vacuum and the resulting white solid dissolved in EtOAc, which was washed with 1 N aqueous HCl (2×), followed by NaHCO₃ (2×) then brine. The organic layer was dried over anhydrous Na₂SO₄, filtered, and concentrated under vacuum to give 44 as a white solid (28 mg).

Compound 44 (0.026 mg, 0.072 mmol) was dissolved in MeOH (2 mL) and Cs₂CO₃ (5 mg, 0.014 mmol) was added in a single portion. After 1 hour, TLC (1:1 hexanes/EtOAc) showed a single product. The solvent was removed under vacuum, EtOAc added and the mixture stirred rapidly at room temperature. Then, H₂O was added, followed by 0.5 M HCl dropwise until all solids dissolved. The organic phase was washed with 0.5 N HCl, followed by saturated aqueous NaHCO₃ (2×) and brine. The organic layer was then dried over anhydrous Na₂SO₄, filtered and concentrated to give a yellow oil, which was purified by chromatotron (1 mm silica plate, 4:1 hexanes/EtOAc to 1:1 hexanes/EtOAc) to give 45 (13 mg, 0.039 mmol). $^1$H NMR (300 MHz, CD₃OD): δ 1.31 (s, 9H), 4.01–4.63 (m, 3H), 4.94 (d, 1H, J=2.7), 7.55 (d, 2H, J=8.4), 8.05 (d, 2H, J=8.4), 9.24 (s, 1H).

Example 30

Compound 45

Example 31 between EtOac and 1 N aqueous NaOH. The organic layer was washed with 1 N aqueous NaOH (2×) and brine (2). The EtOAc layer was dried over anhydrous Na₂SO₄, filtered and evaporated, to give 84 mg of oil. The product was purified by chromatotron (1 mm silica plate, 60:40 to 40:60 hexanes/EtOAc). Another purification by chromatotron (2 % MeOH in CH₂Cl₂) gave 43 (20 mg ) as a white solid. $^1$H NMR (300 MHz, CD₃OD): δ 3.93–4.49-4.67 (m, 2 H), 5.53 (d, 1J=5.1 ), 7.59 (d, 2H, J=8.3), 9.28 (s, 1H).

Compound 45 was dissolved in 2.5 mL of 9:1 TFA/H₂O in a 10 mL flask. The mixture was stirred at room temperature for 30 minutes, at which time TLC indicated completion of the reaction. The mixture was concentrated under vacuum and partitioned with rapid stirring between 1 N aqueous NaOH and EtOAc. The EtOAc layer was washed with brine (1×), dried over anhydrous Na₂SO₄, filtered and evaporated to give 11 mg of 46 as an oil To 6 mg (0.025 mmol) of 46 in a 10 mL round bottom flask was added MeOH (2 mL), followed by Et₃N (3.5 μL, 0.025 mmol) and methyl dichloroacetate (13.1 μL, 0.025 mmol). The mixture was refluxed for 4 hours at which time TLC indicated no reaction had occurred. An additional 26.2 μL of methyl dichloroacetate was added followed by 7 μL of Et₃N. The mixture was refluxed for 20 hours after which TLC indicated that the reaction was complete. The product was purified via chromatotron (1 mm silica gel plate, 99:1 CH₂Cl₂/MeOH) to give 5 mg 47. $^1$H NMR (300 MHz, CD₃OD): δ 4.32–4.72 (m, 3H), 5.03 (d, 1H, J=2.7), 6.25 (s, 1H), 7.56 (d, 2H, J=8.3), 8.05 (d, 2H, J=8.3), 9.24 (s, 1H). LRMS (ESI⁻) m/z: 346.0 (M–H⁺ C₁₃H₁₁Cl₂FN₃O₃ requires 346.0).

Example 32

Compound 24

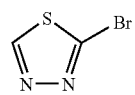

In a 200 mL round-bottom flask, 2-amino-1,3,4-thiadiazole (1.00 g, 9.89 mmol) was added to 10 mL of 48% aqueous HBr. Water (10 mL) was added to give a yellow solution in which most solids dissolved. The mixture was cooled to 0° C. and CuBr (142 mg, 0.989 mmol) was added to give an opaque brown solution with some precipitate. NaNO$_2$ (682 mg, 9.89 mmol) was dissolved in 25 mL H$_2$O and added dropwise over 45 minutes to the thiadiazole mixture. The mixture became dark green and opaque with the first drops of NaNO$_2$ solution. Slowly, the solution became brownish yellow and brown gas evolved. The mixture was stirred for an additional 10 minutes at 0° C. from the time gas evolution began. The mixture was warmed to room temperature over 30 minutes. Saturated aqueous NaHCO$_3$ was added dropwise until bubbling ceased and the pH was 8.5. To this was added 50 mL of EtOAc and the biphasic mixture stirred rapidly. The mixture was filtered through a pad of Celite to remove solids and then the layers were separated. The organics were washed with brine (2×). The aqueous layer was extracted with EtOAc and washed with brine (1×). The combined organic layers were dried over Na$_2$SO$_4$. The remaining aqueous material was extracted once more by vigorous stirring with EtOAc (50 mL) for 12 hours. This EtOAc layer was washed with brine and combined with the EtOAc that was already drying over Na$_2$SO$_4$. The solution was filtered and evaporated under vacuum to give 24 as a tan solid (1.22 g, 7.36 mmol), which was used without further purification.

Example 33

Compound 25

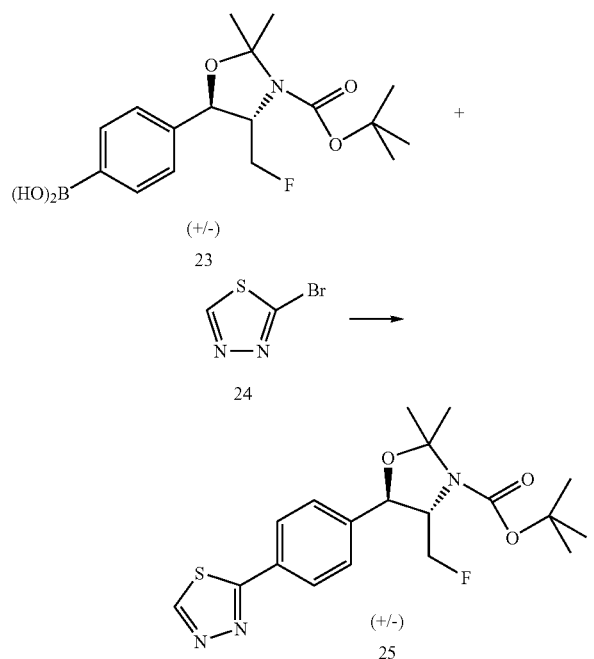

This is an example of Suzuki coupling method B. Compound 23 (19 mg, 0.0538 mmol) was dissolved in THF (1 mL), DMF (1 mL), and H$_2$O (0.5 mL). The mixture was stirred at room temperature until all material dissolved and then 2-bromo-1,3,4-thiadiazole (24, 5.0 mg, 0.027 mmol) was added. The solution was purged with N$_2$ for 5 minutes by means of a long needle. PdCl$_2$(dppf) was added and then the solution was again purged with N$_2$ for 5 minutes. The mixture was then stirred at 55° C. for 18 hours under N$_2$ and then at room temperature for an additional 30 hours. The resulting clear brown solution was concentrated under vacuum. Compound 25 (5.4 mg, 0.0137 mmol) was obtained as a yellow oil by chromatotron purification (silica gel, 1 mm plate, 1:9 EtOAc/hexanes to 1:4 EtOAc/hexanes).

It was found that the yield could be substantially improved by switching to coupling method C. Compounds 23 (0.330 g, 0.934 mmol) and 24 (0.385 g, 2.34 mmol) were dissolved in a mixture of toluene, n-butanol, and H$_2$O (8 mL:8 mL:2 mL) and Cs$_2$CO$_3$ (0.912 g, 2.80 mmol) was added. The mixture was purged with N$_2$ and Pd(PPh$_3$)$_4$ was added. The mixture was again purged with N$_2$ for 5 minutes and then stirred rapidly at 70° C. under N$_2$ for 12 hours. The mixture was concentrated under vacuum and the residue partitioned between H$_2$O (75 mL) and EtOAc (75 mL). The layers were separated and the EtOAc was washed with brine (2×50 mL). The EtOAc was dried over anhydrous Na$_2$SO$_4$, filtered, and concentrated under vacuum to give 0.720 g of yellow oil. Compound 25 (0.220 g) was obtained by silica gel chromatography, eluting with 5:1 to 2:1 to 1:1 hexanes/EtOAc. $^1$H NMR (300 MHz, CD$_3$OD): δ 1.50 (s, 9H), 1.58 (s, 3H), 1.70 (s, 3H), 3.80–3.94 (m, 1H), 4.42–4.61 (m, 2H), 5.20, (d. 1H, J=7.5), 7.64 (d, 2H., J=8.3), 8.05 (d, 2H, J=8.3), 9.45 (s, 1H).

Example 34

Compound 48

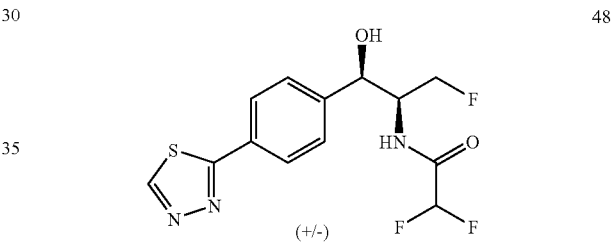

Compound 25 (5.4 mg, 0.014 mmol) was transferred to a 25 mL round-bottom flask and 2.5 mL of 9:1 TFA/H$_2$O (v/v) were added. The resulting bright yellow mixture was stirred at room temperature for 18 hours. The solvent was removed under vacuum and the residue dissolved three times in a mixture of MeOH and toluene, which was evaporated to near dryness each time. The product was recovered as an oil (4.9 mg, 0.013 mmol), which was used without further purification. $^1$H NMR (300 MHz, CD$_3$OD): δ 3.59–3.70 (m, 1H), 4.30–4.71 (m, 2H), 4.92 (d, 1H, J=8.1), 7.64 (d, 2H, J=8.3), 8.08 (d, 2H, J=8.3), 9.47 (s, 1H).

In a 10 mL round-bottom flask, the above product was dissolved in 2 mL of MeOH. To this was added Et$_3$N (9.7 μL, 0.070 mmol) followed by methyl difluoroacetate (3.0 μL, 0.035 mmol). The mixture was refluxed for 16 hours, at which point TLC indicated that some starting material still remained. An additional 3 drops of Et$_3$N was added followed by 2 drops of methyl difluoroacetate. After 3 hours, all starting material had been consumed. The mixture was cooled to room temperature and evaporated to dryness undervacuum. Compound 48 (4.1 mg, 012 mmol) was obtained by chromatotron purification (silica gel, 1 mm plate). $^1$H NMR (300 MHz, CD$_3$OD): δ 4.31–4.72 (m, 3H), 5.03 (d, 1H, J=3.9), 5.98 (t, 1H, J=53.9), 7.58 (d, 2H, J=8.3), 7.99 (d, 2H, J=8.3), 9.43 (s, 1H). LRMS (ESI$^-$) m/z: 330.1 (M−H$^+$ C$_{13}$H$_{11}$F$_3$N$_3$O$_2$S requires 330.1).

Example 35

Compound 49

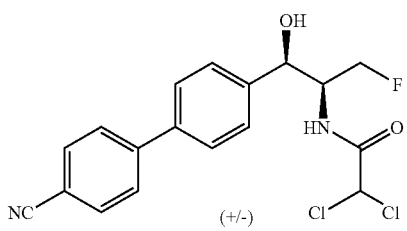

The biaryl intermediate was prepared from 18 and the appropriate boronic acid using Suzuki coupling method A. Removal of the Boc group was accomplished by brief treatment with 90/10 (v/v) TFA/H$_2$O. Dichloroacetylation was performed as in the synthesis of 29. $^1$H NMR (300 MHz, CD$_3$OD): δ 4.31–4.80 (m, 3H), 5.01 (d, 1H, J=3.6), 6.26 (s, 1H), 7.52 (d, 2H, 8.3), 7.65 (d, 2H, J=8.3), 7.79 (s, 4H). LRMS (ESI$^-$) m/z: 379.0 (M–H$^+$ C$_{18}$H$_{14}$Cl$_2$FN$_2$O$_2$ 379.0).

Example 36

Compound 50

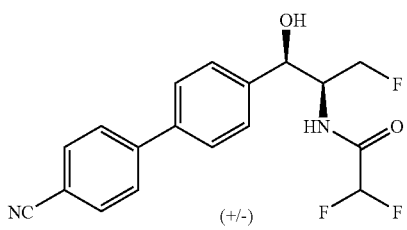

The biaryl intermediate was prepared from 22 and the appropriate boronic acid using Suzuki coupling method A. $^1$H NMR (300 MHz, CD$_3$OD): δ 4.27–4.68 (m, 3H), 4.99 (d, 1H, J=4.5), 6.00 (t, 1H, J=53.9), 7.52 (d, 2H, J=8.1), 7.67 (d, 2H, J=8.1), 7.76–7.82 (m, 2H). LRMS (ESI$^-$) m/z: 347.1 (M–H$^+$ C$_{18}$H$_{14}$F$_3$N$_2$O$_2$ requires 347.1).

Example 37

Compound 51

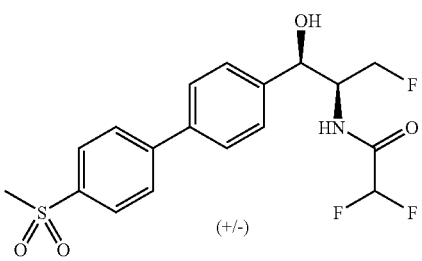

The biaryl intermediate was prepared from 22 and the appropriate boronic acid using Suzuki coupling method A. $^1$H NMR (300 MHz, CD$_3$OD): δ 3.14 (s, 3H), 4.30–4.68 (m, 3H), 5.00 (d, 1H, J=4.5), 6.00 (t, 1H, J=54), 7.53 (d, 2H, J=8.3), 7.70 (d, 2H, J=8.3), 7.88 (d, 2H, J=8.6), 8.00 (d, 2H, J=8.6). LRMS (ESI$^-$) m/z: 400.1 (M–H$^+$ C$_{18}$H$_{17}$F$_3$NO$_4$S requires 400.1).

Example 38

Compound 52

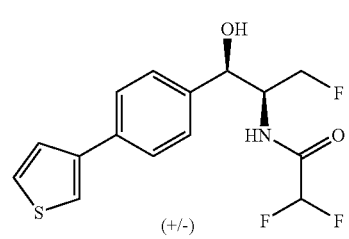

The biaryl intermediate was prepared from 22 and the appropriate boronic acid using Suzuki coupling method B. $^1$H NMR (300 MHz, CD$_3$OD): δ 4.26–4.64 (m, 3H), 4.93 (d, 1H, J=4.8), 6.01 (t, 1H, J=53.9), 7.40–7.45 (m, 4H), 7.60–7.66 (m, 3H). LRMS (ESI$^-$) m/z: 328.1 (M–H$^+$ C$_{15}$H$_{13}$F$_3$NO$_2$S requires 328.1).

Example 39

Compound 53

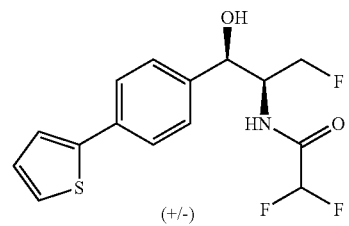

The biaryl intermediate was prepared from 22 and the appropriate boronic acid using Suzuki coupling method B. $^1$H NMR (300 MHz, CD$_3$OD): δ 4.25–4.65 (m, 3H), 4.92 (d, 1H, J=4.5), 6.01 (t, 1H, J=53.9), 7.06–7.08 (m, 1H), 7.36–7.42 (m, 4H), 7.61 (d, 2H, J=8.4). LRMS (ESI$^+$) m/z: 352.0 (calc. for M+Na$^+$ C$_{15}$H$_{14}$F$_3$NNaO$_2$S 352.1).

Example 40

Compound 54

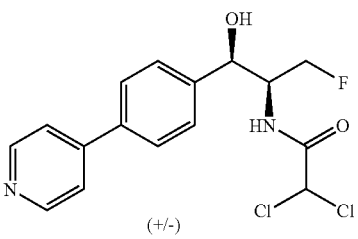

The biaryl intermediate was prepared from 18 and the boronic acid using Suzuki coupling method B. Removal of the Boc group was accomplished by brief treatment with 9/1 (v/v) TFA/H$_2$O. Dichloroacetylation was performed as in the synthesis of 29. $^1$H NMR (300 MHz, CD$_3$OD): δ 4.33–4.79 (m, 3H), 5.03 (d, 1H, J=3.3), 6.26 (s, 1H), 7.55 (d, 2H, J=8.4), 7.69–7.75 (m, 4H), 8.56 (d, 2H, J=5.7). LRMS (ESI$^+$) m/z: 357.1 (calc. for M+H$^+$ C$_{16}$H$_{16}$Cl$_2$FN$_2$O$_2$ 357.1).

Example 41

Compound 55

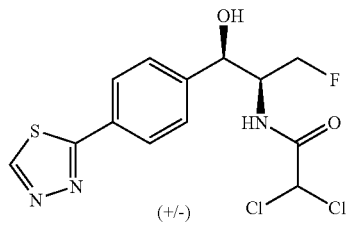

(+/-)

The biaryl intermediate was prepared from boronic acid 23 and compound 24 using Suzuki coupling method B. Removal of the protecting groups was accomplished by brief treatment with 9/1 (v/v) TFA/H$_2$O. Dichloroacetylation was performed as in the synthesis of 29. $^1$H NMR (300 MHz, CD$_3$OD): δ 4.34–4.76 (m, 3H), 5.04 (d, 1H, J=3.0), 6.24 (s, 1H), 7.58 (d, 2H, J=8.3), 7.97 (d, 2H, J=8.3), 9.42 (s, 1H). LRMS (ESI$^-$) m/z: 362.0 (calc. for M–H$^+$ C$_{13}$H$_{11}$Cl$_2$FN$_3$O$_2$S 362.0).

Example 42

Compound 56

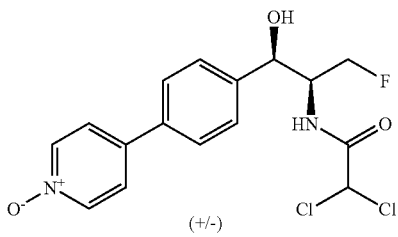

(+/-)

Compound 54 (29.4 mg, 0.0824 mmol) was dissolved in 5 mL of CH$_2$Cl$_2$. The mixture was cooled to 0° C. and m-chloroperbenzoic acid (m-CPBA, 38 mg, 0.16 mmol) was added with stirring. After 5 minutes, the mixture was warmed to room temperature and stirred for 12 hours. The mixture was concentrated under vacuum and the product purified by silica gel chromatography eluting successively with 2%, 3%, 4%, 6%, and10% MeOH in CH$_2$Cl$_2$. Compound 56 was obtained as a white solid (22.5 mg, 0.060 mmol). $^1$H NMR (300 MHz, CD$_3$OD): δ 4.32–4.75 (m, 3H), 5.03 (d, 1H, J=3.3), 6.25 (s, 1H), 7.56 (d, 2H, J=8.4), 7.74 (d, 2H, J=8.4), 7.84 (d, 2H, J=7.2), 8.34 (d, 2H, J=7.2). LRMS (ESI$^-$) m/z: 371.0 (calc. for M–H$^+$ C$_{16}$H$_{14}$Cl$_2$FN$_2$O$_3$ 371.0).

Example 43

Compound 57

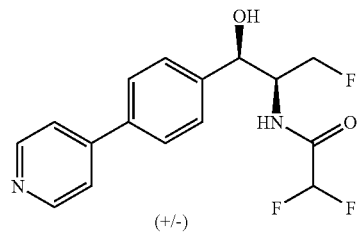

(+/-)

The biaryl intermediate was prepared from 18 and the appropriate boronic acid using Suzuki coupling method B. Removal of the protecting group was accomplished by brief treatment with 9/1 (v/v) TFA/H$_2$O. Difluoroacetylation was performed as in the synthesis of 48. $^1$H NMR (300 MHz, CD$_3$OD): δ 4.28–4.68 (m, 3H), cn 5.00 (d, 1H, J=4.2), 5.99 (t, 1H, J=53.9), 7.55 (d, 2H, J=8.1), 7.70–7.77 (m, 4H), 7.84>(d, 2H, J=7.2), 8.56 (d, 2H, J=6.3). LRMS (ESI$^+$) m/z: 325.2 (calc. for M+H$^+$ C$_{16}$H$_{16}$F$_3$N$_2$O$_2$ 325.1).

Example 44

Compound 58

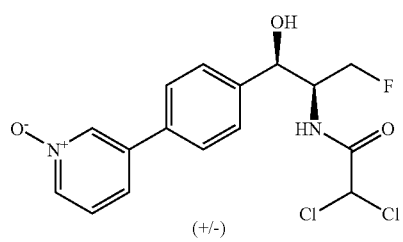

(+/-)

Compound 58 was prepared from 68 as 56 was from 54. $^1$H NMR (300 MHz, CD$_3$OD): δ 4.30–4.75 (m, 3H), 5.02 (d, 1H, J=3.3), 6.25 (s, 1H), 7.55–7.67 (m, 5H), 7.87 (d, 1H, J=8.1), 8.30 (d, 1H, J=7.2), 8.58 (br s, 1H). LRMS (ESI$^-$) m/z: 371.0 (calc. for M–H$^+$ C$_{16}$H$_{14}$Cl$_2$FN$_2$O$_3$ 371.0).

Example 45

Compound 59

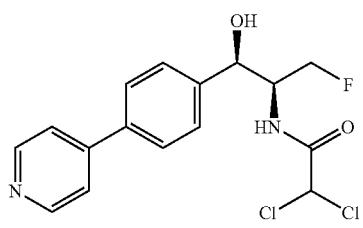

The biaryl intermediate was prepared from 11 and the appropriate boronic acid using Suzuki coupling method A. The phenyloxazoline protecting group was removed and the dichloroacetate group introduced as in the synthesis of 29. $^1$H NMR (300 MHz, CD$_3$OD): δ 4.30–4.75 (m, 3H), 5.02 (d, 1H, J=3.6), 6.26 (s, 1H), 7.54–8.70 (m, 8H). LRMS (ESI$^-$) m/z: 354.8 (calc. for M–H$^+$ C$_{16}$H$_{14}$Cl$_2$FN$_2$O$_2$ 355.0).

Example 46

Compound 60

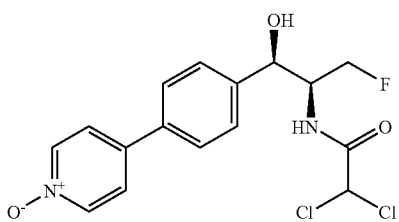

Compound 60 was prepared from compound 59 in the same manner that other pyridine N-oxides in these examples were formed from the corresponding pyridine. ¹H NMR (300 MHz, CD$_3$OD): δ 4.33–4.78 (m, 3H), 5.03 (d, 1H, J=3.3), 6.25 (s, 1H), 7.57 (d, 2H, J=8.4), 7.75 (d, 2H, J=8.4), 7.87 (d, 2H, J=7.5), 8.38 (d, 2H, J=7.5). LRMS (ESI⁻) m/z: 370.8 (calc. for M−H⁺ C$_{16}$H$_{14}$Cl$_2$FN$_2$O$_3$ 371.0).

Example 47

Compound 61

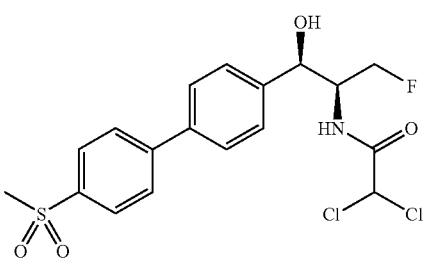

The biaryl intermediate was prepared from 11 and the appropriate boronic acid using Suzuki coupling method A. The phenyl oxazoline protecting group was cleaved and dichloroacetate introduced as in the synthesis of 29. ¹H NMR (300 MHz, CD$_3$OD): δ 3.14 (s, 3H), 4.36–4.75 (m, 3H), 5.02 (d, 1H, J=3.6), 6.27 (s, 1H), 7.54 (d, 2H, J=8.3), 7.68 (d, 2H, J=8.3), 7.87 (d, 2H, J=8.7), 8.01 (d, 2H, J=8.7). LRMS (ESI⁻) m/z: 431.8 (calc. for M−H⁺ C$_{18}$H$_{17}$Cl$_2$FNO$_4$S 432.0).

Example 48

Compound 62

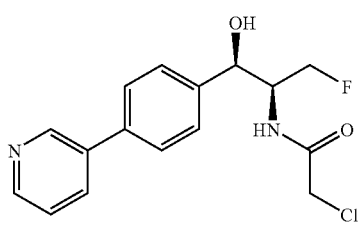

The free amine intermediate was prepared as in the synthesis of 28. The nitrogen was monochloroacetylated using chloroacetyl chloride. ¹H NMR (300 MHz, CD$_3$OD): δ 4.00–4.03 (m, 2H), 4.27–4.70 (m, 3H), 5.00 (d, 1H, J=3.9), 7.49–7.55 (m, 3H), 7.66 (d, 2H, J=8.4), 8.09 (d app t, 1H, J=7.8, 2.4), 8.50 (dd, 1H, J=4.8, 1.5), 8.78 (br d, 1H, J=2.4). LRMS (ESI⁺) m/z: 321.0 (calc. for M+H⁺ C$_{16}$H$_{15}$ClFN$_2$O$_2$ 357.1).

Example 49

Compound 63

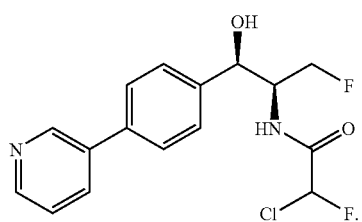

Prepared in the same manner as 28 using ethyl chlorofluoroacetate. ¹H NMR (300 MHz, CD$_3$OD): δ 4.31–4.70 (m, 3H), 5.01 (d, 1H, J=3.9), major diastereomer 6.49 (d, 1H, J=49.8), minor diastereomer 6.51 (d, 1H, J=49.8), 7.49–7.56 (m, 3H), 7.63–7.67 (m, 2H), 8.07–8.11 (m, 1H), 8.49–8.51 (m, 1H), 8.78 (br d, 1H, J=1.5). LRMS (ESI) m/z: 338.9 (calc. for M−H⁺ C$_{16}$H$_{14}$ClF$_2$N$_2$O$_2$ 339.1).

Example 50

Compound 64

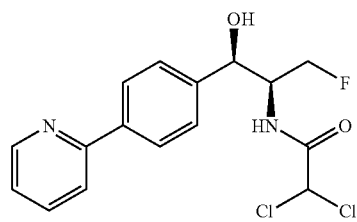

The biaryl intermediate was prepared from 12 and 2-bromopyridine using Suzuki coupling method A. ¹H NMR (300 MHz, CD$_3$OD): δ 4.28–4.74 (m, 3H), 5.02 (d, 1H, J=3.6), 6.27 (s, 1H), 7.33–7.37 (m, 1H), 7.53 (d, 2H, J=8.1), 7.18–7.93 (m, 4H), 8.58–8.60 (m, 1H). LRMS (ESI⁻) m/z: 354.8 (calc. for M−H⁺ C$_{16}$H$_{14}$Cl$_2$FN$_2$O$_2$ 355.0)

Example 51

Compound 65

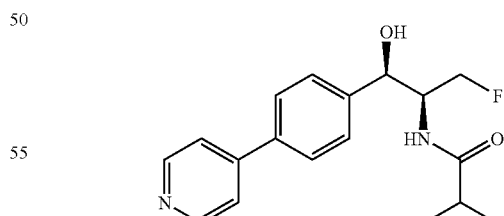

Compound 65 was prepared in the same manner as 59 using ethyl chlorofluoroacetate. ¹H NMR (300 MHz, CD$_3$OD): δ 4.32–4.70 (m, 3H), 5.02 (d, 1H, J=3.6), major diastereomer 6.48 (d, 1H, J=49.8), minor diastereomer 6.50 (d, 1H, J=50.1), 7.55–7.58 (m, 2H), 7.73–7.78 (m, 4H) 8.57 (br d, 2H, J=5.7). LRMS (ESI⁻) m/z: 338.8 (calc. for M−H⁺ C$_{16}$H$_{14}$ClF$_2$N$_2$O$_2$ 339.1).

Example 52

Compound 66

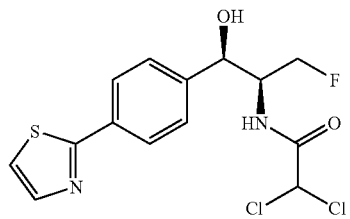

The biaryl intermediate was prepared from 12 and the appropriate bromide using Suzuki coupling method A. Removal of the protecting group and dichloroacetylation was accomplished as in the synthesis of 29. $^1$H NMR (300 MHz, CD$_3$OD): δ 4.34–4.72 (m, 3H), 5.01 (d, 1H, J=2.4), 6.25 (s, 1H), 7.52 (d, 2H, J=6.3), 7.57 (d, 1H, J=2.6) 7.84 (d, 1H, J=2.6), 7.90 (d, 2H, J=6.3). LRMS (ESI$^-$) m/z: 360.7 (calc. for M–H$^+$ C$_{14}$H$_{12}$Cl$_2$FN$_2$O$_2$S 361.0).

Example 53

Compound 67

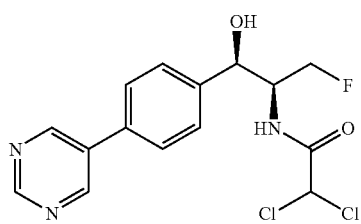

The biaryl intermediate was prepared from 12 and the appropriate bromide using Suzuki coupling method A. Removal of the protecting group and dichloroacetylation was accomplished as in the synthesis of 29. $^1$H NMR (300 MHz, CD$_3$OD): δ 4.32–4.75 (m, 3H), 5.04 (d, 1H, J=3.6), 6.26 (s, 1H), 7.59 (d, 2H, J=8.3), 7.70 (d, 2H, J=8.3) 9.06 (s, 2H,), 9.13 (s, 1H). LRMS (ESI$^+$) m/z: 357.8 (calc. for M+H$^+$ C$_{15}$H$_{15}$Cl$_2$FN$_3$O$_2$ 358.0).

Example 54

Compound 68

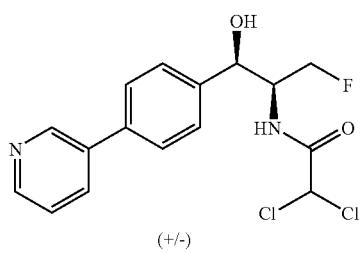

The biaryl intermediate was prepared from bromide 11 and the appropriate boronic acid using Suzuki coupling method A. Removal of the protecting group and dichloroacetylation was accomplished as in the synthesis of 29. $^1$H NMR (300 MHz, CD$_3$OD): δ 4.31–4.74 (m, 3H), 5.02 (d, 1H, J=3.6), 6.27 (s, 1H), 7.48–7.51 (m, 1H), 7.54 (d, 2H, J=8.3), 7.64 (d, 2H, J=8.3) 8.08 (ddd, 1H, J=8.0, 2.4, 1.8), 8.50 (dd, 1H, 4.8, 1.5), 8.77 (dd, 1H, J=2.4, 0.9). LRMS (ESI$^-$) m/z: 354.8 (calc. for M–H$^+$ C$_{16}$H$_{14}$Cl$_2$FN$_2$O$_2$ 355.0).

Example 55

Compound 69

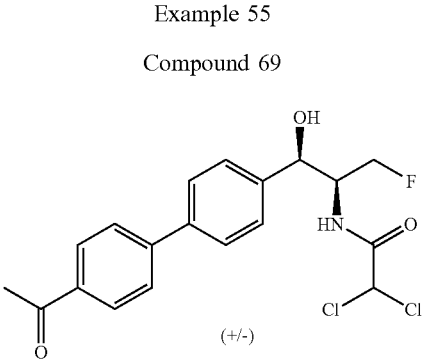

The biaryl intermediate was prepared from bromide 11 and the appropriate boronic acid using Suzuki coupling method A. Removal of the protecting group and dichloroacetylation was performed as in the synthesis of 29. $^1$H NMR (300 MHz, CD$_3$OD): δ 2.63 (s, 3H), 4.31–4.74 (m, 3H), 5.01 (d, 1H, J=3.9), 6.27 (s, 1H), 7.51 (d, 2H, J=8.3), 7.67 (d, 2H, J=8.3), 7.75 (d, 2H, J=8.6) 8.06 (d, 2H, J=8.6).

Example 56

Compound 71

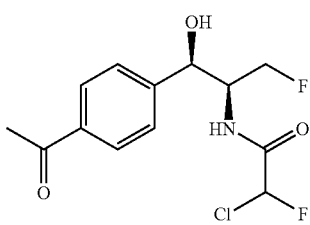

This compound was prepared in analogous fashion to 41 using ethyl chlorofluoroacetate in place of methyl dichloroacetate. $^1$H NMR (300 MHz, CD$_3$OD): δ 2.58 (s, 3H), 4.31–4.71 (m, 3H), 5.03 (br d, 1H, J=3.9), major diastereomer 6.46 (d, 1H, J=49.8), minor diastereomer (d, 1H, J=50.1), major diastereomer 7.53 (d, 2H, J=8.1), minor diastereomer 7.51 (d, 2H, J=8.1), 7.94–7.96 (m, 2H). LRMS (ESI$^-$) m/z: 304.1 (calc. for M–H$^+$ C$_{13}$H$_{13}$ClF$_2$NO$_3$ 304.1).

Example 57

Compound 72

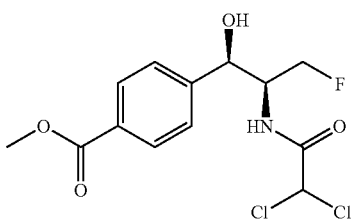

Initially, the p-cyano analog of compound 11 had been prepared by methods analogous to those used to prepare 11 itself. Attempts to remove the phenyloxazoline protecting group (as described in the synthesis of 29) led to some of the desired deprotected nitrile intermediate. However, much of the mass recovered was the deprotected p-carboxylic acid corresponding to acidic hydrolysis of the nitrile functional group. This material was dichloroacetylated using the same procedure as that employed in the synthesis of 29 and the product was converted to its methyl ester with $CH_2N_2$. $^1H$ NMR (300 MHz, $GD_3OD$): δ 3.83 (s, 3H), 4.25–4.66 (m, 3H), 4.98 (d, 1H, J=3), 6.17 (s, 1H), 7.46 (d, 2H, J=8.3), 7.91 (d, 2H, J=8.3).

Example 58

Compound 73

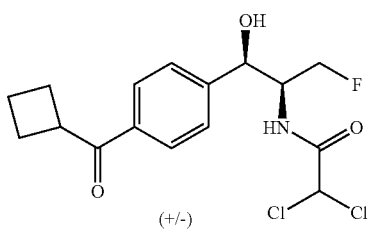

(+/−)

Compound 87 (36.5 mg, 0.0873 mmol) was dissolved in THF (5 mL anhydrous) under $N_2$. After addition of anhydrous powdered $K_2CO_3$ (24 mg, 0.175 mmol), the mixture was purged with $N_2$. $Et_3N$ (31 mL, 0.218 mmol) and cyclobutanecarbonyl chloride (13 mL, 0.113 mmol) were added and the mixture purged gently with $N_2$ for another 5 min. $Pd_2 dba_3$ was added and the mixture purged again with $N_2$. The mixture was then stirred under $N_2$ for 3 hours after which it was diluted with EtOAc and $H_2O$ and filtered through a cotton plug. The EtOAc layer was washed with 1 N aqueous HCl (×2), brine (×2), and dried over anhydrous $Na_2SO_4$. The mixture was filtered and the solvent removed to give 16.9 mg, 0.0501 mmol of material that was purified by chromatotron (1 mm plate, eluting with 4:1 hexanes/EtOAc). The protected intermediate obtained was subjected to phenyloxazoline cleavage and dichloroacetylation as in the synthesis of 29 to give 73. $^1H$ NMR (300 MHz, $CD_3OD$): δ 1.73–1.85 (m, 1H), 1.99–2.11 (m, 1H), 2.20–2.27 (m, 4H), 3.97–4.09 (m, 1H), 4.23–4.67 (m, 3H), 4.95 (d, 1H, J=3.3), 6.16 (s, 1H), 7.45 (d, 2H, J=8.4), 7.81 (d, 2H, J=8.4). LRMS (ESI⁻) m/z: 360.0 (calc. for M–H⁺ $C_{16}H_{17}Cl_2FNO_3$ 360.0).

Example 59

Compound 74

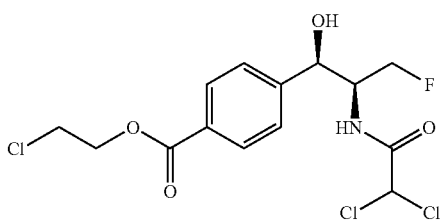

The carboxylic acid intermediate from the synthesis of 72 was dichloroacetylated as in the synthesis of 29. The resulting intermediate (95.8 mg, 0.297 mmol) was dissolved in 2 mL of MeOH, several drops of $H_2O$ were added and then a 20% (w/v) aqueous $Cs_2CO_3$ solution was added dropwise until the solution reached pH 7. The mixture was concentrated under vacuum. One drop of $Et_3N$ and 10 mL of 2-chloroethanol were added and the mixture stirred at 135° C. for 2 hours. Residual chloroethanol was removed under vacuum and the residue chromatographed. Compound 74 (13.3 mg) was the major product and 75 (9.2 mg) the minor product. $^1H$ NMR (300 MHz, $CD_3OD$): δ 3.78–3.82 (m, 2H), 4.23–4.68 (m, 5H), 4.97 (d, 1H, J=3.0), 6.17 (s, 1H), 7.46 (d, 2H, J=8.3), 7.93 (d, 2H, J=8.3). LRMS (ESI⁺) m/z: 407.9 (calc. for M+Na⁺ $C_{14}H_{15}Cl_3FNNaO_4$ 408.0).

Example 60

Compound 75

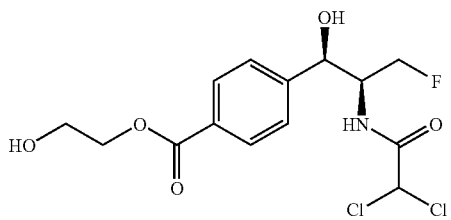

$^1H$ NMR (300 MHz, $CD_3OD$): δ 3.83–3.39 (m, 2H), 4.31–4.74 (m, 5H), 5.02 (d, 1H, J=3.3), 6.23 (s, 1H), 7.52 (d, 2H, J=8.4), 8.02 (d, 2H, J=8.4). LRMS (ESI⁻) m/z: 366.0 (calc. for M–H⁺ $C_{14}H_{15}Cl_2FNO_5$ 366.0).

Example 61

Compound 76

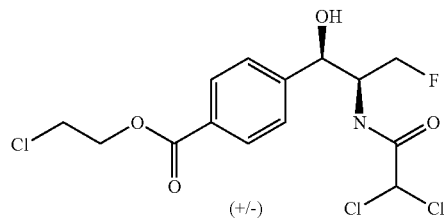

(+/−)

The cyclopropyl analog of intermediate 89 was prepared by a Stille coupling analogous to that used to synthesize 89. Acidic cleavage of the phenyloxazoline group resulted in the HCl-mediated opening of the cyclopropyl ring. This material was deprotected and dichloroacetylated to give 76. $^1H$ NMR (300 MHz, $CD_3OD$): δ 2.10–2.19 (m, 2H), 3.19 (t, 2H, J=7.1), 3.66 (t, 2H, J=6.6), 4.31–4.74 (m, 3H), 5.03 (d, 1H, J=3.3), 6.23 (s, 1H), 7.53 (d, 2H, J=8.3), 7.96 (d, J=8.3). LRMS (ESI⁻) m/z: 381.9 (calc. for M–H⁺ $C_{15}H_{16}Cl_3FNO_3$ 382.0).

Example 62

Compound 77

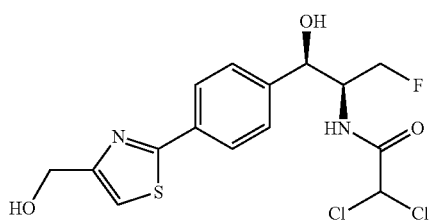

The thiazole ring of this analog was formed by conversion of the protected nitrile intermediate to the corresponding thioamide by reaction with H$_2$S in pyridine. The thioamide was then reacted with the appropriate protected α-halocarbonyl compound to form the substituted thiazole shown. Deprotection and dichloroacetylation was performed as for other compounds of this invention. $^1$H NMR (300 MHz, CD$_3$OD): δ 4.32–4.75 (m, 5H), 5.01 (d, 1H, J=3.3), 6.27 (s, 1H), 7.38 (s, 1H), 7.51 (d, 2H, J=8.3), 7.91 (d, 2H, J=8.3). LRMS (ESI$^-$) m/z: 390.9 (calc. for M–H$^+$ C$_{15}$H$_{14}$Cl$_2$FN$_2$O$_3$S 391.0).

Example 63

Compound 79

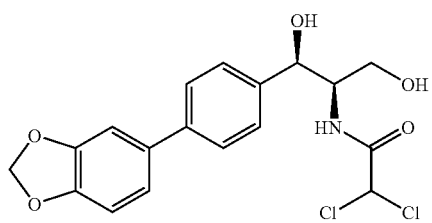

This compound was formed by Suzuki coupling method A from an intermediate in which the primary hydroxyl group was not converted to a fluoride. Deprotection and dichloroacetylation were performed as with other compounds of this invention. $^1$H NMR (300 MHz, CD$_3$OD): δ 3.55 (dd, 1H, J=11.0, 5.9), 3.77 (dd, 1H, J=11.0, 6.5), 4.07–4.11 (m, 1H), 5.02 (d, 1H, J=3.6), 5.96 (s, 2H), 6.29 (s, 1H), 6.86 (d, 1H, J=8.4), 7.05–7.07 (m, 2H), 7.40–7.50 (m, 4H). LRMS (ESI$^-$) m/z: 395.9 (calc. for M–H$^+$ C$_{18}$H$_{16}$Cl$_2$NO$_5$ 396.0).

Example 64

Compound 80

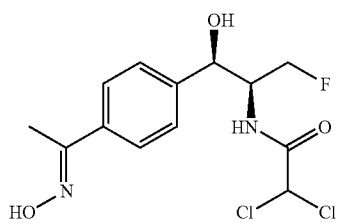

Compound 41 (11.5 mg, 0.0346 mmol) and hydroxylamine hydrochloride (2.8 mg, 0.0415 mmol) were stirred in EtOH (3 mL) for 12 hours and then refluxed for an additional 12 hours. The solvent was removed under vacuum and the product isolated as a single isomer (it was not determined whether the isomer was the cis or trans oxime). $^1$H NMR (300 MHz, CD$_3$OD): δ 2.21 (s, 3H), 4.26–4.68 (m, 3H,), 4.95 (d, 1H, J=3.9), 6.27 (s, 1H), 7.39 (d, 2H, J=8.3), 7.61 (d, 2H, J=8.3).

Example 65

Compound 81

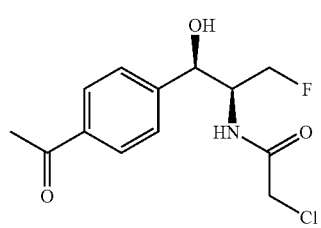

Free amine 37 (4.7 mg, 0.0224 mmol) was dissolved in MeOH (1 mL) and the mixture cooled to 0° C. Chloroacetic anhydride (5 drops) and triethylamine (5 drops) were added and the mixture warmed to room temperature and stirred for 2 hours. The solvent was removed under vacuum and the product purified by silica gel chromatography (2:3 EtOAc/hexanes) to give 3.3 mg (0.011 mmol) of product. $^1$H NMR (300 MHz, CD$_3$OD): δ 2.59 (s, 3H), 3.92–4.03 (m, 2H,), 4.29–4.68 (m, 3H), 5.02 (d, 1H, J=3.3), 7.53 (d, 2H, J=8.4), 7.96 (d, 2H, J=8.4).

Example 66

Compound 82

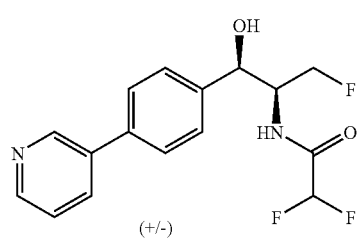

(+/−)

The biaryl intermediate was formed by Suzuki coupling method A using 22 and the appropriate boronic acid. $^1$H NMR (300 MHz, CD$_3$OD): δ 4.28–4.68 (m, 3H), 5.00 (d, 1H, J=4.2), 6.01 (t, 1H, J=54), 7.49–7.60 (m, 3H), 7.66 (d, 2H, J=8.4), 8.07–8.11 (m, 1H), 8.50 (dd, 1H, J=4.8, 1.5), 8.79–8.79 (m, 1H). LRMS (ESI$^-$) m/z: 322.9 (M–H$^+$ C$_{16}$H$_{14}$F$_3$N$_2$O$_2$ requires 323.1).

Example 67

Compound 84

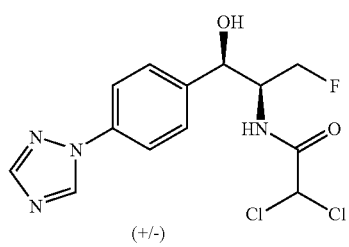

(+/-)

This compound was prepared by procedures analogous to those described in Schemes 2 and 3. The 4-(1,2,4-triazol-1-yl)phenylserine analog of 6 was synthesized by the same methods used to make 6. The required 4-(1,2,4-triazol-1-yl) benzaldehyde was prepared as described in the literature (Tanaka, A., et al., *J. Med. Chem.* 1998, 41, 2390–2410). $^1$H NMR (300 MHz, CD$_3$OD): δ 4.33–4.76 (m, 3H), 5.04 (d, 1H, J=3.3), 6.26 (s, 1H), 7.59 (d, 2H, J=8.6), 7.78 (d, 2H, J=8.6), 8.14 (s, 1H), 9.05 (s, 1H). LRMS (ESI$^-$) m/z: 345.0 (calc. for M–H$^+$ C$_{13}$H$_{12}$Cl$_2$FN$_4$O$_2$ 345.0).

Example 68

Compound 85

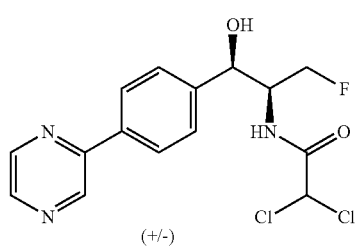

(+/-)

The biaryl intermediate was prepared from boronic acid 12 and 2-iodopyrazine. Deprotection and dichloroacetylation were accomplished as in the synthesis of 29. $^1$H NMR (300 MHz, CD$_3$OD): δ 4.32–4.75 (m, 3H), 5.04 (d, 1H, J=3.3), 6.27 (s, 1H), 7.57 (d, 2H, J=8.4), 8.05 (d, 2H, J=8.4), 8.51 (d, 1H, J=2.7), 8.65–8.66 (m, 1H), 9.08 (d, 1H, J=1.8). LRMS (ESI$^-$) m/z: 355.8 (calc. for M–H$^+$ C$_{15}$H$_{13}$Cl$_2$FN$_3$O$_2$ 356.0).

Example 69

Compound 86

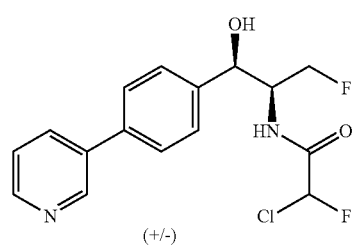

(+/-)

Same procedure as that for the synthesis of 68. $^1$H NMR (300 MHz, CD$_3$OD): δ 4.29–4.73 (m, 3H), 5.01 (br d, 1H, J=3.9), major diastereomer 6.49 (d, 1H, J=49.8), minor diastereomer 6.51 (d, 1H, J=49.8), 7.48–7.56 (m, 3H), 7.64–7.67 (m, 2H), 8.06–8.10 (m, 1H), 8.49–8.51 (m, 1H), 8.78–8.79 (m, 1H). LRMS (ESI$^-$) m/z: 338.9 (calc. for M–H$^+$ C$_{16}$H$_{14}$ClF$_2$N$_2$O$_2$ 339.1).

Example 70

Compound 87

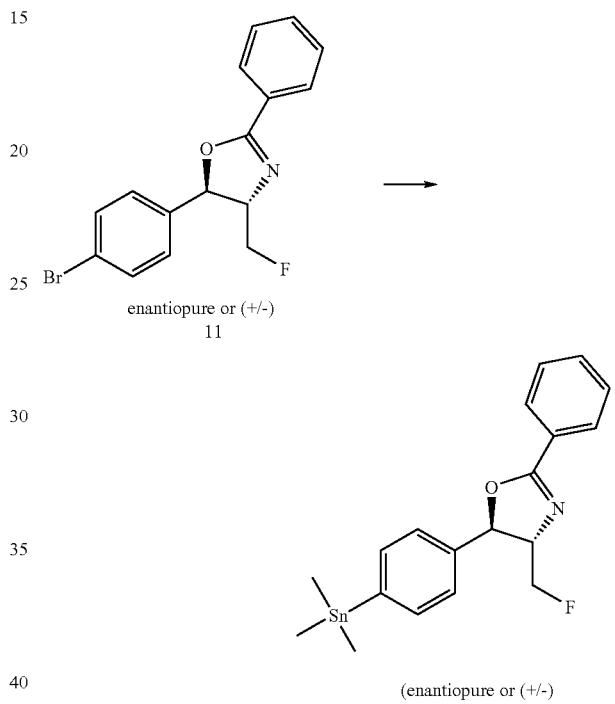

Compound 11 (0.496 g, 1.48 mmol) was dissolved in anhydrous benzene (15 mL) under N$_2$. The flask was fitted with a reflux condenser and a long needle was dropped through the condenser and the solution purged with a gentle stream of dry N$_2$ for 5 minutes. Hexamethylditin (0.58 g, 1.78 mmol) was added and the mixture purged for another 5 minutes. Pd(PPh$_3$)$_4$ (0.171 g, 0.148 mmol) was added and purging with N$_2$ continued. After 5 minutes, the needle was removed and a N$_2$ inlet was placed at the top of the reflux condenser. The mixture was refluxed for approximately 2 hours under N$_2$. Over the course of the reaction, the mixture turned from orange to yellow to black. The solvent was removed under vacuum and the product purified by chromatotron (silica gel, 1 mm plate) to give 440 mg of product as a clear oil. $^1$H NMR (300 MHz, CD$_3$OD): δ 0.27 (s, 9H—this resonance contains significant satellite peaks, which are due to NMR-active isotopes of tin), 4.27–4.41 (m, 1H), 4.59–4.76 (m, 2H), 5.60 (d, 1H, J=6.9), 7.33 (d, 2H, J=8.1), 7.45–7.31 (m, 5H), 7.99–8.02 (m, 2H).

Example 71

Compound 88

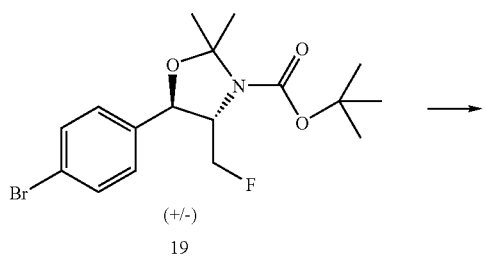

This compound was prepared in the same manner as 87. $^1$H NMR (300 MHz, CD$_3$OD): δ 0.027 (s, 9H, with significant satellite peaks caused by NMR-active tin isotopes), 1.49 (s, 9H), 1.55 (s, 3H), 1.67 (s, 3H), 3.73–3.83 (m, 1H), 4.30–4.49 (m, 2H), 5.06 (d, 2H, J=7.5), 7.36–7.51 (m, 4H).

Example 72

Compound 89

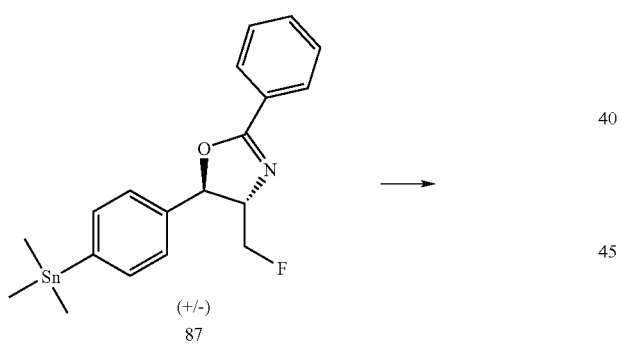

Compound 87 (36.5 mg, 0.0873 mmol) was dissolved in anhydrous THF under N$_2$. With stirring, K$_2$CO$_3$ (24 mg, 0.16 mmol) was added. The mixture was purged with a gentle stream of N$_2$ for 5 minutes. Et$_3$N (31 μL, 0.22 mmol) and cyclobutanecarbonyl chloride (13 μL, 0.11 mmol) were added and the mixture purged with N$_2$ for 5 minutes. Pd$_2$dba$_3$ was added, the mixture purged for 5 min and then stirred under N$_2$ for 3 hours. The mixture was diluted with EtOAc (25 mL) and H$_2$O (25 mL) and filtered through a cotton plug to remove solids. The EtOAc was washed with 1 N HCl (2×) and brine (2×), dried over Na$_2$SO$_4$ and concentrated under vacuum. The product was purified by chromatotron (silica plate, 1 mm, 1:4 EtOAc/hexanes) to give 16.9 mg (0.050 mmol) of product. LRMS (ESI$^+$) m/z: 338.2 (M+H$^+$ C$_{21}$H$_{21}$FNO$_2$ requires 338.2).

Example 73

Compound 90

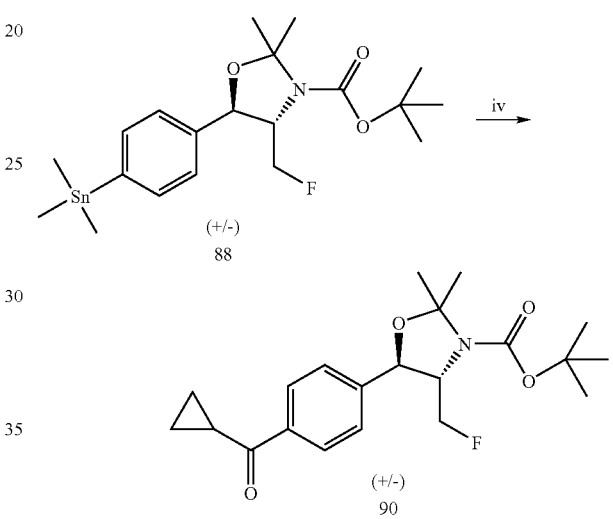

Same procedure as in the synthesis of 89. $^1$H NMR (300 MHz, CD$_3$OD): δ 0.027 (s, 9H, with significant satellite peaks caused by NMR-active tin isotopes), 1.49 (s, 9H), 1.55 (s, 3H), 1.67 (s, 3H), 3.73–3.83 (m, 1H), 4.30–4.49 (m, 2H), 5.06 (d, 2H, J=7.5), 7.36–7.51 (m, 4H).

Example 74

Compound 91

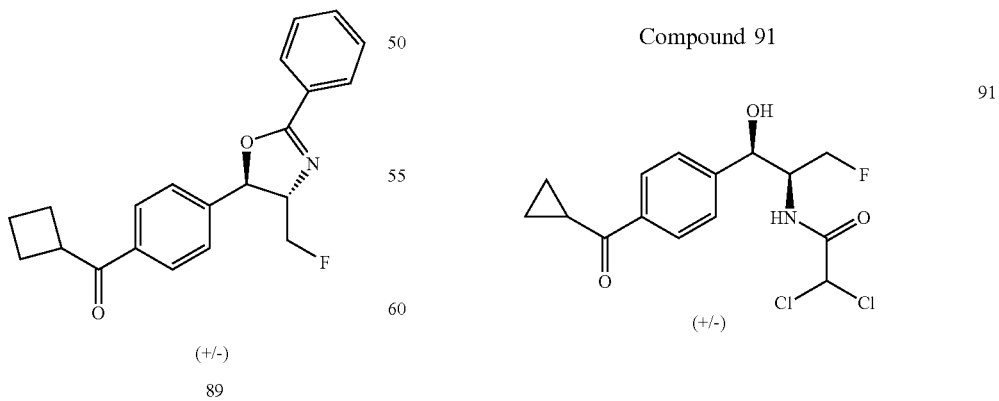

Compound 91 was deprotected by brief treatment of 90 with 9/1 TFA/H$_2$O. The dichloroacetyl group was introduced as in the synthesis of 29. LRMS (ESI$^-$) m/z: 345.8 (calc. for M–H$^+$ C$_{15}$H$_{16}$Cl$_2$FNO$_3$ 346.0).

Example 75

Compound 92

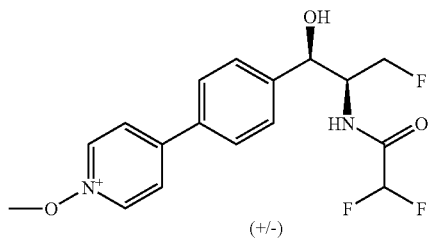

(+/-)

The same procedure as that used in the synthesis of 56 was employed. ¹H NMR (300 MHz, CD₃OD): δ 4.28–4.74 (m, 3H), 5.01 (d, 1H, J=3.9), 5.98 (t, 1H, J=53.8), 7.55 (d, 2H, J=8.4), 7.76 (d, 2H, J=8.4), 7.86 (d, 2H, J=7.1), 8.35 (d, 2H, J=7.1).

Example 76

Compound 93

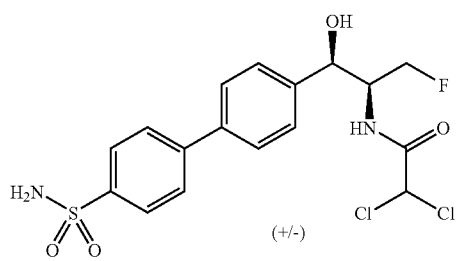

(+/-)

The biaryl intermediate was prepared by reaction of 23 and the appropriate bromide using Suzuki coupling A. Deprotection and dichloroacetylation were carried out as described above in the synthesis of 29. LRMS (ESI⁻) m/z: 433.0 (M–H⁺ $C_{17}H_{16}Cl_2FN_2O_4S$ requires 433.0).

Example 77

Compound 94

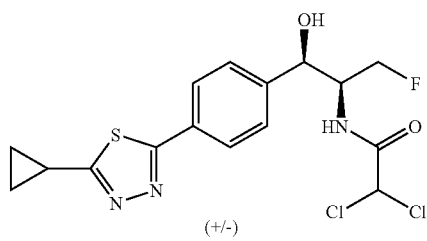

(+/-)

The biaryl intermediate was prepared by reaction of 23 with 2-amino-4-cyclopropyl-1,3,4-thiadiazole (prepared as in the synthesis of 24) using Suzuki coupling B. Deprotection was accomplished by brief treatment of the protected biaryl intermediate with 90/10 TFA/H₂O and dichloroacetylation was performed as in the synthesis of 29. ¹H NMR (300 MHz, CD₃OD): δ 1.12–1.31 (m, 4H), 2.46–2.52 (m, 1H), 4.30–4.75 (m, 3H), 5.02 (d, 1H, J=3.3), 6.24 (s, 1H), 7.54 (d, 2H, J=8.4), 7.87 (d, 2H, J=8.4).

Example 78

Compound 95

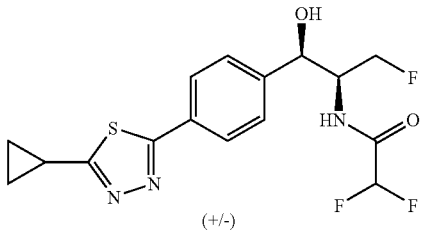

(+/-)

Same procedure as in the synthesis of 94 using methyl difluoroacetate in place of methyl dichloroacetate. ¹H NMR (300 MHz, CD₃OD): δ 1.13–1.15 (m, 2H), 1.28–1.32 (m, 2H), 2.47–2.52 (m, 1H), 4.29–4.70 (m, 3H), 5.01 (d, 1H, J=4.2); 5.98 (t, 1H, J=53.7), 7.54 (d, 2H, J=8.7), 7.88 (d, 2H, J=8.7). LRMS (ESI⁻) m/z: 370.0 (M–H⁺ $C_{16}H_{15}F_3N_3O_2S$ requires 370.1).

Example 79

Compound 97

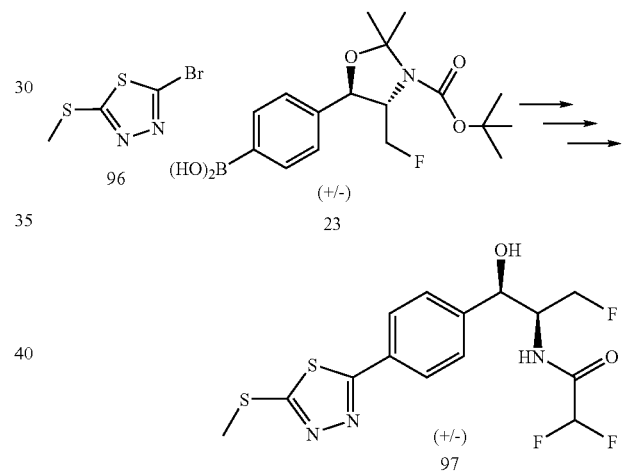

Compound 96 was prepared in analogous fashion to 24. Compound 97 was prepared in analogous fashion to 48. Suzuki coupling method B was used, followed by deprotection and difluoroacetylation. LRMS (ESI⁻) m/z: 376.0 (M–H⁺ $C_{14}H_{13}F_3N_3O_2S_2$ requires 376.0)

Example 80

Compound 98

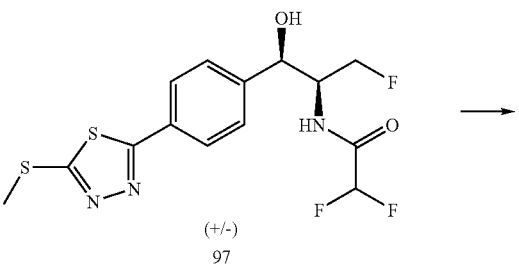

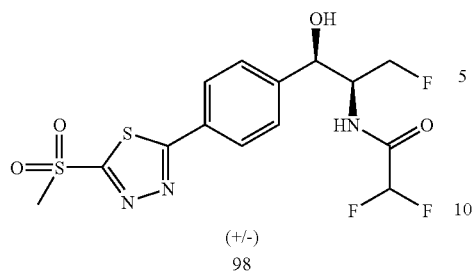

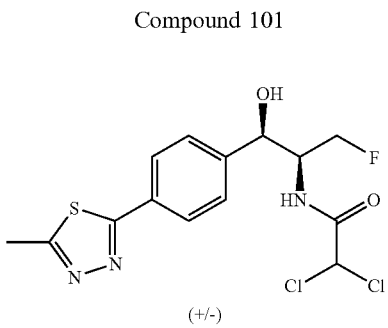

Example 82

Compound 101

Compound 101 was prepared using the same procedure as in the synthesis of 100 but with methyldichloroacetate in place of methyldifluoroacetate. $^1$H NMR (300 MHz, CD$_3$OD): δ 2.79 (s, 3H), 4.31–4.75 (m, 3H), 5.03 (d, 1H, J=3.0), 6.24 (s, 1H), 7.55 (d, 2H, J=8.4), 7.89 (d, 2H, J=8.4).

Compound 97 (11.1 mg or 0.0294 mmol) was dissolved in 5 mL of CH$_2$Cl$_2$, with stirring at room temperature. To this was added m-CPBA (36 mg, 0.147 mmol). The mixture was stirred for 23 hours. Attempted Chromatotron (1 mm plate) purification, eluting with 80:20 then 70:30 then 50:50 hexanes/EtOAc, failed to remove m-CPBA-related materials. Thus, material from the Chromotron was subjected to C-8 reversed-phase HPLC, which gave 8.8 mg (0.021 mmol) of 98. $^1$H NMR (300 MHz, CD$_3$OD): δ 3.52 (s, 3H), 4.34–4.72 (m, 3H), 5.05 (d, 1H, J=3.6), 5.97 (t, 1H, J=53.9), 7.61 (d, 2H, J=7.61), 8.05 (d, 2H, J=8.1).

Example 83

Compound 102

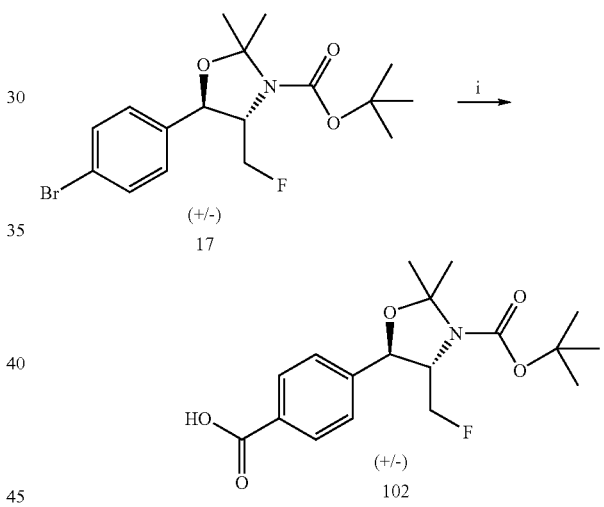

Example 81

Compound 100

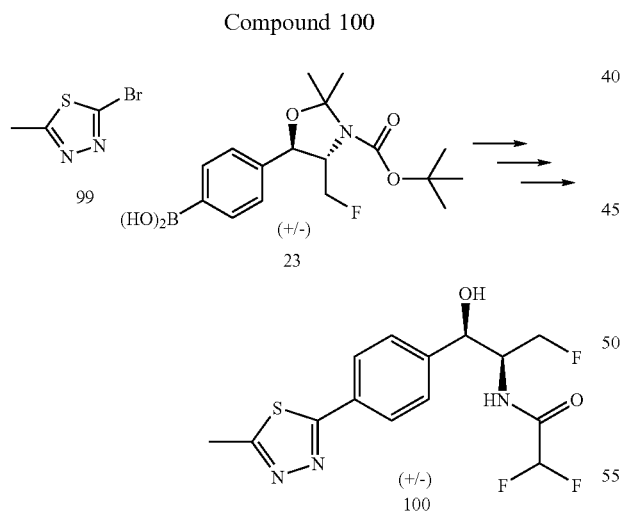

Compound 99 was prepared in analogous fashion to 24 and 100 was prepared in analagous fashion to 48. Suzuki coupling method B was used followed by deprotection and difluoroacetylation. $^1$H NMR (300 MHz, CD$_3$OD): δ 2.80 (s, 3H), 4.30–4.70 (m, 3H), 5.01 (d, 1H, J=3.6), 5.98 (t, 1H, J=53.9), 7.55 (d, 2H, J=8.4), 7.91 (d, 2H, J=8.3).

Compound 17 (100 mg, 0.258 mmol) was placed in a dry round-bottom flask equipped with a stir bar. The flask was charged with 5 mL of dry THF and the contents cooled to −78° C. under N$_2$. With rapid stirring, n-BuLi (1.30 M in hexanes, 0.322 mmol, 0.248 mL) was added, which produced a clear brown/yellow solution. The mixture was stirred for an additional 10 minutes. Excess CO$_2$, generated by sublimation of dry ice, was passed though a drying tube charged with Drierite and bubbled directly into the −78° C. mixture, now equipped with a venting needle in the septum to prevent buildup of CO$_2$ pressure. The mixture was warmed to room temperature and stirred an additional 30 minutes by which time it was clear yellow and TLC indicated a product had formed. The mixture was quenched by addition of 10% (v/w) aqueous NH$_4$Cl (5 drops), producing a cloudy yellow suspension. The mixture was concentrated under vacuum and re-suspended in EtOAc (50 mL) and enough 10% aqueous citric acid to produce a biphasic mixture having a pH of 2.5. The layers were separated and the EtOAc layer was washed with brine (1×10 mL). The mixture was dried over Na₂SO₄, filtered and evaporated to give 105 mg of yellow oil. The product was isolated by chromatotron (1 mm plate eluting with 4:1 hexanes/EtOAc to 65:35 hexanes/EtOAc to 1:1 hexanes/EtOAc to 2% MeOH in CH₂Cl₂ to 5% MeOH in CH₂Cl₂ and, finally, 10% MeOH in CH₂Cl₂ to which several drops of acetic acid had been added). The appropriate fractions were combined, diluted with toluene and evaporated to give 67.5 mg (0.191 mmol) of 102. ¹H NMR (300 MHz, CD₃OD): δ 1.49 (s, 9H), 1.57 (S, 3H), 1.69 (s, 3H), 3.77–3.90 (m, 1H), 4.39–4.57 (m, 1H), 4.90–5.10 (br s, 1H), 5.18 (d, 1H, J=7.2), 7.56 (d, 2H, J=8.1), 8.04 (d, 2H, J=8.1). LRMS (ESI⁻) m/z: 352 (M−H⁺ $C_{18}H_{23}FNO_5$ requires 352).

Example 84

Compound 106

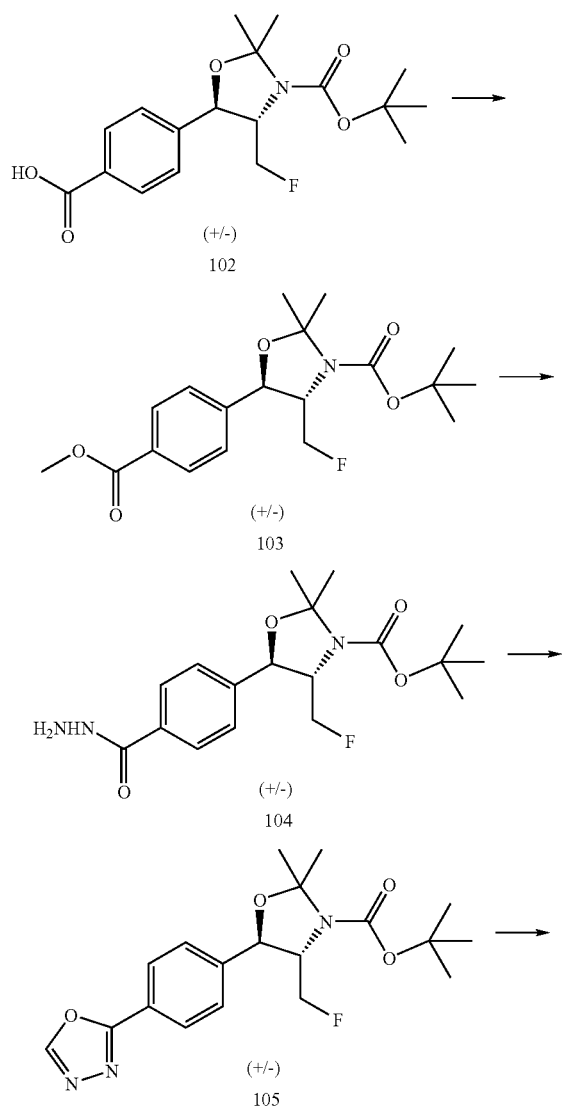

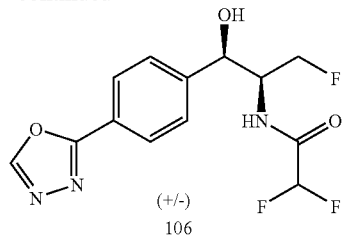

Compound 102 (106 mg, 0.299 mmol) was dissolved in EtOAc and diazomethane, generated using an Aldrich Chemical Company diazomethane kit, was added dropwise until a slight yellow color persisted. Excess of diazomethane was allowed to evaporate overnight in a well-ventilated fume hood, and the remaining EtOAc solution was concentrated under vacuum. The residue was dissolved in Et₂O and washed with aqueous NaHCO₃ and then brine. The layers were separated and the organic layer was dried over anhydrous Na₂SO₄, filtered and concentrated to give 0.087 g (0.24 mmol, 79%) of methyl ester 103, which was used without further purification or characterization.

Compound 103 (0.037g, 0.136 mmol) was dissolved in 1 mL of EtOH. To this was added hydrazine hydrate (0.007 g, 0.177 mmol). The mixture was refluxed for 12 hours. The solvent was removed under vacuum and the product purified by chromatotron (1 mm plate, 10% MeOH in CH₂Cl₂). Compound 104 was isolated (40.0 mg, 0.109 mmol) and was used without further characterization. LRMS (ESI⁻) m/z: 366 (M−H⁺ $C_{18}H_{25}FN_3O_4$ requires 366).

Compound 104 (0.050 g, 0.133 mmol) was dissolved in 5 mL of triethyl orthoformate and stirred at 120° C. for 24 hours. The mixture was evaporated to give 26 mg of crude 105, which was used without further characterization or purification.

Compound 105 (0.0051 g, 0.014 mmol) was stirred at room temperature with 10 mL of 9:1 TFA/H₂O for 10 minutes. The mixture was concentrated under vacuum, dissolved three times in a MeOH/toluene mixture, the solvents being evaporated each time, and dried to a constant weight to give 0.5 mg of deprotected material. The residue was dissolved in 1 mL of MeOH in an open container and 5 drops of methyl difluoroacetate and 15 drops of Et₃N were added. The mixture was stirred at room temperature for 12 hours. After 12 hours, TLC indicated a single product. The mixture was concentrated under vacuum and the product isolated by silica gel chromatography eluting with 20:1 CH₂Cl₂/CH₃OH to give 2.3 mg of 106. ¹H NMR (300 MHz, CD₃OD): δ 4.31–4.74 (m, 3H), 5.04 (d, 1H, J=3.9), 5.96 (t, 1H, J=53.9), 7.61 (d, 2H, J=8.4), 8.05 (d, 2H, J=8.4), 8.99 (d, 1H). LRMS (ESI⁻) m/z: 314 (M−H⁺ $C_{13}H_{11}F_3N_3O_3$ requires 314).

Example 85

Compound 107

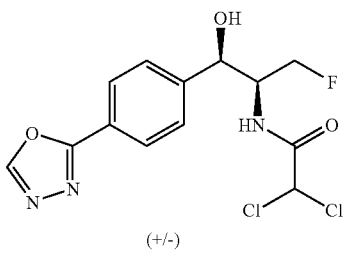

Compound 107 was prepared in analogous manner to 106 using methyl dichloroacetate in place methyl difluoroacetate. $^1$H NMR (300 MHz, CD$_3$OD): δ 4.32–4.80 (m, 3H), 5.06 (d, 1H, J=3.0), 6.23 (S, 1H), 7.62 (d, 2H, J=8.4), 8.03 (d, 2H, J=8, 4), 8.98 (s, 1H). LRMS (ESI$^-$) m/z: 346 (M–H$^+$ C$_{13}$H$_{11}$Cl$_2$FN$_3$O$_3$ requires 346).

Example 86

Compound 108

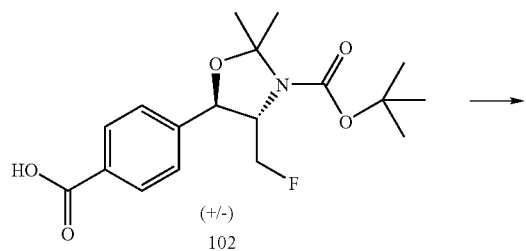

Compound 102 (32.7 mg, 0.0925 mmol) was dissolved in EtOAc (8 mL) and cooled with stirring to 0° C. Pentafluorophenol (17 mg, 0.093 mmol) was added. Once all solids had dissolved, DCC (19 mg, 0.093 mmol) was added and the mixture stirred at 0° C. for 1.25 hours. The mixture was evaporated to one-quarter the original volume at which time a DCU precipitate formed. The DCU was removed by filtration and the pentafluorophenyl ester was isolated by evaporation. The residue was dissolved in 4 mL of MeOH and cooled to 0° C. with stirring. NaBH$_4$ (18 mg, 0.46 mmol) was added portionwise. When bubbling ceased, the mixture was warmed to room temperature. After 2 hour, excess NaBH$_4$ was quenched by addition of 4 drops of glacial HOAc. The mixture was evaporated to dryness and the residue partitioned between 1N aq. HCl and EtOAc. The EtOAc was separated and washed with 1 N aqueous HCl (2×15 mL), saturated aqueous NaHCO$_3$ (2×10 mL) and finally brine (1×25 mL). The EtOAc layer was dried over anhydrous Na$_2$SO$_4$, filtered, and evaporated to give 50 mg of yellow oil. Chromatotron purification (1 mm plate, eluting with 5% EtOAc in hexanes to 10% EtOAc in hexanes) gave 108 (10.3 mg, 0.030 mmol). $^1$H NMR (300 MHz, CD$_3$OD): δ 1.49 (s, 9H), 1.57 (s, 3H), 1.68 (s, 3H), 3.75–3.89 (m, 1H), 3.90 (s, 2H), 4.39–4.58 (m, 1H), 4.90–5.05 (br s, 1H), 5.19 (d, 1H, J=7.2), 7.57 (d, 2H, J=8.3), 8.04 (d, 2H, J=8.3).

Example 87

Compound 109

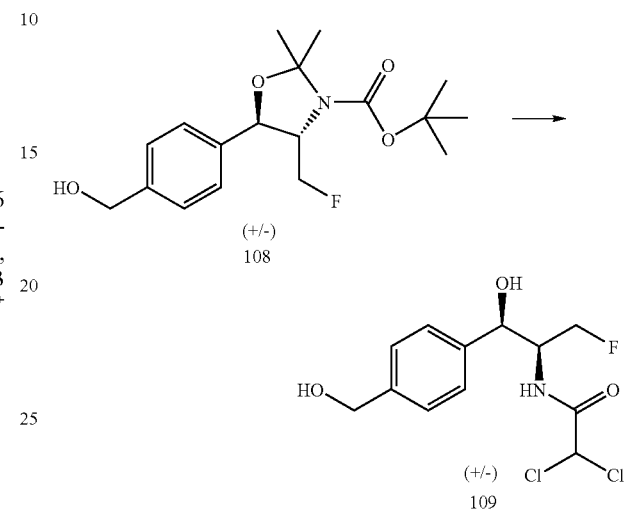

Compound 108 (10 mg, 0.30 mmol) was dissolved in 5 mL of 9:1 TFA/H$_2$O and stirred at room temperature for 1 hour. The mixture was then concentrated under vacuum to give approximately 9 mg of deprotected material as the TFA salt. $^1$H NMR (300 MHz, CD$_3$OD): δ 3.54–3.68 (m, 1H), 3.91 (s, 2H), 4.24–4.67 (m, 2H), 4.90 (d, 1H, solvent obscured), 7.57 (d, 2H, J=8.4), 8.07 (d, 2H, J=8.4).

The 9 mg of material (0.03 mmol) were dissolved in 2 mL of MeOH in an open container. To this was added 15 drops of Et$_3$N and 15 drops of methyl dichloroacetate. The mixture was stirred for 56 hour at room temperature. By the end of the reaction the solvent had completely evaporated. The residue was loaded onto a chromatotron (1 mm plate, eluting with 2% MeOH in CH$_2$Cl$_2$ to 4% MeOH in CH$_2$Cl$_2$, providing 7.5 mg of 109. $^1$H NMR (300 MHz, CD$_3$OD): δ 3.88 (s, 2H), 4.28–4.73 (m, 3H), 5.02 (d, 1H, J=3.3), 6.22 (s, 1H), 7.51 (d, 2H, J=8.4), 7.97 (d, 2H, J=8.4).

Example 88

Compound 110

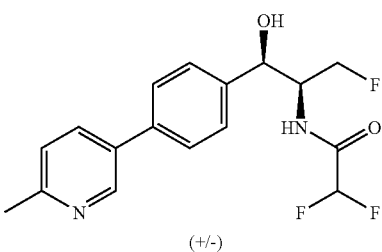

Prepared in analogous fashion to other pyridine-containing biaryl compounds herein. $^1$H NMR (300 MHz, CD$_3$OD): δ 2.54 (s, 3H), 4.30–4.68 (m, 3H), 4.99 (d, J=3.3), 5.98 (t, 1H, J=40.5), 7.35 (d, 1H, J=6.0), 7.49 (d, 2H, J=6.2), 7.61 (d, 2H, J=6.2), 7.95 (dd 1H, J=6.0, 1.7), 8.61 (d, 1H, J=1.7). LRMS (ESI⁻) m/z: 336.9 (M–H⁺ $C_{17}H_{16}F_3N_2O_2$ requires 337.1).

Example 89

Compound 111

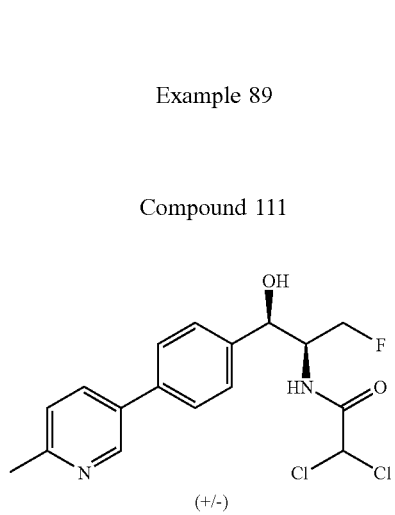

Prepared in analogous fashion to other pyridine-containing biaryl compounds herein. ¹H NMR (300 MHz, CD₃OD): δ 2.56 (s, 3H), 4.30–4.74 (m, 3H), 5.01 (d, 1H, J=3.9), 6.27 (s, 1H), 7.36 (d, 1H, J=8.1), 7.56 (d, 2H, J=8.4), 7.61 (d, 2H, J=8.4), 7.96 (1H, dd, J=8.1, 2.3), 8.62 (d, 1H, J=2.31).

Example 90

Compound 112

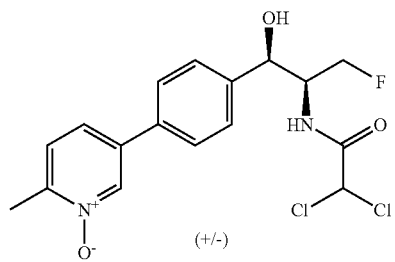

Compound 111 (0.0185 g, 0.0499 mmol) was dissolved in 10 mL CH₂Cl₂ at 0° C. To this was added m-CPBA (0.246 g, 0.0997 mmol). The mixture was stirred until the ice bath melted and the mixture came to room temperature, approximately 12 hours. The mixture was concentrated under vacuum and 112 was isolated by preparative plate silica gel chromatography (15% MeOH in CH₂Cl₂) followed by a silica gel plug (3% MeOH in CH₂Cl₂). LRMS (ESI⁻) m/z: 385 (M–H⁺ $C_{17}H_{16}Cl_2FN_2O_3$ requires 385.1).

Example 91

Compound 113

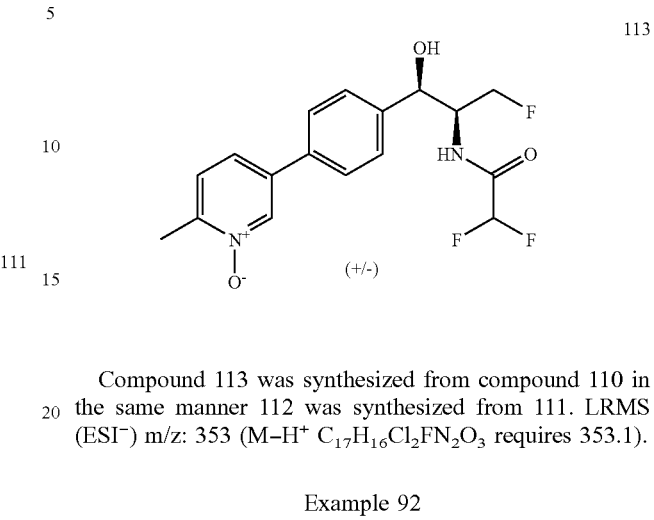

Compound 113 was synthesized from compound 110 in the same manner 112 was synthesized from 111. LRMS (ESI⁻) m/z: 353 (M–H⁺ $C_{17}H_{16}Cl_2FN_2O_3$ requires 353.1).

Example 92

Compound 114

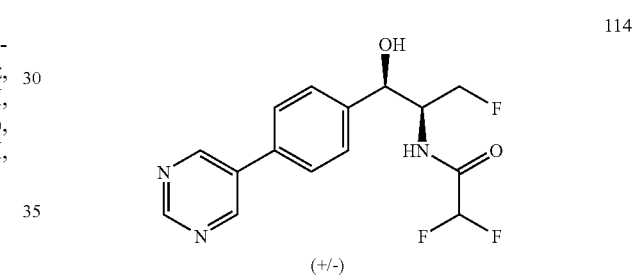

This compound was prepared in the same manner as other biaryls herein. LRMS (ESI⁻) m/z: 324 (M–H⁺ $C_{15}H_{13}F_3N_3O_2$ requires 324.1).

Example 93

Compound 115

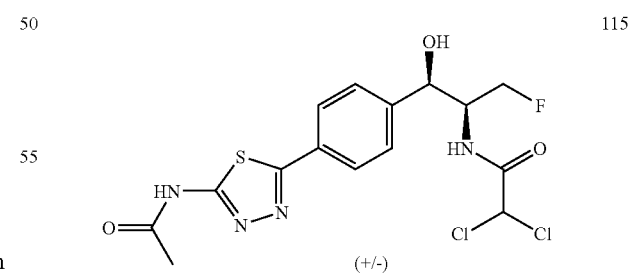

Prepared in same manner as compound 48. The required aryl bromide was prepared in two steps from 2-amino-1,3,4-thiadiazole by bromination with Br₂ followed by acetylation. LRMS (ESI⁻) m/z: 419 (M–H⁺ $C_{15}H_{14}Cl_2FN_4O_3S$ requires 419.0).

Example 94

Compound 116

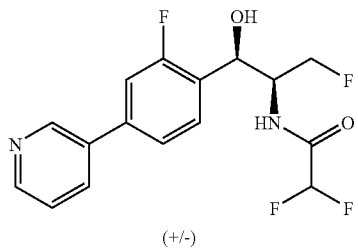

(+/-)

Compound 116 was synthesized as set forth in Schemes 2 and 3. The phenylserine analog was obtained by condensation of 4-bromo-2-fluorobenzaldehyde with glycine. Suzuki coupling method B was used to couple the bromide intermediate with m-pyridineboronic acid. Deprotection and difluoroacetylation were carried out as described previously herein. LRMS (ESI$^+$) m/z: 343 (M+H$^+$ $C_{16}H_{15}F_4N_2O_2$ requires 343.1).

Example 95

Compound 117

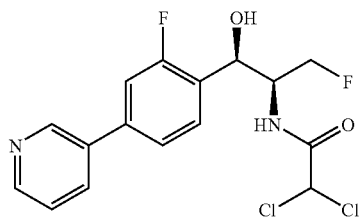

Same procedure as that used for the synthesis of 116. LRMS (ESI$^+$) m/z: 375 (M+H$^+$ $C_{16}H_{15}F_4N_2O_2$ requires 375.1).

Example 96

Compound 118

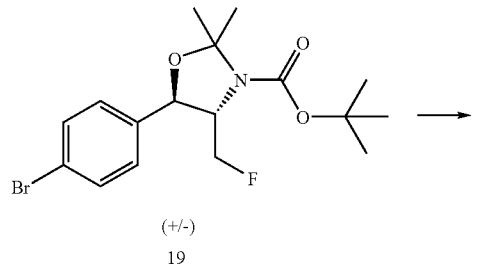

(+/-)
19

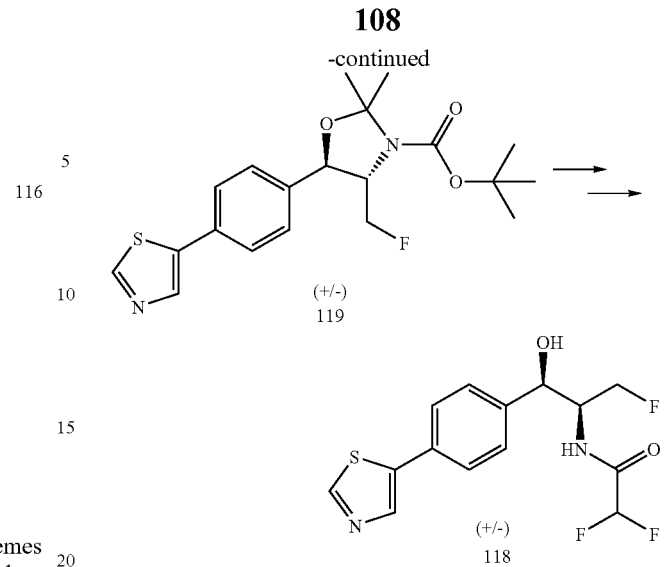

(+/-)
119

(+/-)
118

Compound 19 (100 mg, 0.258 mmol), potassium acetate (38 mg, 0.386 mmol), and 2 mL of N,N'-dimethylacetamide (DMAC) were combined in a glass pressure tube. Thiazole (112 mg, 1.31 mmol) was added by syringe, and the syringe rinsed with an additional 1 mL of DMAC, which was added to the pressure tube. The mixture was stirred at room temperature while purging with N$_2$ for 10 minutes. Pd(PPh$_3$)$_4$ (15 mg, 0.013 mmol) was added, the mixture purged with N$_2$ for 5 minutes, the tube sealed and heated to 150° C. behind a blast shield and held at that temperature for 12 hours. The mixture became dark brown. After cooling to room temperature, the contents of the tube were filtered through a pad of Celite and the filtrate evaporated to dryness. The residue was dissolved in 40 mL of 3:1 EtOAc/hexanes and washed with H$_2$O (2×15 mL) and brine (2×15 mL) and then dried over anhydrous Na$_2$SO$_4$. The dried organic layer was filtered to remove the drying agent and concentrated under vacuum to give 109 mg of brown oil. Compound 119 was purified by silica gel chromatography eluting with 80:20 to 50:50 hexanes/EtOAc (54 mg, 0.14 mmol). LRMS (ESI$^+$) m/z: 393.1 (M+H$^+$ $C_{20}H_{26}FN_2O_3S$ requires 393.2).

All of compound 119 was dissolved in 9:1 (v/v) TFA/H$_2$O (7.5 mL) and stirred at room temperature for 30 minutes. The mixture was then concentrated under vacuum and the residue dissolved twice in a mixture of toluene and methanol, the solvents being evaporated each time. A portion of the product (9.7 mg, 0.027 mmol) was dissolved in 2 mL of MeOH and 10 drops of Et$_3$N and 12 drops of methyl difluoroacetate were added. The mixture was left open to the air and stirred rapidly for 16 hours. The mixture was evaporated to dryness and the residue purified by chromatotron (1 mm plate) eluting with 3% MeOH in CH$_2$Cl$_2$ to give 118 (6.0 mg, 0.018 mmol. $^1$H NMR (300 MHz, CD$_3$OD): δ 4.27–4.69 (m, 3H), 4.97 (d, 1H, J=4.2), 5.99 (t, 1H, J=53.9), 7.47 (d, 2H, J=8.3), 7.65 (d, 2H, J=8.3), 8.16 (s, 1H), 8.94 (s, 1H). LRMS (ESI$^+$) m/z: 331.1 (M+H$^+$ $C_{14}H_{14}F_3N_2O_2S$ requires 331.1).

Example 97

Compound 120

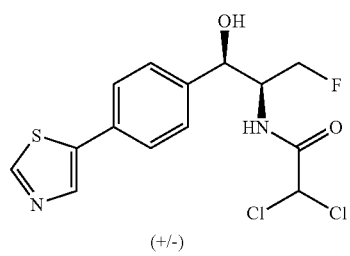

(+/-)

Compound 120 was prepared in a manner analogous to that used to prepare 118 using dichloroacetylation instead of difluoroacetylation. LRMS (ESI$^+$) m/z: 363.0 (M+H$^+$ C$_{14}$H$_{14}$Cl$_2$FN$_2$O$_2$S requires 363.0).

Example 98

Compound 121

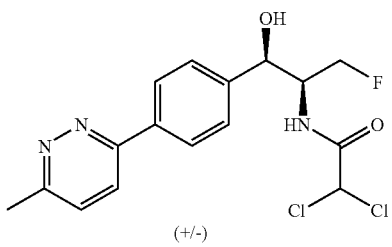

(+/-)

The protected biaryl intermediate was synthesized by Suzuki coupling method B from 23 and 3-chloro-6-methylpyridazine. Deprotection and dichloroacetylation were performed as for other compounds of this invention. LRMS (ESI$^+$) m/z: 372.0 (M+H$^+$ C$_{16}$H$_{17}$Cl$_2$FN$_3$O$_2$ requires 372.1).

Example 99

Compound 122

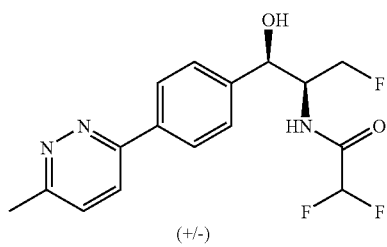

(+/-)

Prepared in analogous fashion to 121. LRMS (ESI$^+$) m/z: 340.1 (M+H$^+$ C$_{16}$H$_{17}$F$_3$N$_3$O$_2$ requires 340.1).

Example 100

Compound 123

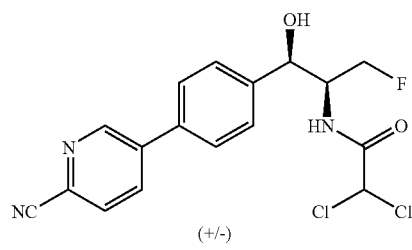

(+/-)

The protected biaryl intermediate was prepared by Suzuki coupling method B from boronic acid 23 and the appropriate aryl bromide. This intermediate was then deprotected by brief treatment with 9:1 (v/v) TFA/H$_2$O and dichloroacetylated as described for 29. LRMS (ESI$^+$) m/z: 380.0 (M-H$^+$ C$_{17}$H$_{13}$Cl$_2$FN$_3$O$_2$ requires 380.0).

Example 101

Compound 124

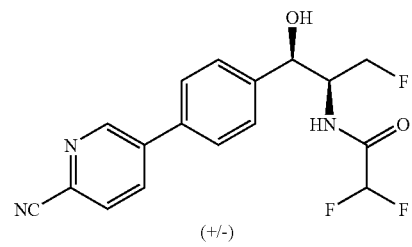

(+/-)

Prepared in analogous fashion to 123. Difluoroacetylation was performed as with other compounds of this invention. LRMS (ESI$^+$) m/z: 348.0 (M+H$^+$ C$_{17}$H$_{13}$F$_3$N$_3$O$_2$ requires 348.1).

Example 102

Compound 125

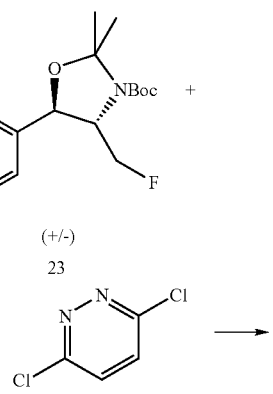

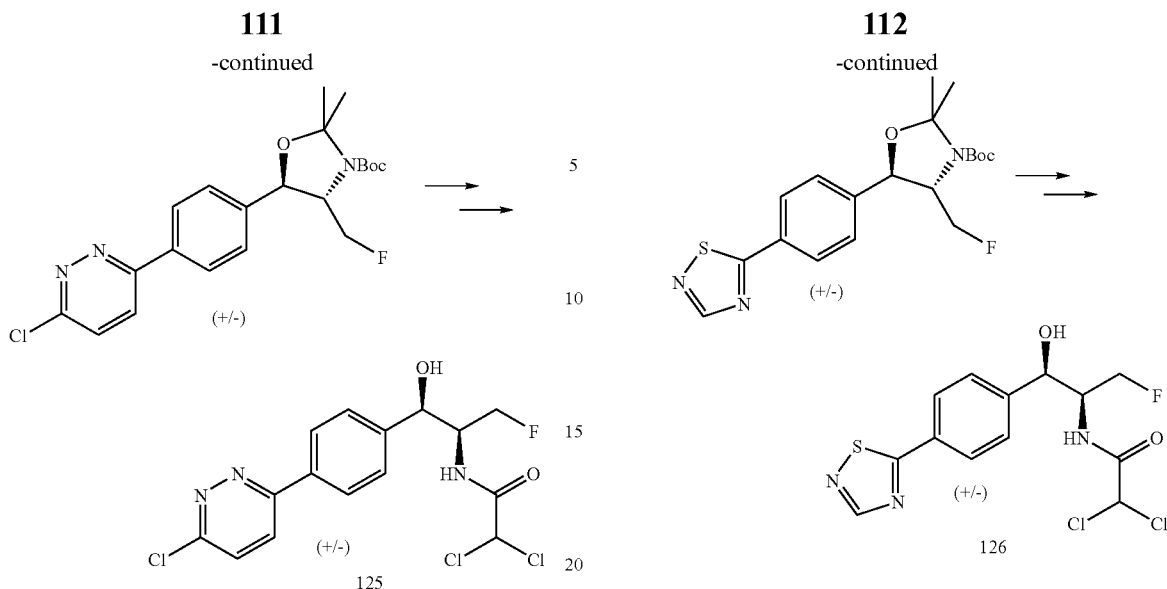

The biaryl intermediate was prepared from boronic acid 23 using Suzuki coupling. LRMS (ESI⁺) m/z: 392.0 (M–H⁺ $C_{15}H_{13}Cl_3FN_3O_2$ requires 392.0).

The starting nitrile was prepared from 35 by analogy to the preparation of bromo intermediate 19. Treatment with $Ph_2P(S)SH$ gave the thiobenzamide which was converted to the thiobenzamidine intermediate by reaction with dimethylformamide dimethylacetal. Cyclization with hydroxylamine-O-sulfonic acid in methanol/pyridine gave the biaryl intermediate. LRMS (ESI⁺) m/z: 364.0 (M–H⁺ $C_{13}H_{12}Cl_2FN_3O_2S$ requires 364.0)

Example 103

Compound 126

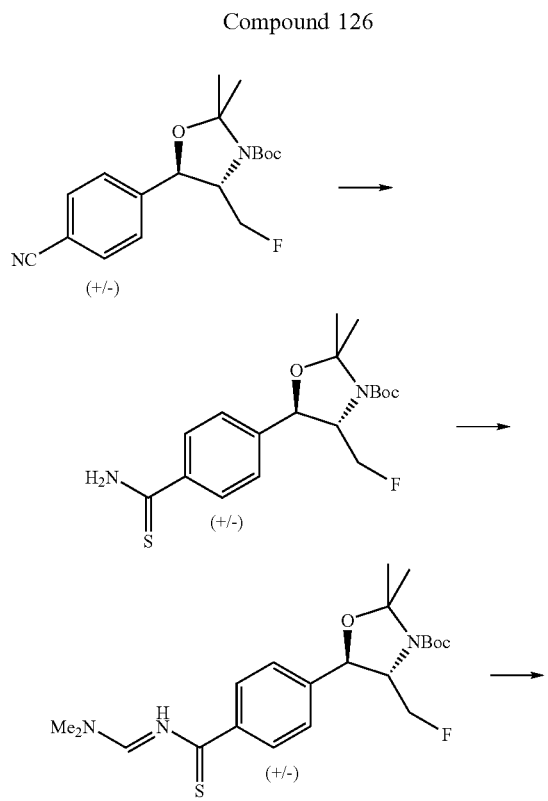

Example 104

Compound 127

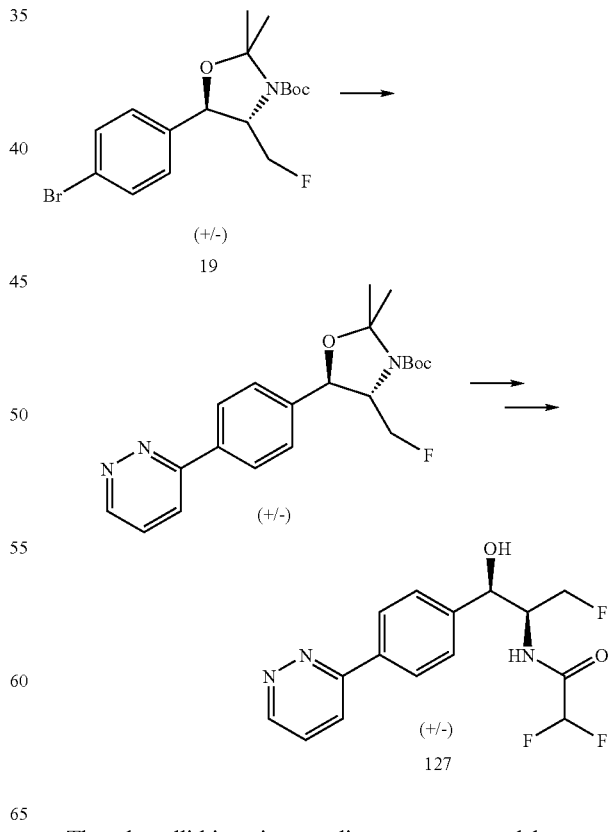

The phenyllithium intermediate was prepared by treatment of intermediate 19 with n-butyllithium in THF at −78°

C. The intermediate was reacted with pyridazine and the mixture of the resulting 2- and 3-position adducts was oxidized with DDQ. The desired 3-pyridazyl regioisomer was isolated by chromatography. LRMS (ESI⁺) m/z: 326.0 (M–H⁺ $C_{15}H_{14}F_3N_3O_2$ requires 326.0)

Example 105

Compound 128

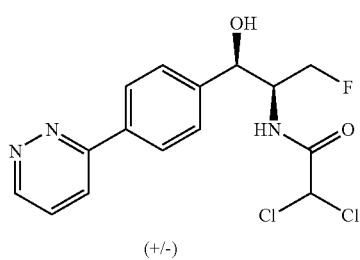
(+/-)

Compound 128 was synthesized using the procedure in Example 104. LRMS (ESI⁺) m/z: 358.0 (M–H⁺ $C_{15}H_{14}Cl_2FN_3O_2$ requires 358.0)

Example 106

Compound 129

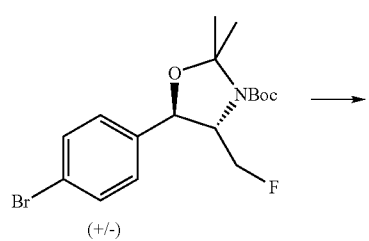

The procedure discussed in Example 104 was used. LRMS (ESI⁺) m/z: 358.0 (M–H⁺ $C_{15}H_{14}Cl_2FN_3O_2$ requires 358.0)

Example 107

Compound 130

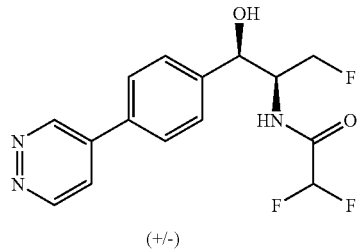
(+/-)

The procedure of Example 104 was used. LRMS (ESI⁺) m/z: 326.0 (M–H⁺ $C_{15}H_{14}F_3N_3O_2$ requires 326.0)

Example 108

Compound 131

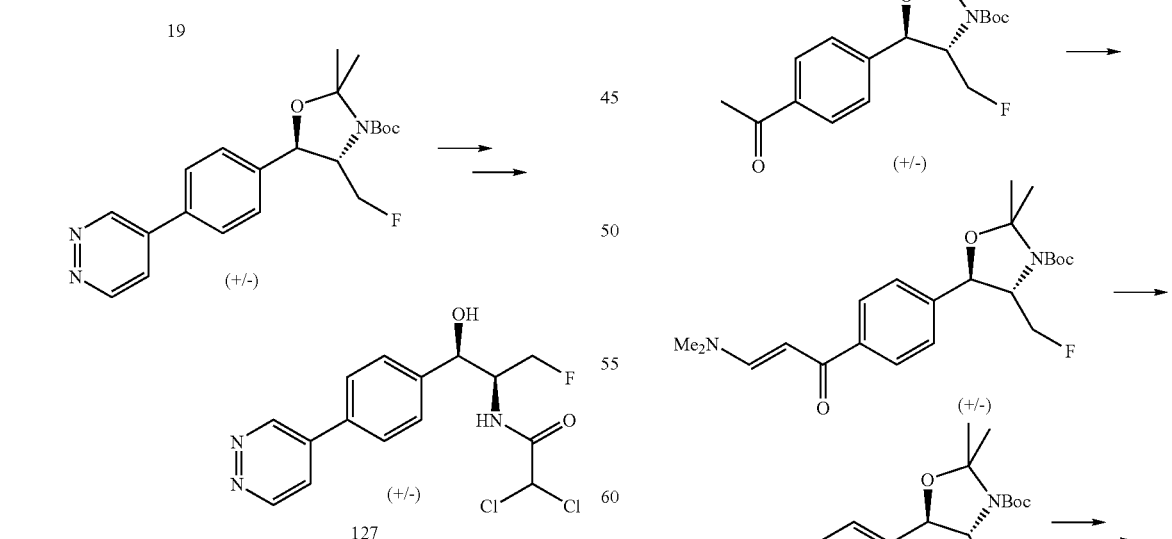

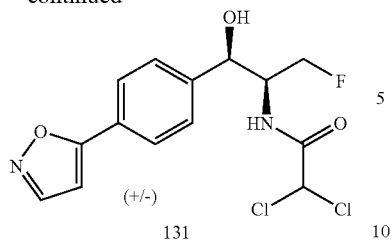
131 (+/-)

The phenyllithium intermediate was reacted with N-methoxy-N-methylacetamide and the resulting acetophenone was reacted with dimethylformamide dimethylacetal and hydroxylamine-O-sulfonic acid in methanol in presence of pyridine to give the isoxazole. LRMS (ESI$^+$) m/z: 347.0 (M–H$^+$ $C_{14}H_{13}Cl_2N_2O_3$ requires 347.0)

Example 109

Compound 132

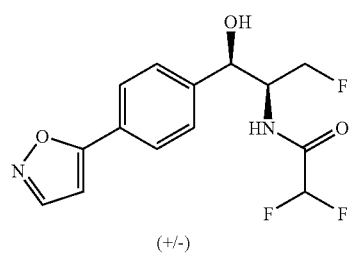
(+/-)

Compound 132 was synthesized using the procedure in Example 108. LRMS (ESI$^+$) m/z: 315.0 (M–H$^+$ $C_{14}H_{13}F_3N_2O_3$ requires 315.0.

Example 110

Compound 133

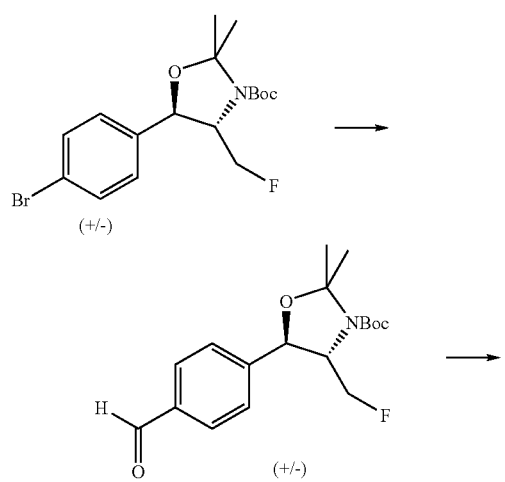

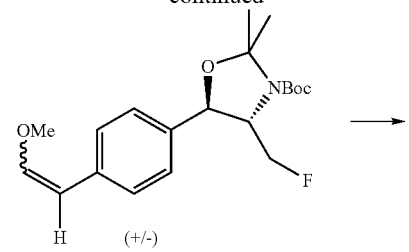

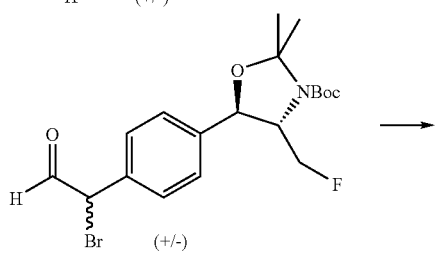

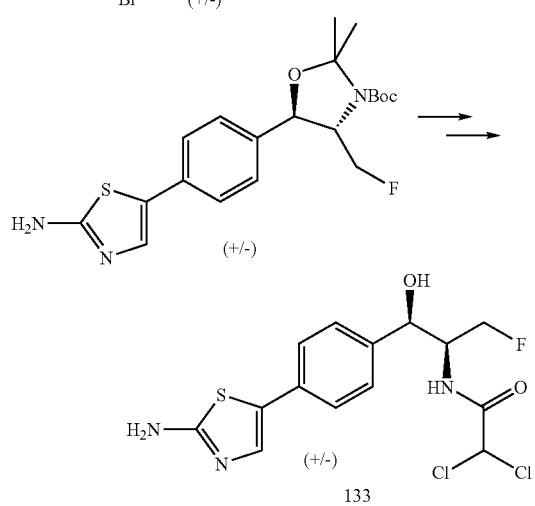
133

The phenyllithium intermediate was reacted with dimethylformamide to give the formyl intermediate which was then reacted with the ylide generated from methoxymethyltriphenyl phosphonium bromide. The resulting enol ether was brominated with bromine to give the bromoaldehyde. Cyclization with thiourea gave the aminothiazole. LRMS (ESI$^+$) m/z: 378.0 (M–H$^+$ $C_{14}H_{14}Cl_2FN_3O_2S$ requires 378.0)

Example 111

Compound 134

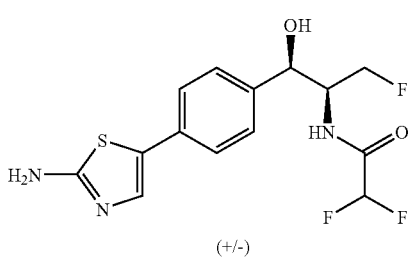
(+/-)

Compound 134 was synthesized using the procedure in Example 110. LRMS (ESI$^+$) m/z: 346.0 (M–H$^+$ $C_{14}H_{14}F_3N_3O_2S$ requires 346.0)

Example 112

Compound 135 (Mixture of Diastereoisomers)

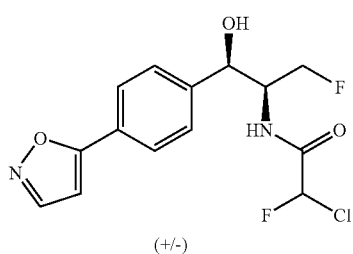

(+/−)

Compound 135 was synthesized using the procedure in Example 108. LRMS (ESI$^+$) m/z: 331.0 (M−H$^+$ C$_{14}$H$_{13}$F$_2$N$_2$O$_3$ requires 331.0)

Example 113

Compound 136

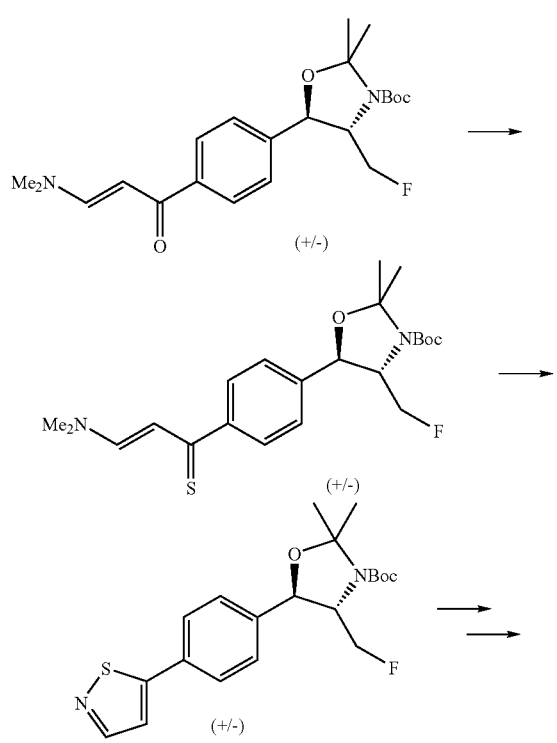

The starting material in Example 108 was reacted with Lawesson's reagent and the product was cyclized to the biaryl intermediate with hydroxylamine-O-sulfonic acid in methanol in presence of pyridine. LRMS (ESI$^+$) m/z: 363.0 (M−H$^+$ C$_{14}$H$_{13}$Cl$_2$FN$_2$O$_2$S requires 363.0)

Example 114

Compound 137

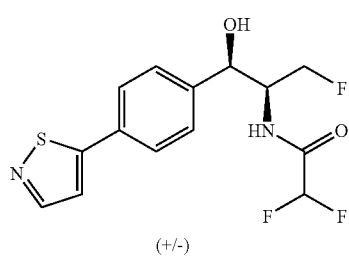

(+/−)

Compound 137 was synthesized using the procedure in Example 113. LRMS (ESI$^+$) m/z: 331.0 (M−H$^+$ C$_{14}$H$_{13}$F$_3$N$_2$O$_2$S requires 331.0)

Example 115

Compound 138 (Mixture of Diastereoisomers)

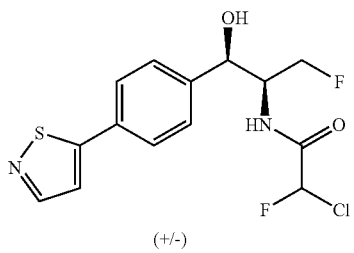

(+/−)

Compound 138 was synthesized using the procedure in Example 113. LRMS (ESI$^+$) m/z: 347.0 (M−H$^+$ C$_{14}$H$_{13}$ClF$_2$N$_2$O$_2$S requires 347.0)

Example 116

Compound 139

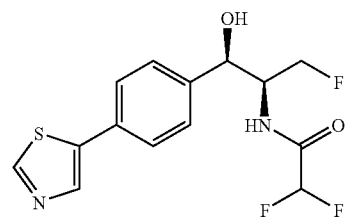

Compound 139 was synthesized using the procedure in Example 96 starting from the desired enantiomer of intermediate 19. LRMS (ESI$^+$) m/z: 331.0 (M−H$^+$ C$_{14}$H$_{13}$F$_3$N$_2$O$_2$S requires 331.0)

Example 117

Compound 140 (Mixture of Diastereoisomers)

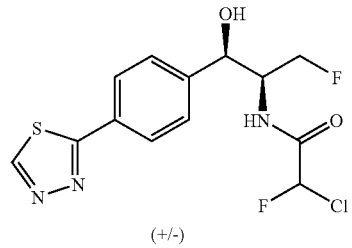

Compound 140 was synthesized using the procedure in Example 41. LRMS (ESI$^+$) m/z: 348.0 (M–H$^+$ $C_{13}H_{12}ClF_2N_3O_2S$ requires 348.0)

Example 118

Compound 141

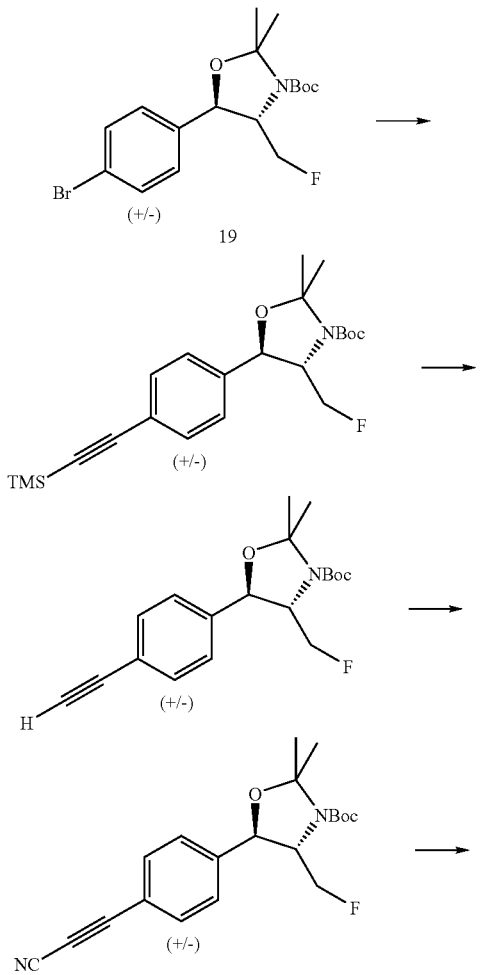

Intermediate 19 was reacted with trimethylsilylacetylene in presence of copper iodide and PdCl$_2$(PPh$_3$)$_2$. The product was desilylated by treatment with potassium carbonate in methanol. The cyanoacetylene intermediate was reacting acetylene with n-butyllithium, which was then reacted with tosylcyanide. Cyclization to the 3-aminoisoxazole was performed by treatment of the cyanoacetylene with hydroxylamine in ethanol. LRMS (ESI$^+$) m/z: 330.0 (M–H$^+$ $C_{14}H_{14}F_3N_3O_3$ requires 330.0)

Example 119

Compound 142

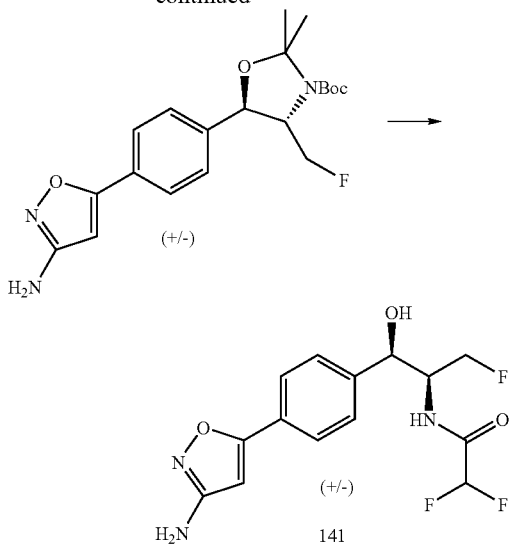

Compound 142 was synthesized using the procedure in Example 118. LRMS (ESI$^+$) m/z: 362.0 (M–H$^+$ $C_{14}H_{14}Cl_2FN_3O_3$ requires 362.0)

Example 120

Compound 143

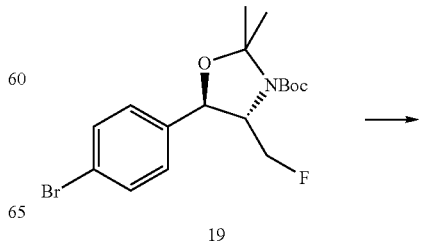

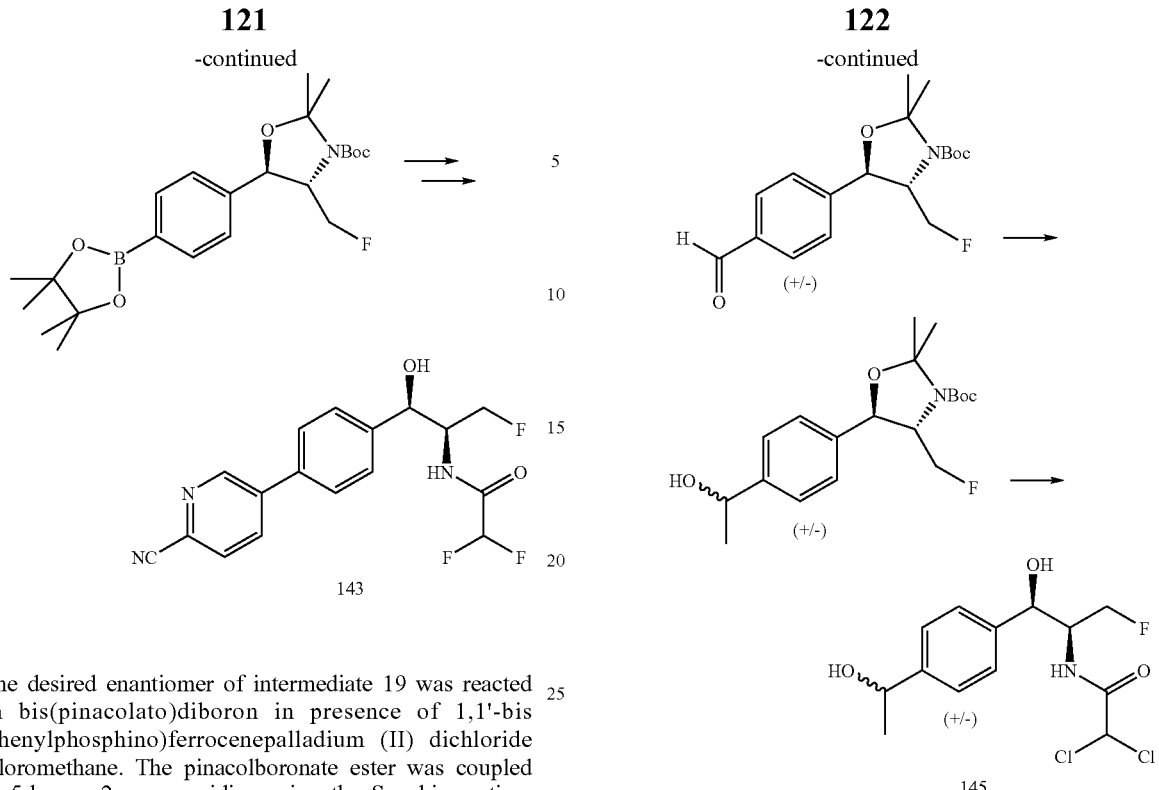

The desired enantiomer of intermediate 19 was reacted with bis(pinacolato)diboron in presence of 1,1'-bis(diphenylphosphino)ferrocenepalladium (II) dichloride dichloromethane. The pinacolboronate ester was coupled with 5-bromo-2-cyanopyridine using the Suzuki reaction. LRMS (ESI$^+$) m/z: 350.0 (M–H$^+$ $C_{17}H_{14}F_3N_3O_2$ requires 350.0)

Example 121

Compound 144

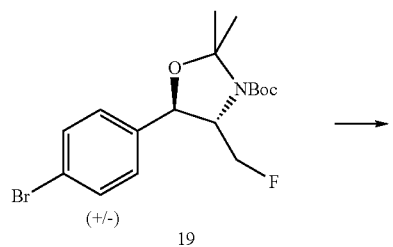

Compound 144 was synthesized using the procedure in Example 120. LRMS (ESI$^+$) m/z: 382.0 (M–H$^+$ $C_{17}H_{14}Cl_2FN_3O_2$ requires 382.0)

Example 122

Compound 145 (Mixture of Diastereoisomers)

Intermediate 19 was reacted with n-butyllithium and then with dimethylformamide. The formyl intermediate was reacted with methylmagnesium bromide to give the benzylic alcohol as a mixture of diastereisomers. LRMS (ESI$^+$) m/z: 324.0 (M–H$^+$ $C_{13}H_{16}Cl_2FNO_3$ requires 324.0)

Example 123

Compound 146

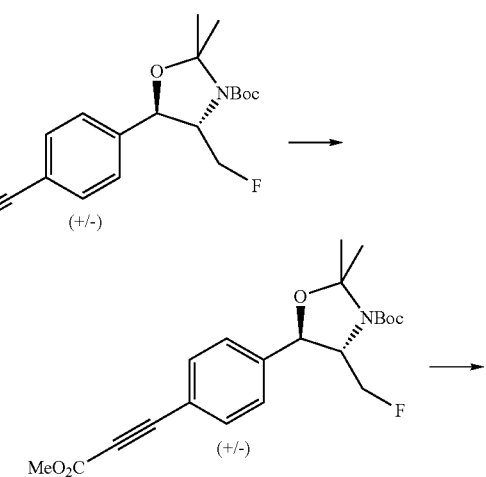

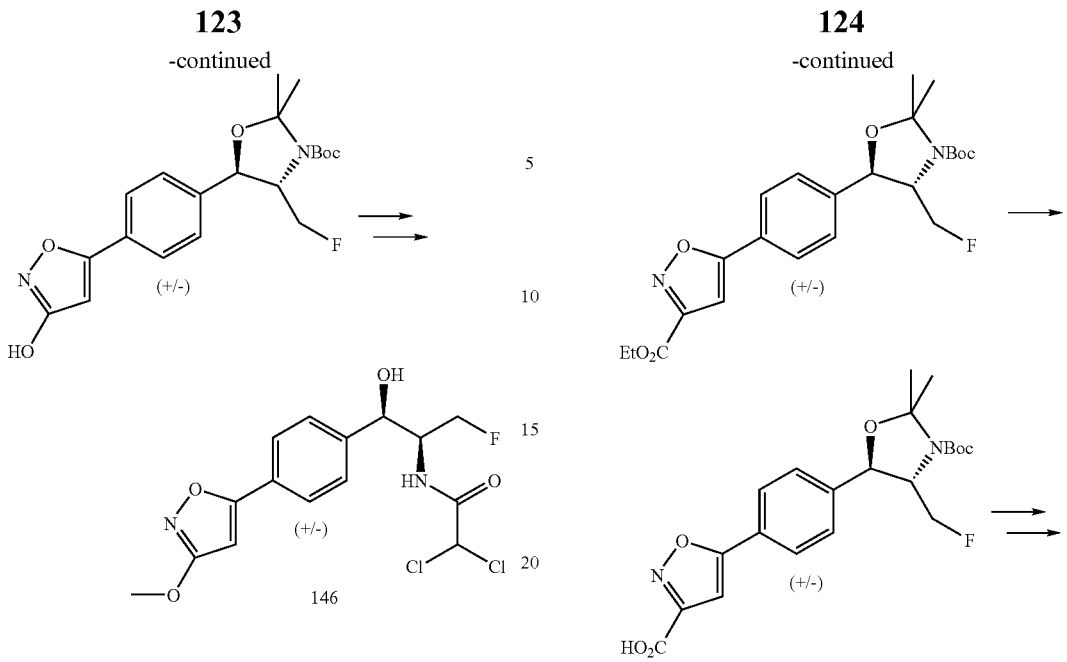

The starting acetylene, prepared as described in Example 118, was reacted with n-butyllithium followed by addition of carbon dioxide and the resulting acid was esterified with diazomethane in ethyl acetate/diethyl ether. The 3-hydroxyisoxazole was obtained by reacting the ester with hydroxylamine and was then methylated with diazomethane in ethyl acetate/diethyl ether. LRMS (ESI+) m/z: 377.0 (M−H+ $C_{15}H_{15}Cl_2FN_2O_4$ requires 377.0)

Example 124

Compound 147

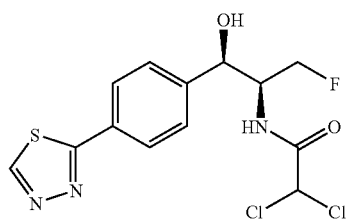

Compound 147 was synthesized by the method of Example 120 using 2-bromo-1,3,4-thiadiazole in a Suzuki coupling. LRMS (ESI+) m/z: 364.0 (M−H+ $C_{13}H_{12}Cl_2FN_3O_2S$ requires 364.0)

Example 125

Compound 148

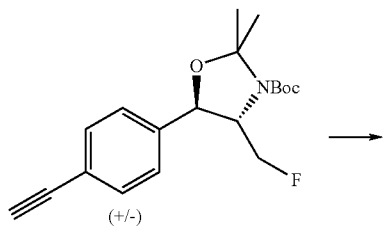

The starting acetylene was obtained as described in Example 118. The 3-carboethoxy isoxazole intermediate was obtained by cycloaddition of the nitrile oxide generated in situ from ethyl nitroacetate, di-t-butyldicarbonate and 4-dimethylaminopyridine. The amide was obtained from the 3-carboethoxy isoxazole intermediate by hydrolysis to the acid, conversion to the acyl chloride and reaction with ammonia. LRMS (ESI+) m/z: 358.0 (M−H+ $C_{15}H_{14}F_3N_3O_4$ requires 358.0)

Example 126

Compound 149

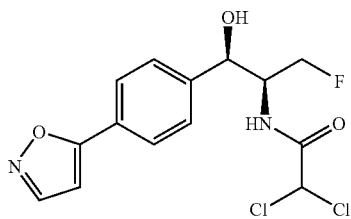

Compound 149 was synthesized using the procedure in Example 108 starting from the desired enantiomer of intermediate 19. LRMS (ESI+) m/z: 347.0 (M−H+ $C_{14}H_{13}Cl_2FN_2O_3$ requires 347.0)

Example 127

Compound 150

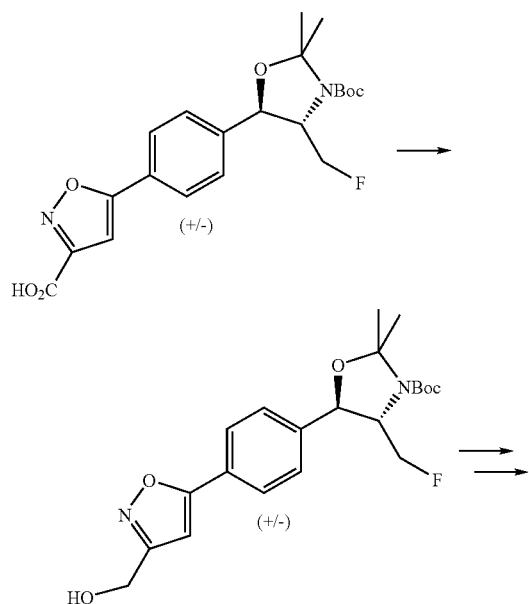

The 3-carboxyisoxazole intermediate obtained as described in Example 125 was converted into the acid chloride using Vilsmeyer reagent in dimethylformamide. The crude product was reduced to the 3-hydroxymethyl isoxazole intermediate with tetrabutylammonium borohydride in THF. LRMS (ESI$^+$) m/z: 377.0 (M−H$^+$ $C_{15}H_{15}Cl_2FN_2O_4$ requires 377.0)

Example 128

Compound 151

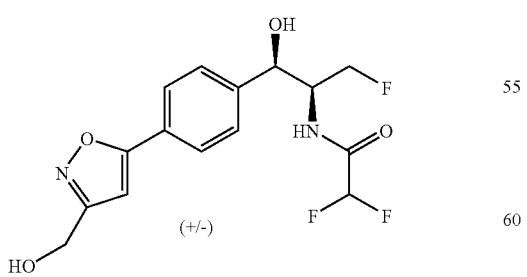

Compound 151 was synthesized using the procedure in Example 127. LRMS (ESI$^+$) m/z: 345.0 (M−H$^+$ $C_{15}H_{15}F_3N_2O_4$ requires 345.0)

Example 129

Compound 152

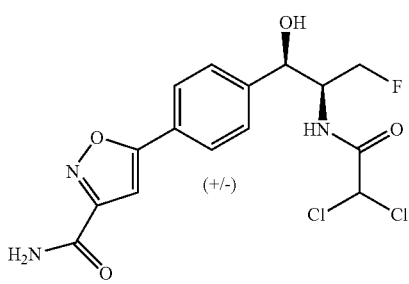

Compound 152 was synthesized using the procedure in Example 125. LRMS (ESI$^+$) m/z: 390.0 (M−H$^+$ $C_{15}H_{14}Cl_2FN_3O_4$ requires 390.0)

Example 130

Compound 153

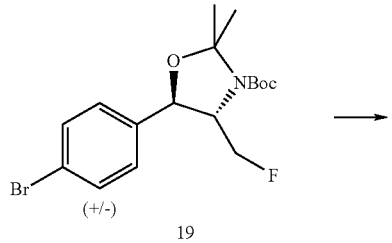

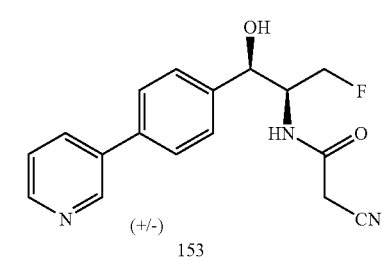

Compound 153 was synthesized using the procedure in Example 40. EDC/HOBT was used to acylate the amino intermediate with cyanoacetic acid. LRMS (ESI$^+$) m/z: 314.0 (M−H$^+$ $C_{17}H_{16}FN_3O_2$ requires 314.0)

Example 131

Compound 154

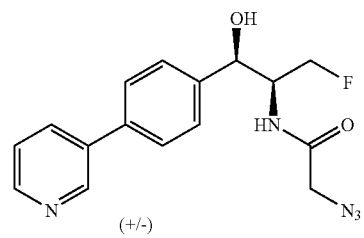
(+/-)

Compound 154 was synthesized using the procedure in Example 130. LRMS (ESI$^+$) m/z: 330.0 (M−H$^+$ C$_{16}$H$_{16}$FN$_5$O$_2$ requires 330.0)

Example 132

Compound 155

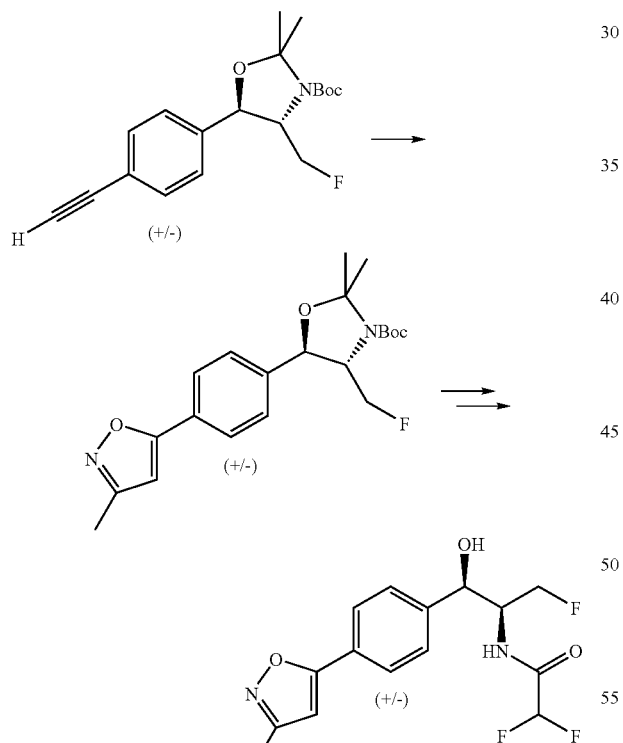

The starting acetylene was obtained as described in Example 118. The 3-methyl isoxazole intermediate was obtained by cycloaddition of the nitrile oxide generated in situ from nitroethane, di-t-butyldicarbonate and 4-dimethylaminopyridine. LRMS (ESI$^+$) m/z: 329.0 (M−H$^+$ C$_{15}$H$_{15}$F$_3$N$_2$O$_3$ requires 329.0)

Example 133

Compound 156

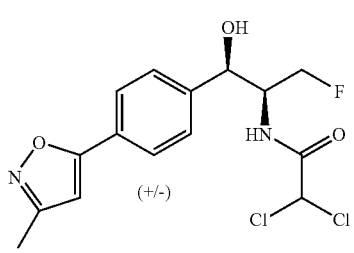
(+/-)

Compound 156 was synthesized using the procedure in Example 132. LRMS (ESI$^+$) m/z: 361.0 (M−H$^+$ C$_{15}$H$_{15}$Cl$_2$FN$_2$O$_3$ requires 361.0)

Example 134

Compound 157

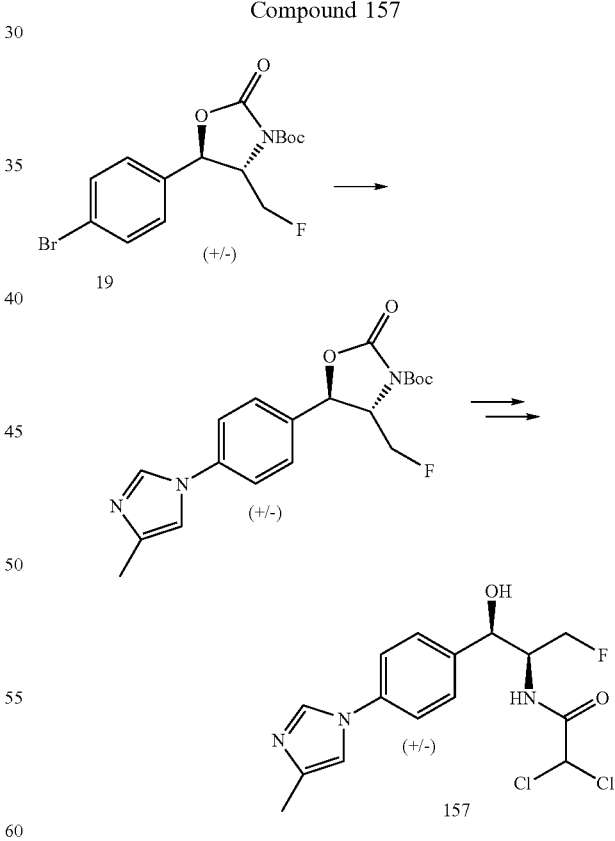

Intermediate 19 was reacted with 4-methylimidazole in refluxing dimethylformamide in the presence of copper powder. LRMS (ESI$^+$) m/z: 3460.0 (M−H$^+$ C$_{14}$H$_{14}$Cl$_2$FN$_3$O$_2$ requires 346.0)

Example 135

Compound 158

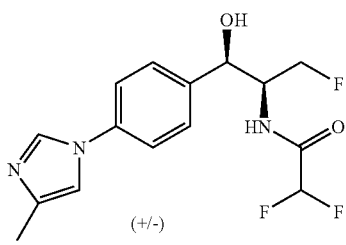

(+/-)

Compound 158 was synthesized using the procedure in Example 134. LRMS (ESI⁺) m/z: 328.0 (M−H⁺ $C_{15}H_{16}F_3N_3O_2$ requires 328.0)

Example 136

Compound 159

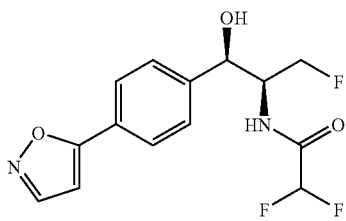

Compound 159 was synthesized using the procedure in Example 126. LRMS (ESI⁺) m/z: 315.0 (M−H⁺ $C_{14}H_{13}F_3N_2O_3$ requires 315.0)

Example 137

Compound 160

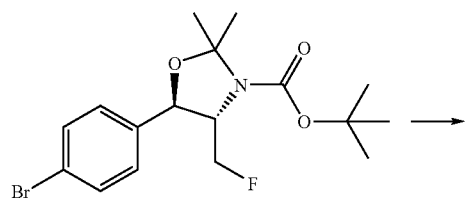

A mixture of the desired enantiomer of intermediate 19 (1 g, 2.5 mmol), potassium carbonate (712 mg, 5 mmol), and propiolamide (1.07 g, 15 mmol) in N,N-dimethylacetamide (4 mL) was stirred at room temperature while purging with N₂ for 10 minutes. Pd(PPh₃)₄ catalyst (15 mg, 0.013 mmol) was added and the mixture was purged with N₂ for another 5 minutes. The resulting mixture was stirred at 100° C. for 9 hrs. After cooling to room temperature, the crude was flash silica gel chromatographed to give the coupling product (601 mg). ¹H NMR (300 MHz, CDCl₃): δ 1.49 (s, 9H), 1.59 (s, 3H), 1.70 (s, 3H), 3.75–3.90 (m, 1H), 4.35–4.60 (m, 2H), 5.15 (d, 1H, J=7.5), 5.65 (s, 1H), 5.85 (s, 1H), 7.45 (d, 2H, J=8.4), and 7.55 (d, 2H, J=8.4).

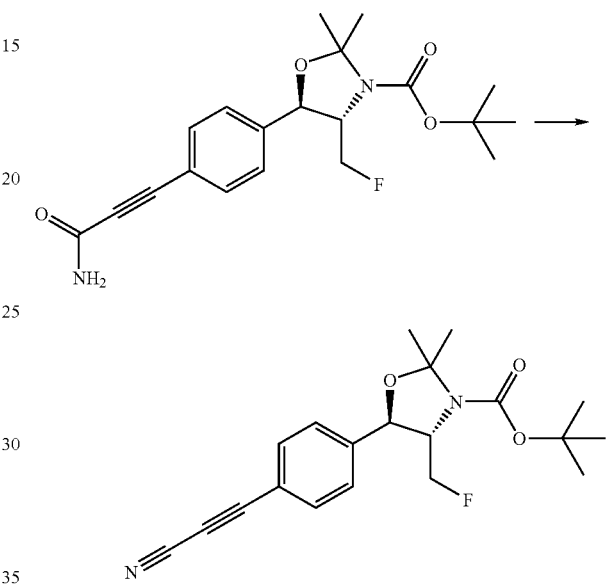

To dimethylformamamide (2 mL) was slowly added thionyl chloride (2 mL) at 0° C. and the reaction mixture was stirred at that temperature for 30 min. The solution was then cannulated to a solution of the propiolamide intermediate (600 mg) in DMF (4 mL) at 0° C. After stirring at room temperature for 30 min, the mixture was poured into ice/water (50 mL). The pH was adjusted to 7 with saturated sodium bicarbonate. The solution was extracted with ethyl acetate three times. The combined organic layers were washed with water, dried over anhydrous sodium sulfate, and purified by column chromatography to give propiolonitrile intermediate (326 mg). ¹H NMR (300 MHz, CDCl₃): δ 1.49 (s, 9H), 1.59 (s, 3H), 1.70 (s, 3H), 3.75–3.90 (m, 1H), 4.35–4.60 (m, 2H), 5.15 (d, 1H, J=7.5), 7.49 (d, 2H, J=8.4), and 7.63 (d, 2H, J=8.4).

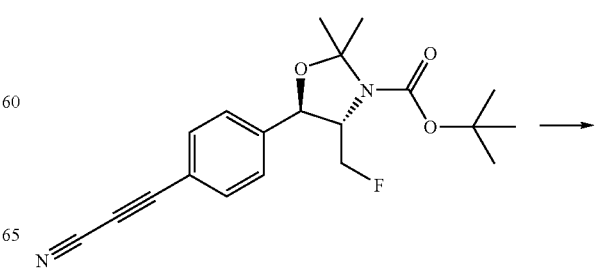

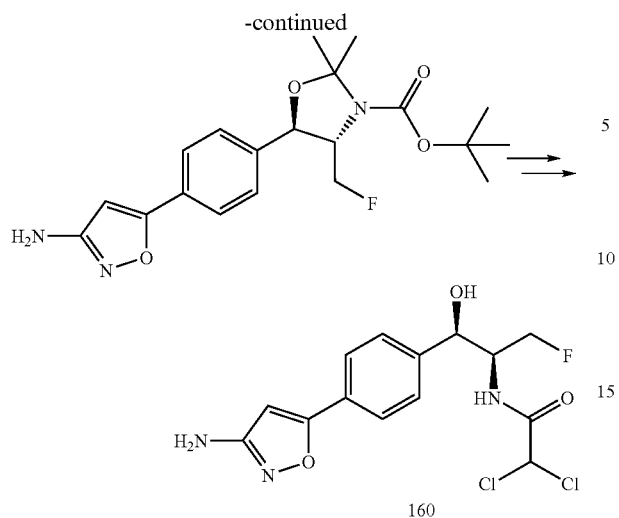

160

To a solution of sodium hydroxide (206 mg, 7 eq.) in water (2 mL), was added hydroxylamine hydrochloride (256 mg, 5 eq.). The solution was added to the propiolonitrile intermediate (263 mg) dissolved in ethanol (7 mL). The resulting mixture was stirred at room temperature for 6 hrs. Ethyl acetate was added, the organic layer was separated, washed with water, and dried with anhydrous sodium sulfate. The crude material was purified by column chromatography to give the protected 3-aminoisoxazole which was then dissolved in THF (6 mL) and 4 N HCl (6 mL), and stirred at 80° C. for 2.5 hrs. The reaction mixture was evaporated to dryness under reduced pressure. The residue was co-evaporated with methanol twice and dried overnight under vacuum. To the crude material dissolved in methanol (2 mL) was added triethylamine (2 mL), followed by methyl dichloroacetate (1 mL). The mixture was stirred at room temperature for 24 hrs. The solvent was evaporated and the mixture was purified by flash column chromatography to give compound 160 (167 mg). $^1$H NMR (300 MHz, CDCl$_3$+ CD$_3$OD): δ 4.35–4.70 (m, 3H), 5.05 (m, 1H), 5.85 (s, 1H), 6.16 (s, 1H), 7.44 (d, 2H, J=8.1), and 7.65 (d, 2H, J=8.1). LRMS (ESI$^+$) m/z: 362.0 (M−H$^+$ C$_{14}$H$_{14}$Cl$_2$FN$_3$O$_3$ requires 362.0)

Example 138

Compound 161

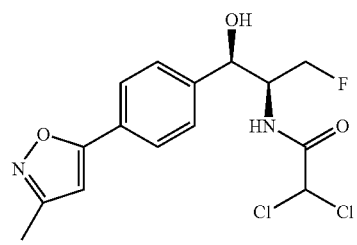

Compound 161 was synthesized using the procedure in Example 132 starting from the desired enantiomer of intermediate 19. LRMS (ESI$^+$) m/z: 361.0 (M−H$^+$ C$_{15}$H$_{15}$Cl$_2$FN$_2$O$_3$ requires 361.0)

Example 139

Compound 162

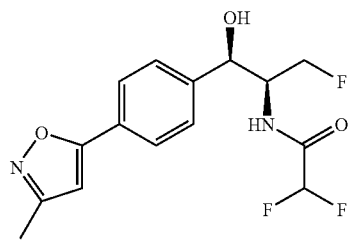

Compound 162 was synthesized using the procedure in Example 138. LRMS (ESI$^+$) m/z: 329.0 (M−H$^+$ C$_{15}$H$_{15}$F$_3$N$_2$O$_3$ requires 329.0)

Example 140

Compound 163

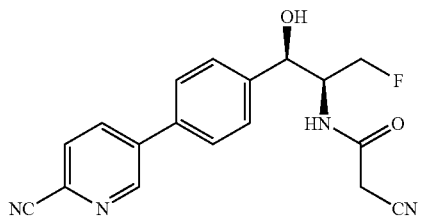

Compound 163 was synthesized using the procedure in Example 120. Dicyclohexylcarbodiimide was used to acylate the amino intermediate with cyanoacetic acid. LRMS (ESI$^+$) m/z: 339.0 (M−H$^+$ C$_{18}$H$_{15}$FN$_4$O$_2$ requires 339.0)

Example 141

Compound 164

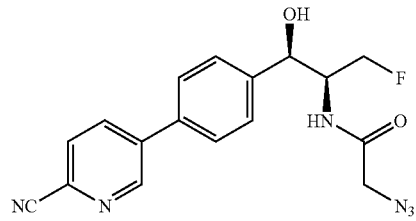

Compound 164 was synthesized using the procedure in Example 120. Dicyclohexylcarbodiimide was used to acylate the amino intermediate with azidoacetic acid. LRMS (ESI$^+$) m/z: 355.0 (M−H$^+$ C$_{17}$H$_{15}$FN$_6$O$_2$ requires 355.0)

Example 142

Compound 165

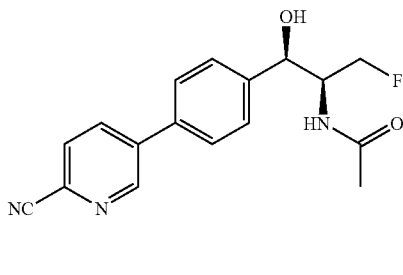

Compound 165 was synthesized using the procedure in Example 120. The amino intermediate was acetylated with acetic anhydride. LRMS (ESI$^+$) m/z: 314.0 (M-H$^+$ C$_{17}$H$_{16}$FN$_3$O$_2$ requires 314.0)

Example 143

Compound 166

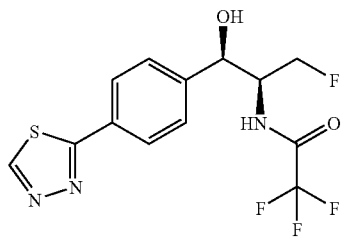

Compound 166 was synthesized using the procedure in Example 120. LRMS (ESI$^+$) m/z: 350.0 (M-H$^+$ C$_{13}$H$_{11}$F$_4$N$_3$O$_2$S requires 350.0)

Example 144

Compound 167

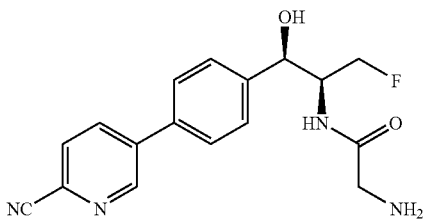

Compound 167 was synthesized using the procedure in Example 120. Dicyclohexylcarbodiimide was used to acylate the amino intermediate with N-Boc-glycine and the resulting glycinamide was deprotected with hydrochloric acid in methanol. LRMS (ESI$^+$) m/z: 329.0 (M-H$^+$ C$_{17}$H$_{17}$FN$_4$O$_2$ requires 329.0)

Example 145

Compound 168

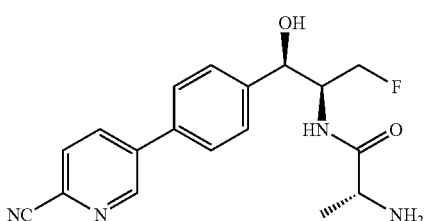

Compound 168 was synthesized using the procedure in Example 144. LRMS (ESI$^+$) m/z: 343.0 (M-H$^+$ C$_{18}$H$_{19}$FN$_4$O$_2$ requires 343.0)

Example 146

Compound 169

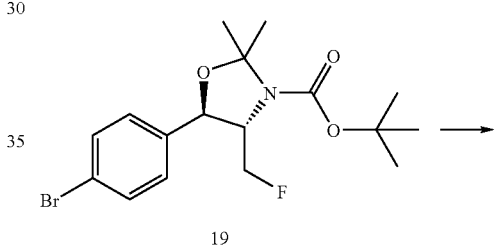

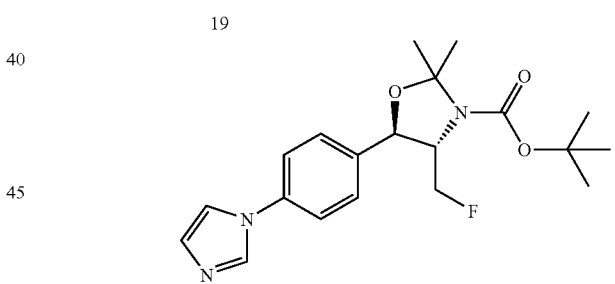

The desired enantiomer of intermediate 19 (1.16 g, 3 mmol), potassium carbonate (1.659 g, 12 mmol), imidazole (1.225 g, 18 mmol), and copper powder (191 mg, 3 mmol) in 20 mL of DMF were stirred vigorously at reflux for 4 hrs. The reaction mixture was cooled to room temperature and poured into water (100 mL). After extraction with ethyl acetate and washing of the organic extract with water (3×), the organic layer was passed through a silica gel and anhydrous sodium sulfate plug. Evaporation of solvent gave the imidazole (1.06 g). $^1$H NMR (300 MHz, CDCl$_3$): δ 1.45 (s, 9H), 1.60 (s, 3H), 1.75 (s, 3H), 3.75–3.85 (m, 1H), 4.35–4.55 (m, 2H), 5.20 (d, 1H, J=7.5), 7.22 (s, 1H), 7.28 (s, 1H), 7.41 (d, 2H, J=8.4), 7.58 (d, 2H, J=8.4), and 7.89 (s, 1H).

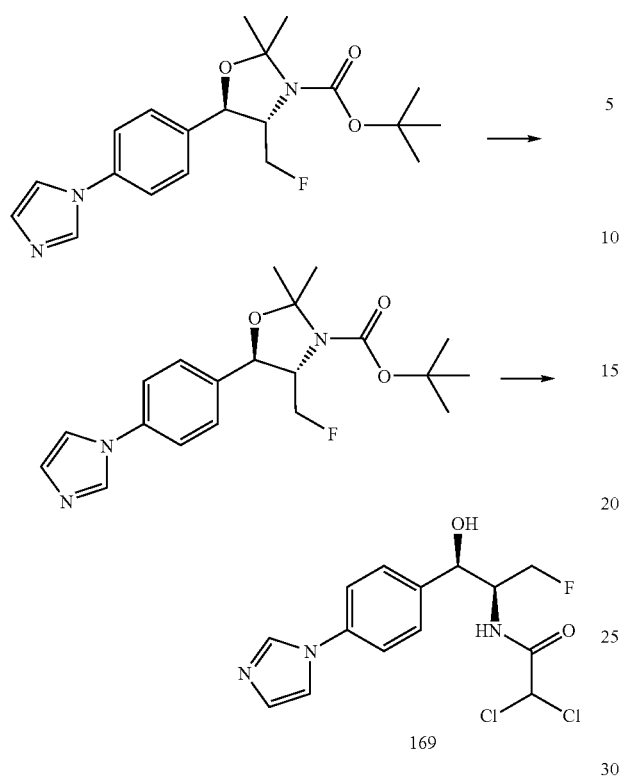

169

The imidazole intermediate (2.77 g) was dissolved in THF (20 mL) and 4 N HCl (20 mL), and stirred at 80° C. for 2.5 hrs. The reaction mixture was evaporated to dryness under reduced pressure. The residue was co-evaporated with methanol twice and dried overnight under vacuum. The crude material was dissolved in methanol (20 mL) and triethylamine (5 mL) was added, followed by methyl dichloroacetate (5 mL). The mixture was stirred at room temperature for 20 hrs. The solvent was evaporated and the mixture was purified by flash column chromatography to give compound 169 (1.1 g) as white solid. $^1$H NMR (300 MHz, CDCl$_3$): δ 4.30–4.75 (m, 3H), 5.21 (d, 1H, J=7.5), 5.86 (s, 1H), 7.05 (d, 1H, J=7.5), 7.10 (s, 1H), 7.28 (s, 1H), 7.39 (d, 2H, J=8.4), 7.52 (d, 2H, J=8.4 Hz), and 7.81 (s, 1H). LRMS (ESI$^+$) m/z: 360.0 (M–H$^+$ C$_{15}$H$_{16}$Cl$_2$FN$_3$O$_2$ requires 360.0)

Example 147

Compound 170

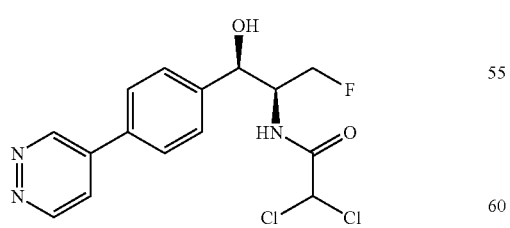

Compound 170 was synthesized by the method of Example 106 using the desired enantiomer of intermediate 19. LRMS (ESI$^+$) m/z: 358.0 (M–H$^+$ C$_{15}$H$_{14}$Cl$_2$FN$_3$O$_2$ requires 358.0)

Example 148

Compound 171

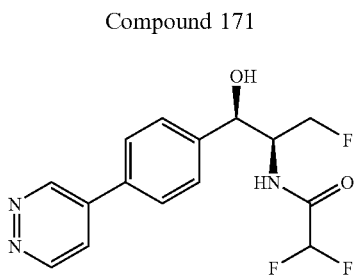

Compound 171 was synthesized using the procedure in Example 147. LRMS (ESI$^+$) m/z: 326.0 (M–H$^+$ C$_{15}$H$_{14}$F$_3$N$_3$O$_2$ requires 326.0)

Example 149

Compound 172

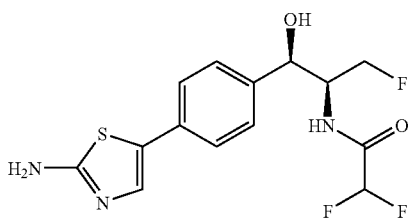

Compound 172 was synthesized by the method of Example 110 using the desired enantiomer of intermediate 19. LRMS (ESI$^+$) m/z: 346.0 (M–H$^+$ C$_{14}$H$_{14}$F$_3$N$_3$O$_2$S requires 346.0)

Example 150

Compound 173

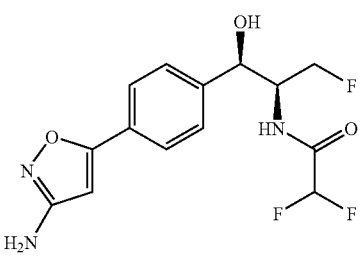

Compound 173 was synthesized using the procedure in Example 137. LRMS (ESI$^+$) m/z: 330.0 (M–H$^+$ C$_{14}$H$_{14}$F$_3$N$_3$O$_3$ requires 330.0)

Example 151

Compound 174

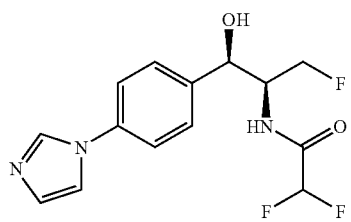

Compound 174 was synthesized using the procedure in Example 146. LRMS (ESI$^+$) m/z: 314.0 (M–H$^+$ C$_{14}$H$_{14}$F$_3$N$_3$O$_2$ requires 314.0)

Example 152

Compound 175

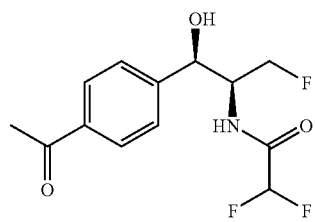

Compound 175 was synthesized using the procedure in Example 28. LRMS (ESI$^+$) m/z: 290.0 (M–H$^+$ C$_{13}$H$_{14}$F$_3$NO$_3$ requires 290.0)

Example 153

Compound 176

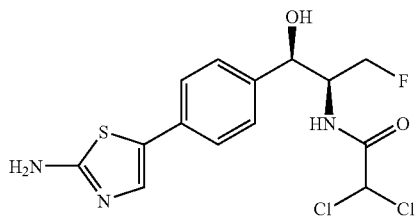

Compound 176 was synthesized using the procedure in Example 149. LRMS (ESI$^+$) m/z: 378.0 (M–H$^+$ C$_{14}$H$_{14}$Cl$_2$FN$_3$O$_2$S requires 378.0)

Example 154

Compound 177

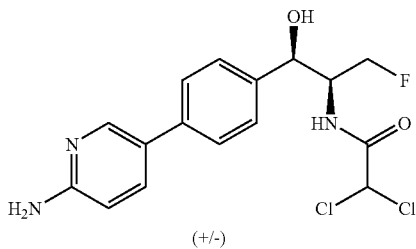

(+/–)

Compound 177 was synthesized by the method of Example 33 using the bromopyridine derivative and boronic acid 23. LRMS (ESI$^+$) m/z: 372.0 (M–H$^+$ C$_{16}$H$_{16}$Cl$_2$FN$_3$O$_2$ requires 372.0)

Example 155

Compound 178

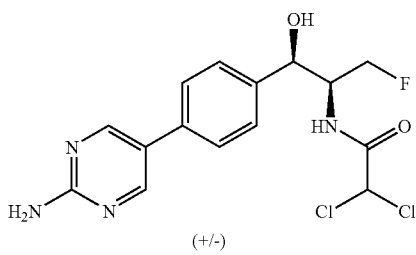

(+/–)

Compound 178 was synthesized by the method of Example 33 using a bromopyrimidine derivative and boronic acid 23. LRMS (ESI$^+$) m/z: 373.0 (M–H$^+$ C$_{15}$H$_{15}$Cl$_2$FN$_4$O$_2$ requires 373.0)

Example 156

Compound 179

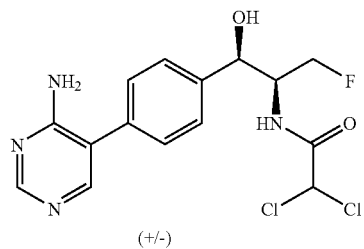

(+/–)

Compound 179 was synthesized by the method of Example 33 using the bromopyrimidine derivative and boronic acid 23. Standard conditions were used for the removal of protecting groups and the introduction of dichloroacetamide functionality. LRMS (ESI$^+$) m/z: 373.0 (M–H$^+$ C$_{15}$H$_{15}$Cl$_2$FN$_4$O$_2$ requires 373.0)

Example 157

Compound 180

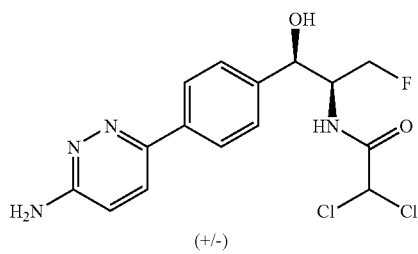

(+/-)

Compound 180 was synthesized by the method of Example 33 using the requisite chloropyridazine derivative and boronic acid 23. Standard conditions were used for the removal of protecting groups and the introduction of dichloroacetamide functionality. LRMS (ESI$^+$) m/z: 373.0 (M−H$^+$ $C_{15}H_{15}Cl_2FN_4O_2$ requires 373.0)

Conclusion

Thus, it will be appreciated that the present invention provides novel florfenicol-like compounds and methods for their use in the treatment or prevention of bacterial infection in animals or humans.

Although certain embodiments and examples have been used to describe the present invention, it will be apparent to those skilled in the art that changes in the embodiments and examples shown may be made without departing from the scope of this invention.

What is claimed:

1. A compound having the chemical formula:

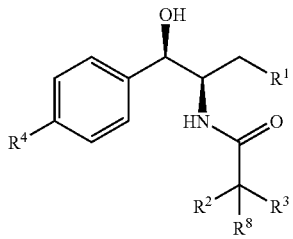

wherein $R^2$ and $R^3$ are independently selected from the group consisting of hydrogen, (1C–4C)alkyl, halo, —CF$_3$, —NH$_2$, —CN and N$_3$;
wherein $R^4$ is selected from the group consisting of:

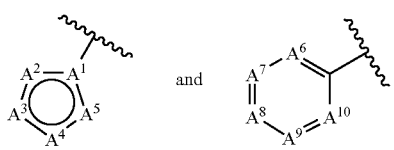

wherein $A^1$ is carbon or nitrogen, and carbon atoms in the ring are independently substituted with an entity selected from the group consisting of hydrogen, (1C–4C) alkyl, (3C–6C)cycloalkyl, (1C–4C) alkylO—, —CF$_3$, —OH, —CN, halo, (1C–4C) alkylSO—, (1C–4C)alkylSO$_2$—, NH$_2$SO$_2$—, (1C–4C)alkylNHSO$_2$—, ((1C–4C)alkyl)$_2$NSO$_2$—, —NH$_2$, (1C–4C)alkylNH—, ((1C–4C)alkyl)$_2$N—, (1C–4C)alkylSO$_2$NH—, (1C–4C)alkylC(O)—, (3C–6C)cycloalkylC(O)—, (1C–4C)alkylOC(O)—, (1C–4C)alkylC(O)NH—, —C(O)NH$_2$, (1C–4C)alkylNHC(O)— and ((1C–4C)alkyl)$_2$NC(O)—, wherein any of the alkyl groups within the substituents may be unsubstituted or substituted with a group selected from halo and hydroxy;
wherein $A^2$, $A^3$, $A^4$, an $A^5$ are independently selected from the group consisting of carbon, nitrogen, oxygen and sulfur, provided that at least one of $A^1$–$A^5$ is not carbon, that the total number of nitrogen, oxygen and sulfur atoms in the ring does not exceed 4 and that the ring is aromatic; and wherein if $A^1$ is carbon and the ring does not contain oxygen or sulfur, one of the nitrogen atoms may optionally be substituted with an entity selected from the group consisting of (1C–4C)alkyl, (1C–4C)alkylSO$_2$— and —NH$_2$; and
wherein $A^6$, $A^7$, $A^8$, $A^9$ and $A^{10}$ are independently selected from the group consisting of carbon, nitrogen and

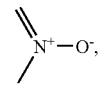

provided that only one of $A^6$–$A^{10}$ at a time can be

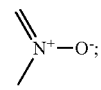

and that one, two, or three of the $A^6$–$A^{10}$ atoms are nitrogen; and wherein the carbon atoms in the ring are independently substituted with an entity selected from the group consisting of hydrogen, (1C–4C) alkyl, (3C–6C)cycloalkyl, (1C–4C)alkylO—, —CF$_3$, —OH, —CN, halo, (1C–4C)alkylSO—, (1C–4C)alkylSO$_2$—, NH$_2$SO$_2$—, (1C–4C) alkylNHSO$_2$—, ((1C–4C)alkyl)$_2$NSO$_2$—, —NH$_2$, (1C–4C)alkylNH—, ((1C–4C)alkyl)$_2$N—, (1C–4C) alkylSO$_2$NH—, (1C–4C)alkylC(O)—, (3C–6C) cycloalkylC(O)—, (1C–4C)alkylOC(O)—, (1C–4C) alkylC(O)NH—, —C(O)NH$_2$, (1C–4C)alkylNHC(O)—, ((1C–4C)alkyl)$_2$NC(O)— and —OCH$_2$O—, wherein the oxygen atoms with the —OCH$_2$O— substituent being bonded to adjacent ring carbon atoms, and wherein any of the alkyl groups within any of the substituents may be unsubstituted or substituted with a group selected from halo and hydroxy; and
wherein $R^8$ is hydrogen in all compounds, except when $R^2$ and $R^3$ are both F, in which case $R^8$ is hydrogen or F; and, the compound is either a racemate having the relative stereochemistry shown or is substantially enantiomerically pure and has the absolute stereochemistry shown.

2. The compound of claim 1, wherein $R^2$ and $R^3$ are independently selected from the group consisting of Cl and F; and wherein $R^8$ is hydrogen.

3. The compound of claim 2, wherein:
R⁴ is

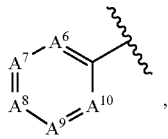

and, wherein any of A⁶–A¹⁰ that is a carbon atom is substituted with an entity selected from the group consisting of hydrogen, —NH₂, halo—, —CN, (1C–4C)alkyl—, (1C–4C)alkylC(O)—, (1C–4C)alkylSO—, (1C–4C)alkylSO₂, NH₂SO₂—, (1C–4C)alkylSO₂NH—, (1C–4C)alkylNHSO₂—, ((1C–4C)alkyl)₂NSO₂—, wherein any of the alkyl groups within any of the substituents may be unsubstituted or substituted with halo or hydroxy.

4. The compound of claim 2, wherein R⁴ is selected from the group consisting of:

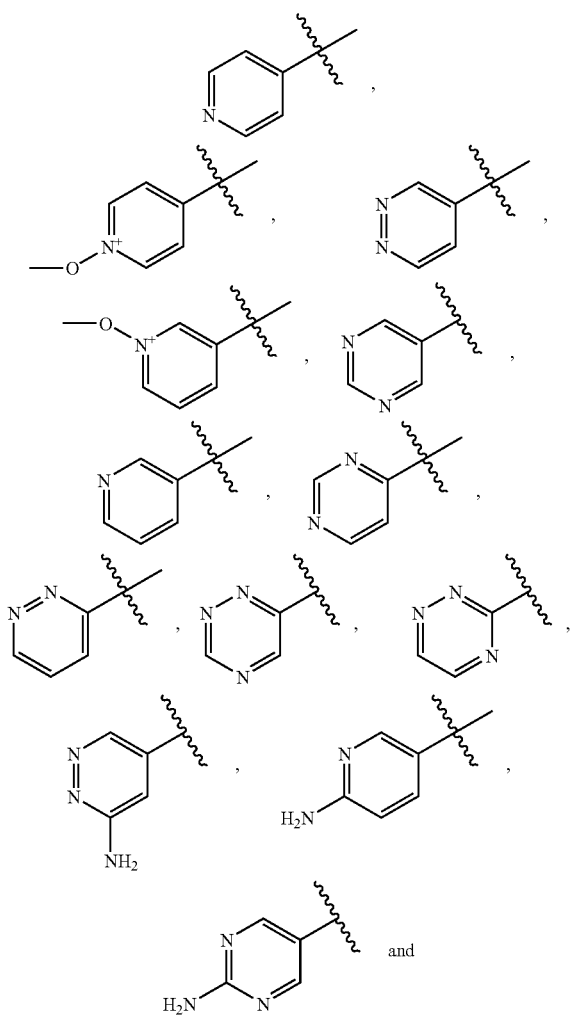

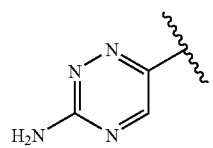

5. The compound of claim 2 wherein R⁴ is

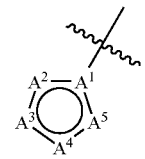

6. The compound of claim 5 wherein all carbon atoms and nitrogen atoms are unsubstituted.

7. The compound of claim 5, wherein one of the A²–A⁵ atoms that is carbon is substituted with an —NH₂ group, and all other carbon and nitrogen atoms in the ring are unsubstituted.

8. The compound of claim 5, wherein R⁴ is selected from the group consisting of:

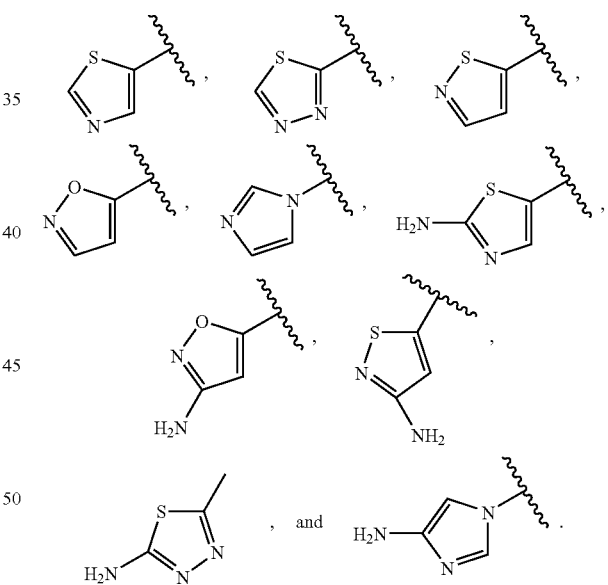

9. The compound of claim 2 selected from the group consisting of:

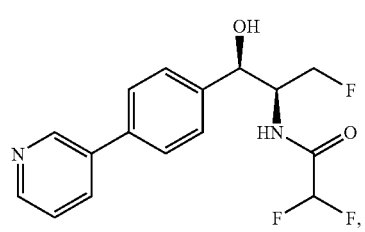

-continued
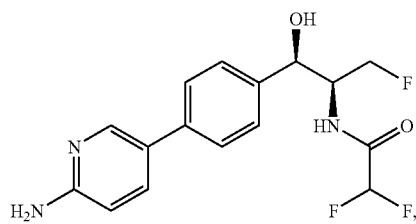
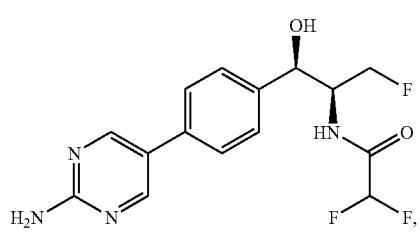
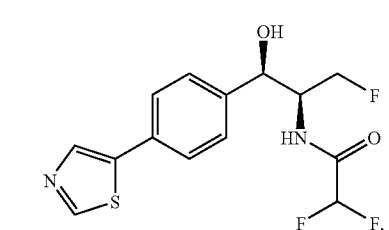
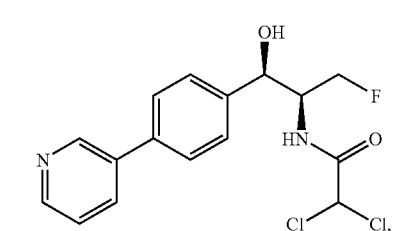
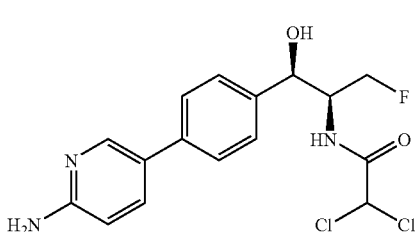
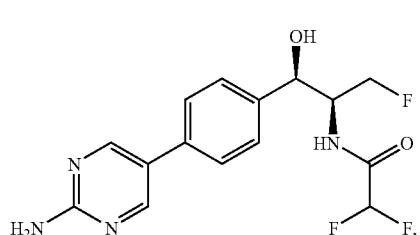
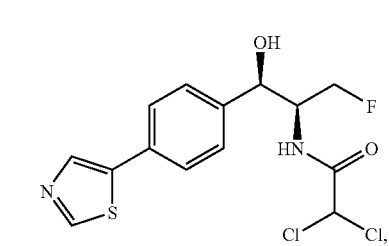
-continued
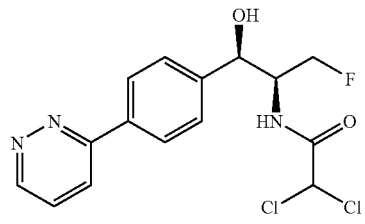
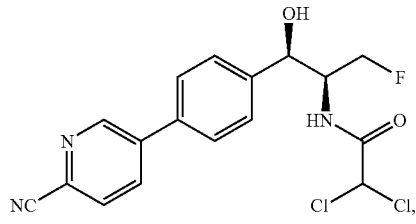
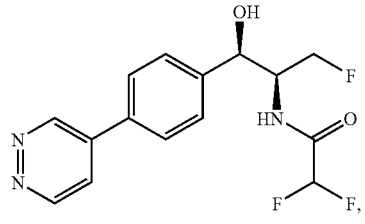
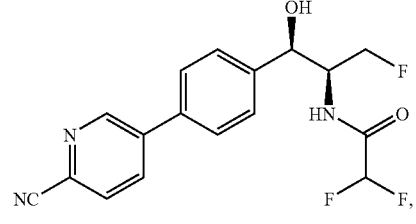
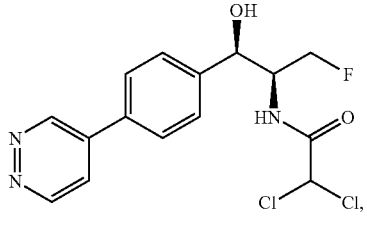
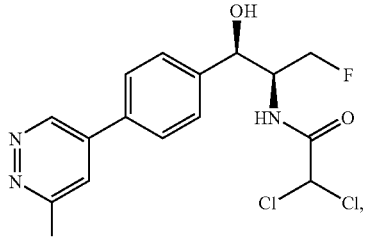
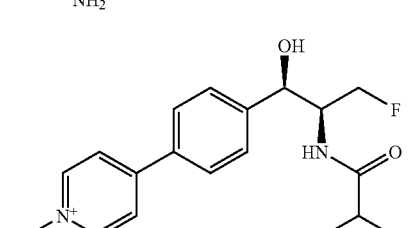

-continued
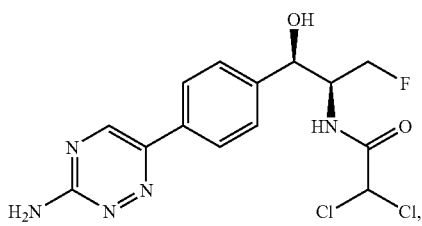
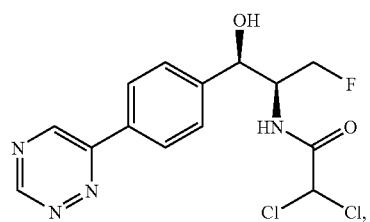
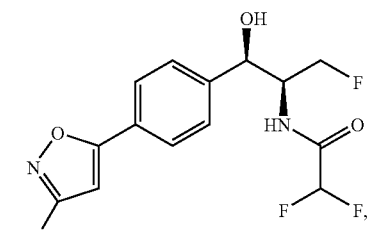
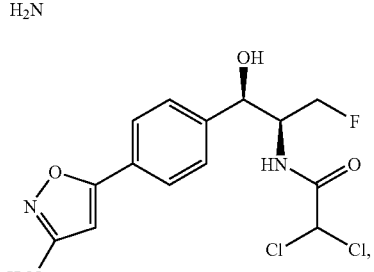
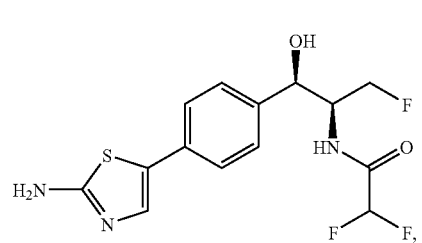
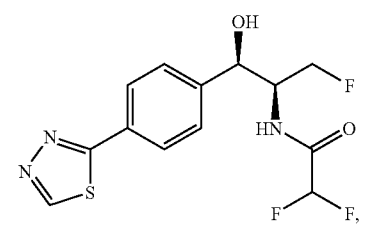
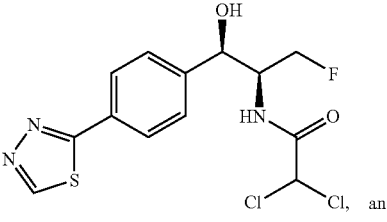, and
-continued
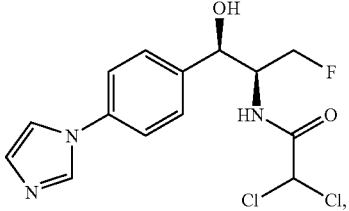
wherein the compound is either a racemate having the relative stereochemistry shown or is substantially enantiomerically pure and has the absolute stereochemistry shown.
10. The compound of claim 9 selected from the group consisting of:
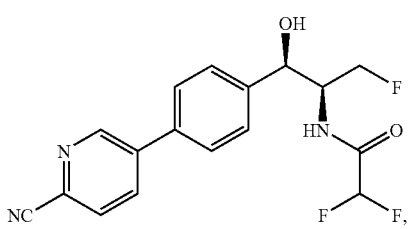
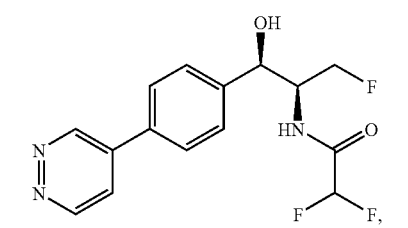
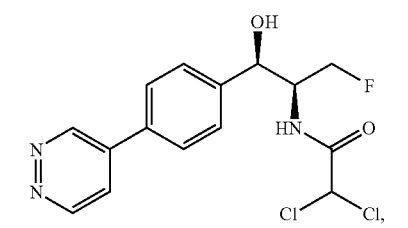
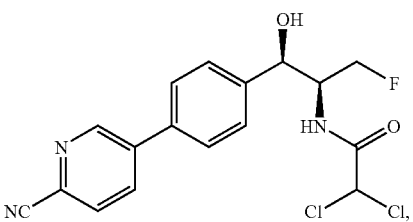
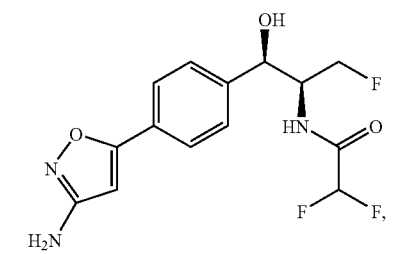

-continued

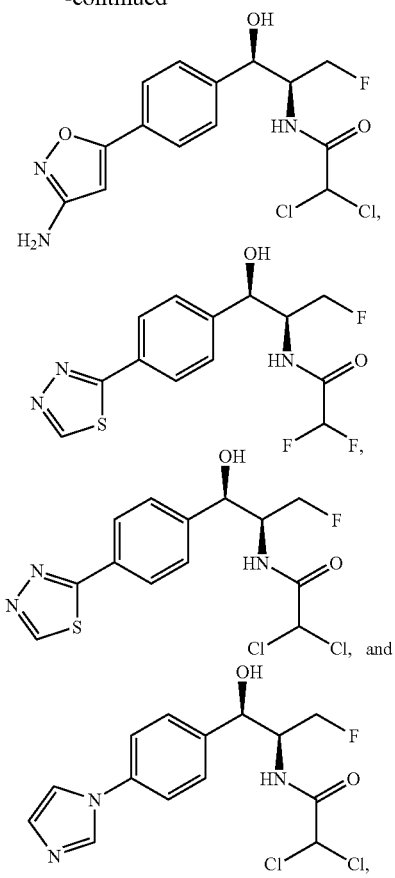

wherein the compound is either a racemate having the relative stereochemistry shown or is substantially enantiomerically pure and has the absolute stereochemistry shown.

11. The compound of claim 1, wherein:
R⁴ is

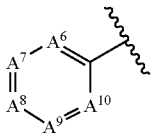

and, wherein any of $A^6$–$A^{10}$ that is a carbon atom is substituted with an entity selected from the group consisting of hydrogen, —NH₂, halo—, —CN, (1C–4C)alkyl—, (1C–4C)alkylC(O)—, (1C–4C)alkylSO—, (1C–4C)alkylSO₂, NH₂SO₂—, (1C–4C)alkylSO₂NH—, (1C–4C)alkylNHSO₂—, ((1C–4C)alkyl)₂NSO₂—, wherein any of the alkyl groups within any of the substituents may be unsubstituted or substituted with halo or hydroxy.

12. The compound of claim 1, wherein:
R⁴ is

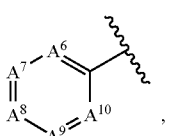

wherein any of $A^6$–$A^{10}$ that are carbon atoms are optionally substituted with —NH₂, and wherein all remaining $A^6$–$A^{10}$ carbon atoms are unsubstituted.

13. The compound of claim 1, wherein R⁴ is selected from the group consisting of:

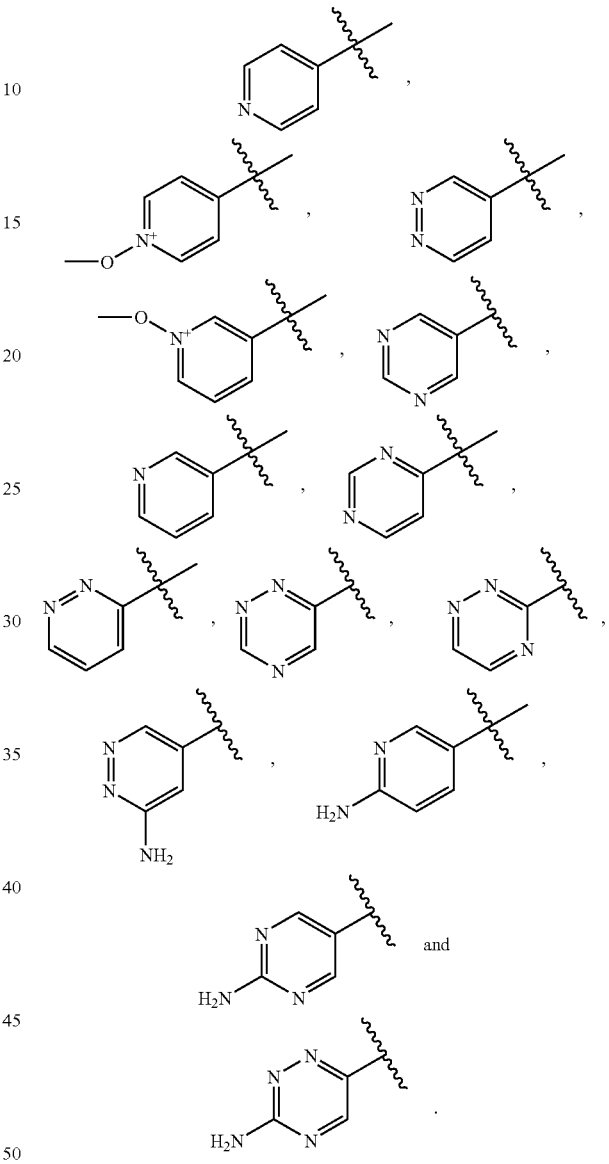

14. The compound of claim 1, wherein R⁴ is

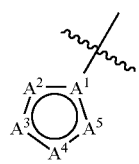

15. The compound of claim 14, wherein all carbon atoms and nitrogen atoms are unsubstituted.

16. The compound of claim 14, wherein one of the $A^2$–$A^5$ atoms that is carbon is substituted with an —NH₂ group, and all other carbon and nitrogen atoms in the ring are unsubstituted.

17. The compound of claim 14, wherein R⁴ is selected from the group consisting of:

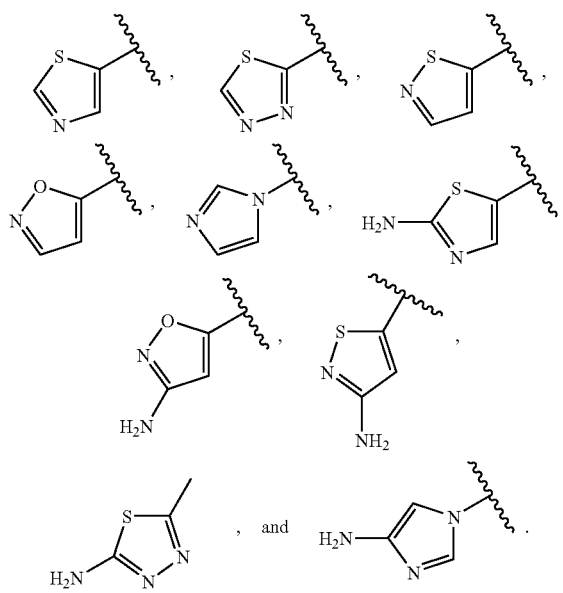

18. The compound of claim 1, selected from the group consisting of:

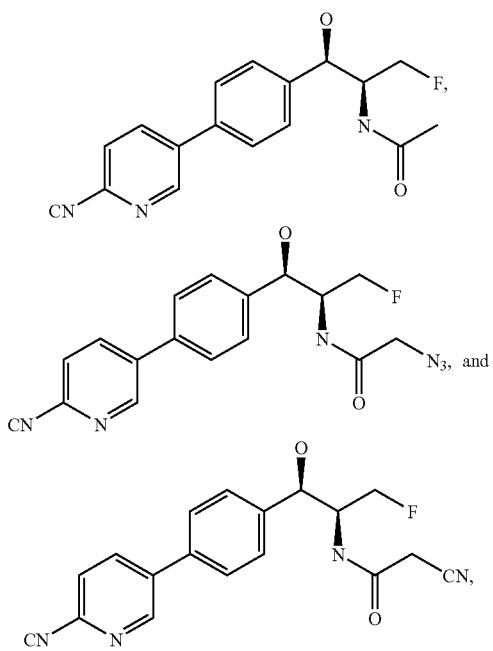

wherein the compound is either a racemate having the relative stereochemistry shown or is substantially enantiomerically pure and has the absolute stereochemistry shown.

19. A compound having the chemical formula:

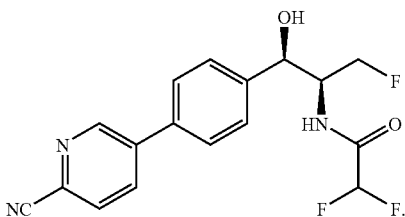

20. The compound of claim 19, wherein the compound is a racemate having the relative stereochemistry shown.

21. The compound of claim 19, wherein the compound is substantially enantiomerically pure and has a 1-(R)-2-(S) absolute configuration.

22. A method of treating a bacterial infection in a patient, comprising administering to the patient a pharmaceutically effective amount of the compound of claim 1.

23. The method of claim 22, wherein the bacterial infection is caused by a bacteria of the genus *Pasteurella, Haemophilus, Fusobacterium, Bactericides, Aeromonas, Enterobacter, Escherichia, Klebsiella, Salmonella, Shigella, Actinobacillus, Streptococcus, Mycoplasma, Edwardsiella, Staphylococcus, Enterococcus, Bordetella, Proteus,* or *Munnheimia.*

24. The method of claim 23, wherein the bacterial infection is caused by *Munnheimia haemolytica, Pasteurella multocida, Haemophilus somnus, Fusobacterium necrophorum, Bactericides melaninogenicus, Actinobacillus pleuropneumoniae, Streptococcus suis, Salmonella cholerasuis, Mycoplasma bovis, Mycoplasma hyopneumoniae, Mycoplasma hyorhinis, Mycoplasma gallisepticum, Edwardsiella ictaluri, Escherichia coli, Enterobacter cloacae, Staphylococcus aureus, Staphylococcus intermedius, Enterococcus faecalis, Enterococcus faecium, Klebsiella pneumoniae, Klebsiella oxytoca, Enterobacter cloacae, Proteus mirabilis,* or *Aeromonas salmonicida.*

25. A pharmaceutical composition comprising the compound of claim 1 or a physiological acceptable salt thereof and a physiologically acceptable carrier.

26. A pharmaceutical composition comprising the compound of claim 19 or a physiological acceptable salt thereof and a physiologically acceptable carrier.

27. A pharmaceutical composition comprising the compound of claim 2 or a physiological acceptable salt thereof and a physiologically acceptable carrier.

* * * * *

UNITED STATES PATENT AND TRADEMARK OFFICE
CERTIFICATE OF CORRECTION

PATENT NO. : 7,041,670 B2  
APPLICATION NO. : 10/410330  
DATED : May 9, 2006  
INVENTOR(S) : Constantine G. Boojamra Page 1 of 1

It is certified that error appears in the above-identified patent and that said Letters Patent is hereby corrected as shown below:

In the Title of the Patent (Col. 1, Section (54), line 1):

Insert "NOVEL" before --FLORFENICOL-TYPE ANTIBIOTICS--

Column 143, lines 10 – 20, the left-hand formula should appear as follows:

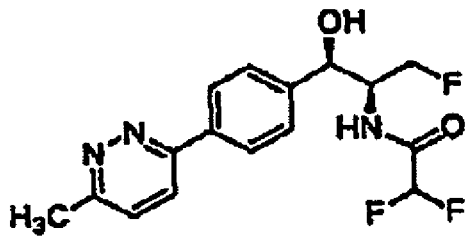

Claim 23 (Column 150, line 23) and Claim 24 (Column 150, line 33)

Change "Bactericides" to --Bacterioides--.

Claim 24 (Column 150, line 31)

Change "Munngeimia" to --Mannhemia--.

Signed and Sealed this

Twenty-eighth Day of November, 2006

JON W. DUDAS  
*Director of the United States Patent and Trademark Office*